(12) United States Patent
Steurer

(10) Patent No.: US 8,710,055 B2
(45) Date of Patent: Apr. 29, 2014

(54) TRIAZOLYLPHENYL SULFONAMIDES AS SERINE/THREONINE KINASE INHIBITORS

(75) Inventor: Steffen Steurer, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 109 days.

(21) Appl. No.: 13/329,376

(22) Filed: Dec. 19, 2011

(65) Prior Publication Data

US 2012/0322803 A1  Dec. 20, 2012

(30) Foreign Application Priority Data

Dec. 21, 2010 (EP) .................................... 10196274
Sep. 16, 2011 (EP) .................................... 11181598

(51) Int. Cl.
*A61K 31/5377* (2006.01)
*A61K 31/496* (2006.01)
*A61K 31/506* (2006.01)
*A61K 31/4439* (2006.01)
*A61K 31/4196* (2006.01)
*C07D 413/02* (2006.01)
*C07D 413/14* (2006.01)
*C07D 401/02* (2006.01)
*C07D 401/14* (2006.01)
*C07D 249/08* (2006.01)

(52) U.S. Cl.
USPC .................. 514/236.2; 514/253.09; 514/256; 514/340; 514/383; 544/124; 544/129; 544/333; 544/364; 546/272.4; 548/262.2

(58) Field of Classification Search
USPC ............... 514/236.2, 253.09, 256, 340, 383; 544/124, 129, 333, 364; 546/272.4; 548/262.2
See application file for complete search history.

(56) References Cited

U.S. PATENT DOCUMENTS

| | | | |
|---|---|---|---|
| 4,218,457 A | 8/1980 | Atsumi et al. | |
| 5,990,133 A | 11/1999 | Gaster et al. | |
| 6,492,403 B1 | 12/2002 | Illig et al. | |
| 7,166,628 B2 | 1/2007 | Cogan et al. | |
| 7,214,802 B2 | 5/2007 | Cogan et al. | |
| 7,485,657 B2 | 2/2009 | Cogan et al. | |
| 7,511,042 B2 | 3/2009 | Cogan et al. | |
| 7,514,458 B2 | 4/2009 | Cogan et al. | |
| 7,531,560 B2 | 5/2009 | Cogan et al. | |
| 7,569,568 B2 | 8/2009 | Cogan et al. | |
| 7,858,804 B2 | 12/2010 | Frutos et al. | |
| 8,198,308 B2 | 6/2012 | Steurer et al. | |
| 2004/0102492 A1 | 5/2004 | Cogan et al. | |
| 2005/0153972 A1 | 7/2005 | Cogan et al. | |
| 2005/0256113 A1 | 11/2005 | Cogan et al. | |
| 2006/0079519 A1 | 4/2006 | Cogan et al. | |
| 2006/0100204 A1 | 5/2006 | Cogan et al. | |
| 2007/0032492 A1 | 2/2007 | Cogan et al. | |
| 2007/0142371 A1 | 6/2007 | Cogan et al. | |
| 2008/0009497 A1 | 1/2008 | Wittman et al. | |
| 2008/0027070 A1 | 1/2008 | Noronha et al. | |
| 2008/0045489 A1 | 2/2008 | Chao et al. | |
| 2008/0132459 A1 | 6/2008 | Moradei et al. | |
| 2008/0182837 A1 | 7/2008 | Steurer et al. | |
| 2009/0127815 A1 | 5/2009 | Tani et al. | |
| 2009/0239838 A1 | 9/2009 | Wittman et al. | |
| 2010/0240657 A1 | 9/2010 | Sapountzis et al. | |
| 2011/0059938 A1 | 3/2011 | Steurer et al. | |
| 2011/0124623 A1 | 5/2011 | Wittman et al. | |
| 2011/0183952 A1 | 7/2011 | Sapountzis et al. | |
| 2011/0312939 A1 | 12/2011 | Steurer et al. | |
| 2012/0046270 A1 | 2/2012 | Ettmayer et al. | |
| 2012/0094975 A1 | 4/2012 | Mantoulidis et al. | |
| 2013/0190286 A1 | 7/2013 | Steurer et al. | |

FOREIGN PATENT DOCUMENTS

| | | |
|---|---|---|
| EP | 1364949 A1 | 11/2003 |
| FR | 2401916 A1 | 3/1979 |
| JP | 03174153 A | 7/1991 |
| WO | 9703967 A1 | 2/1997 |
| WO | 0075120 A1 | 12/2000 |
| WO | 0162737 A2 | 8/2001 |
| WO | 03037274 A2 | 5/2003 |
| WO | 03051358 A1 | 6/2003 |
| WO | 03059886 A1 | 7/2003 |
| WO | 2004050642 A1 | 6/2004 |
| WO | 2005023761 A2 | 3/2005 |

(Continued)

OTHER PUBLICATIONS

Caplus: Chan, et al., 2002, CAS: 138:198127.

(Continued)

*Primary Examiner* — Samantha Shterengarts
(74) *Attorney, Agent, or Firm* — Michael P. Morris; Anthony P. Bottino

(57) ABSTRACT

The present invention encompasses compounds of general formula (I)

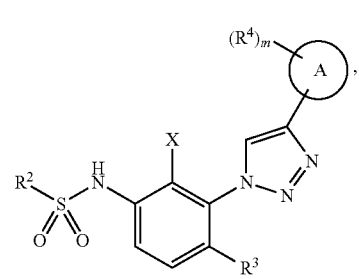

wherein the groups $R^2$ to $R^4$, A, X and m are defined as in claim 1, which are suitable for the treatment of diseases characterised by excessive or abnormal cell proliferation, pharmaceutical preparations which contain compounds of this kind and their use as medicaments.

37 Claims, No Drawings

(56) References Cited

FOREIGN PATENT DOCUMENTS

| | | | |
|---|---|---|---|
| WO | 2005030705 A1 | 4/2005 |
| WO | 2005040152 A1 | 5/2005 |
| WO | 2005056535 A1 | 6/2005 |
| WO | 2005090333 A1 | 9/2005 |
| WO | 2005115991 A1 | 12/2005 |
| WO | 2006053227 A2 | 5/2006 |
| WO | 2007056016 A2 | 5/2007 |
| WO | 2007075896 A2 | 7/2007 |
| WO | 2007121390 A1 | 10/2007 |
| WO | 2007132010 A1 | 11/2007 |
| WO | 2008003770 A1 | 1/2008 |
| WO | 2008021388 A1 | 2/2008 |
| WO | 2008079909 A1 | 7/2008 |
| WO | 2008089034 A2 | 7/2008 |
| WO | 2008106692 A1 | 9/2008 |
| WO | 2009003998 A2 | 1/2009 |
| WO | 2009003999 A2 | 1/2009 |
| WO | 2009012283 A1 | 1/2009 |
| WO | 2010010154 A1 | 1/2010 |
| WO | 2010026262 A1 | 3/2010 |
| WO | 2010034838 A2 | 4/2010 |
| WO | 2010094695 A1 | 8/2010 |
| WO | 2011117381 A1 | 9/2011 |
| WO | 2011117382 A1 | 9/2011 |
| WO | 2012085127 A1 | 6/2012 |
| WO | 2012101238 A1 | 8/2012 |
| WO | 2012104388 A1 | 8/2012 |

OTHER PUBLICATIONS

Subasinghe, N.L. et al., "Structure-based Design, Synthesis and SAR of a Novel Series of Thiopheneamidine Urokinase Plasminogen Activator Inhibitors", Bioorganice and Medicinal Chemistry Letters, 11, 2001, pp. 1379-1382.

International Search Report for PCT/EP08/058432 mailed Dec. 17, 2008.

International Search Report for PCT/EP098/058433 mailed Jun. 4, 2009.

International Search Report for PCT/EP2007/056860 mailed Nov. 15, 2007.

International Search Report for PCT/EP2009/062551 mailed Jan. 10, 2010.

International Search Report for PCT/EP2011/054611 mailed Apr. 21, 2011.

International Search Report for PCT/EP2011/054612 mailed Jul. 28, 2011.

International Search Report for PCT/EP2011/073654 mailed Feb. 2, 2012.

Patani, G.A. et al., "Bioisosterism: A Rational Approach in Drug Design", Chem Rev, 96, 1996, pp. 3147-3176.

Sparreboom, A. et al., "The Use of Oral Cytotoxic and Cytostatic Drugs in Cancer Treatment." European Journal of Cancer 38, 2002, pp. 18-22.

Williams, D.A. et al., Foye's Principles of Medicinal Chemistry, Fifth Edition, 2002, pp. 59-63.

TRIAZOLYLPHENYL SULFONAMIDES AS SERINE/THREONINE KINASE INHIBITORS

The present invention relates to new triazolylphenyl sulfonamides of general formula (I)

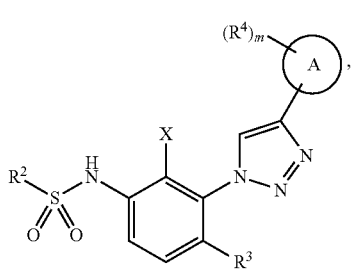

wherein the groups $R^2$ to $R^4$, A, X and m have the meanings given in the claims and specification, pharmaceutical preparations which contain compounds of this kind and their use as medicaments.

BACKGROUND TO THE INVENTION

Various fluorine-substituted phenyl sulfonamides are described in WO 2009/012283 as modulators of various kinases.

The aim of the present invention is to indicate new triazolylphenyl sulfonamides which may be used for the prevention and/or treatment of diseases characterised by excessive or abnormal cell proliferation. The triazolylphenyl sulfonamides according to the invention are distinguished by their great inhibitory effect on B-Raf V600E and their improved high potency against tumour cells, e.g. melanoma cells, which is achieved by the selective inhibition of B-Raf V600E and can also be demonstrated in vivo. Apart from the inhibitory effect and the cell potency the compounds additionally have good pharmacokinetic properties. As a result of this overall profile, the compounds according to the invention are suitable for the development of a drug.

The RAS-RAF-MAPK (mitogen-activated protein kinase) signaling pathway plays a critical role in transmitting proliferation signals generated by the cell surface receptors and cytoplasmic signaling elements to the nucleus. Constitutive activation of this pathway is involved in malignant transformation by several oncogenes. Activating mutations in RAS occur in approximately 15% of cancers, and recent data has shown that B-RAF is mutated in about 7% of cancers (Wellbrock et al., Nature Rev. Mol. Cell. Biol. 2004, 5:875-885), identifying it as another important oncogene in this pathway. In mammals, the RAF family of serine/threonine kinases comprises three members: A-RAF, B-RAF and C-RAF. However, activating mutations have so far been only identified in B-RAF underlining the importance of this isoform. It is believed that B-RAF is the main isoform that couples RAS to MEK, and that C-RAF and A-RAF signal to ERK only to fine-tune cellular responses (Wellbrock et al., Nature Rev. Mol. Cell. Biol. 2004, 5:875-885). The most common cancer mutation in B-RAF results in a valine to glutamic acid exchange at position 600 of the protein (V600E), which dramatically enhances B-RAF activity, presumably because its negative charge mimics activation loop phosphorylation (Wan et al., Cell 2004, 116: 855-867). The highest incidence of B-RAF V600 mutations occurs in malignant melanoma (38%), thyroid cancer (38%), colorectal cancer (10%), bilary tract cancer (12%) and ovarian cancer (12%), but they also occur at a low frequency in a wide variety of other cancers (frequencies of mutations according to COSMIC (*Catalogue Of Somatic Mutations In Cancer*; Wellcome Trust Sanger Institute) release v49, 29 Sep. 2010). Literature supported the hypothesis that B-RAF$^{V600E}$ mutated tumour cells seem to rely heavily on the continued activation of this pathway—a phenomenon termed "oncogene addiction"—whereas normal B-RAF$^{wt}$ cells use a broader range of signals. This provides an Achilles' heel that can be exploited therapeutically by treating patients with somatically mutated B-RAF$^{V600E}$ using orally available B-RAF inhibitors.

The key role of B-RAF$^{V600E}$ in aberrant ERK signaling and consequently oncogenesis has been demonstrated in several independent experimental approaches such as overexpression of oncogenic/mutated B-RAF in vitro and in vivo (Wan et al., Cell 2004, 116: 855-867; Wellbrock et al., Cancer Res. 2004, 64: 2338-2342), siRNA knock-down in vitro (Karasarides et al., Oncogene 2004, 23: 6292-6298) or in inducible short-hairpin RNA xenograft models where gain-of-function B-RAF signaling was found to be strongly associated with in vivo tumorigenicity (Hoeflich et al., Cancer Res. 2006, 66: 999-1006).

Treatment of B-RAF$^{V600E}$ mutated melanoma or colon carcinoma cells induces a B-RAF inhibition phenotype (e.g. reduction of phospho-MEK and phospho-ERK levels, reduction of cyclin D expression and induction of p27 expression). Consequently, these cells are locked in the G1-phase of the cell cycle and do not proliferate.

DETAILED DESCRIPTION OF THE INVENTION

It has now been found that, surprisingly, compounds of general formula (I) wherein the groups $R^2$ to $R^4$, A, X and m have the meanings given hereinafter act as inhibitors of specific signal enzymes which are involved in controlling cell proliferation. Thus, the compounds according to the invention may be used for example for the treatment of diseases connected with the activity of these signal enzymes and characterised by excessive or abnormal cell proliferation.

The present invention therefore relates to compounds of general formula (I)

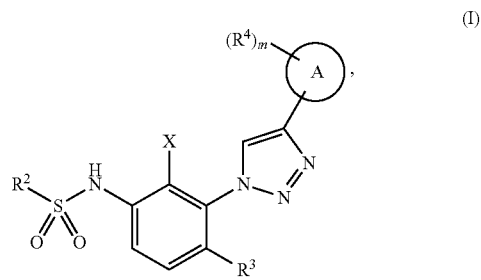

wherein
(A0)
$R^2$ is a group optionally substituted by one or more, identical or different $R^{b1}$ and/or $R^{c1}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl or $R^2$ is —NR$^{c1}$R$^{c1}$;
each $R^{b1}$ is independently selected from among —OR$^{c1}$, —NR$^{c1}$R$^{c1}$, halogen, —CN, —C(O)R$^{c1}$, —C(O)OR$^{c1}$, —C(O)NR$^{c1}$R$^{c1}$, —S(O)$_2$R$^{c1}$, —S(O)$_2$NR$^{c1}$R$^{c1}$, —NHC(O)R$^{c1}$ and —N(C$_{1-4}$alkyl)C(O)R$^{c1}$ as well as the bivalent substituent =O, wherein the latter may only be a substituent in non-aromatic ring systems;

each $R^{c1}$ independently of one another denotes hydrogen or a group selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

(B0)
$R^3$ is selected from among hydrogen, halogen, $C_{1-4}$alkyl, $C_{1-4}$alkyloxy, $C_{2-4}$alkenyl, $C_{2-4}$alkynyl, $C_{1-4}$haloalkyl, —CN, —NH($C_{1-4}$alkyl) and —N($C_{1-4}$alkyl)$_2$;

(C0)
ring A is a 5-10 membered heteroaryl;

(D0)
m denotes the number 0, 1 or 2;

each $R^4$ independently of one another denotes a group optionally substituted by one or more, identical or different $R^{a2}$ and/or $R^{b2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-11 membered heterocyclyl, or is independently selected from among —OR$^{a3}$, —NR$^{a3}$R$^{a3}$, —N(OR$^{a3}$)R$^{a3}$, halogen, —CN, —C(O)R$^{a3}$, —C(O)OR$^{a3}$, —C(O)NR$^{a3}$R$^{a3}$, —C(NH)NR$^{a3}$R$^{a3}$, —S(O)$_2$R$^{a3}$, —S(O)$_2$NR$^{a3}$R$^{a3}$, —NHC(O)R$^{a3}$ and —N($C_{1-4}$alkyl)C(O)R$^{a3}$ each $R^{a2}$ independently of one another denotes a group optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;

each $R^{b2}$ is independently selected from among —OR$^{c2}$, —NR$^{c2}$R$^{c2}$, halogen, —C(O)R$^{c2}$, —C(O)OR$^{c2}$, —C(O)NR$^{c2}$R$^{c2}$, —CN, —NHC(O)R$^{c2}$ and —NHC(O)OR$^{c2}$;

each $R^{c2}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl and 3-10 membered heterocyclyl, wherein this heterocyclyl is optionally substituted by one or more, identical or different substituents selected from among halogen, $C_{1-6}$alkyl and —C(O)—$C_{1-6}$alkyl;

each $R^{a3}$ independently of one another denotes hydrogen or a group optionally substituted by one or more, identical or different $R^{b3}$ and/or $R^{c3}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;

each $R^{b3}$ is independently selected from among —OR$^{c3}$, —NR$^{c3}$R$^{c3}$, halogen, —C(O)R$^{c3}$, —C(O)OR$^{c3}$, —C(O)NR$^{c3}$R$^{c3}$, —CN, —NHC(O)R$^{c3}$ and —NHC(O)OR$^{c3}$;

each $R^{c3}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl, $C_{1-6}$alkyl-O—$C_{1-6}$alkyl, ($C_{1-4}$alkyl)HN—$C_{1-6}$alkyl, ($C_{1-4}$alkyl)$_2$N—$C_{1-6}$alkyl, $C_{1-6}$haloalkyl, 4-16 membered heterocyclylalkyl and 3-10 membered heterocyclyl, wherein the heterocyclyl ring in aforementioned groups is optionally substituted by one or more, identical or different $C_{1-6}$alkyl;

(E0)
X denotes chlorine or fluorine;

wherein the compounds (I) may optionally also be present in the form of the tautomers, racemates, enantiomers, diastereomers and the mixtures thereof or as the respective salts of all the above-mentioned forms.

In one aspect (A1) the invention relates to compounds (I), wherein
$R^2$ is selected from among $C_{1-6}$alkyl, $C_{1-4}$alkoxy-$C_{1-4}$alkyl, 5-6 membered heteroaryl, $C_{3-6}$cycloalkyl, $C_{4-7}$cycloalkylalkyl and phenyl substituted with one or more, identical or different halogen.

In another aspect (A2) the invention relates to compounds (I), wherein
$R^2$ denotes $C_{1-6}$alkyl or phenyl substituted with one or more, identical or different halogen.

In another aspect (A3) the invention relates to compounds (I), wherein
$R^2$ denotes $C_{1-6}$alkyl.

In another aspect (A4) the invention relates to compounds (I), wherein
$R^2$ is selected from among ethyl, n-propyl, iso-propyl, n-butyl and iso-butyl.

In another aspect (A5) the invention relates to compounds (I), wherein
$R^2$ is selected from among ethyl, n-propyl, iso-propyl and iso-butyl.

In another aspect (A6) the invention relates to compounds (I), wherein
$R^2$ is n-propyl.

In another aspect (A7) the invention relates to compounds (I), wherein
$R^2$ is 5-6 membered heteroaryl.

In another aspect (A8) the invention relates to compounds (I), wherein
$R^2$ is furyl or pyridinyl.

In another aspect (A9) the invention relates to compounds (I), wherein
$R^2$ is furyl.

In another aspect (A10) the invention relates to compounds (I), wherein
$R^2$ is

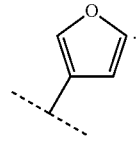

In another aspect (A11) the invention relates to compounds (I), wherein
$R^2$ is difluorophenyl.

In another aspect (B1) the invention relates to compounds (I), wherein
$R^3$ is halogen.

In another aspect (B2) the invention relates to compounds (I), wherein
$R^3$ is fluorine.

In another aspect (C1) the invention relates to compounds (I), wherein
ring A is a nitrogen-containing 5-10 membered heteroaryl.

In another aspect (C2) the invention relates to compounds (I), wherein
ring A is a nitrogen-containing 5-6 membered heteroaryl.

In another aspect (C3) the invention relates to compounds (I), wherein
ring A is selected from among pyridyl, pyrimidyl and pyrazolyl.

In another aspect (C4) the invention relates to compounds (I), wherein
ring A is pyridyl.

In another aspect (D1) the invention relates to compounds (I), wherein
m denotes 1;
$R^4$ is 3-11 membered heterocyclyl optionally substituted by one or more, identical or different $R^{a2}$ and/or $R^{b2}$
  each $R^{a2}$ independently of one another denotes a group optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;
  each $R^{b2}$ is independently selected from among $-OR^{c2}$, $-NR^{c2}R^{c2}$, halogen, $-C(O)R^{c2}$, $-C(O)OR^{c2}$, $-C(O)NR^{c2}R^{c2}$, $-CN$, $-NHC(O)R^{c2}$ and $-NHC(O)OR^{c2}$, and
  each $R_{c2}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl and 3-10 membered heterocyclyl, wherein this heterocyclyl is optionally substituted by one or more, identical or different substituents selected from among halogen, $C_{1-6}$alkyl and $-C(O)-C_{1-6}$alkyl.

In another aspect (D2) the invention relates to compounds (I), wherein
m denotes 1;
$R^4$ is 4-7 membered, nitrogen-containing heterocyclyl optionally substituted by one or more, identical or different $R^{a2}$ and/or $R^{b2}$
  each $R^{a2}$ independently of one another denotes a group optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;
  each $R^{b2}$ is independently selected from among $-OR^{c2}$, $-NR^{c2}R^{c2}$, halogen, $-C(O)R^{c2}$, $-C(O)OR^{c2}$, $-C(O)NR^{c2}R^{c2}$, $-CN$, $-NHC(O)OR^{c2}$ and $-NHC(O)OR^{c2}$, and
  each $R^{c2}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl and 3-10 membered heterocyclyl, wherein this heterocyclyl is optionally substituted by one or more, identical or different substituents selected from among halogen, $C_{1-6}$alkyl and $-C(O)-C_{1-6}$alkyl.

In another aspect (D3) the invention relates to compounds (I), wherein
m denotes 1;
$R^4$ is selected from among piperazinyl, piperidinyl and morpholinyl, all optionally substituted by one or more, identical or different $R^{a2}$ and/or $R^{b2}$
  each $R^{a2}$ independently of one another denotes a group optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;
  each $R^{b2}$ is independently selected from among $-OR^{c2}$, $-NR^{c2}R^{c2}$, halogen, $-C(O)R^{c2}$, $-C(O)OR^{c2}$, $-C(O)NR^{c2}R^{c2}$, $-CN$, $-NHC(O)R^{c2}$ and $-NHC(O)OR^{c2}$, and
  each $R^{c2}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl and 3-10 membered heterocyclyl, wherein this heterocyclyl is optionally substituted by one or more, identical or different substituents selected from among halogen, $C_{1-6}$alkyl and $-C(O)-C_{1-6}$alkyl.

In further aspects (D4)(D5)(D6) the invention relates to compounds (I) with structural aspects (D1)(D2)(D3), wherein
  each $R^{a2}$ independently of one another denotes a group optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl and 3-10 membered heterocyclyl;
  each $R^{b2}$ is independently selected from among $-OR^{c2}$, $-NR^{c2}R^{c2}$, halogen, $-C(O)NR^{c2}R^{c2}$ and $-CN$, and
  each $R^{c2}$ independently of one another denotes hydrogen or a group selected from among $C_{1-6}$alkyl, $C_{3-6}$cycloalkyl and 3-10 membered heterocyclyl, wherein this heterocyclyl is optionally substituted by one or more, identical or different substituents selected from among halogen, $C_{1-6}$alkyl and $-C(O)-C_{1-6}$alkyl.

In another aspect (D7) the invention relates to compounds (I), wherein
m denotes 1;
$R^4$ is selected from among $-OR^{a3}$ and $-NR^{a3}R^{a3}$;
  each $R^{a3}$ independently of one another denotes hydrogen or a group optionally substituted by one or more, identical or different $R^{b3}$ and/or $R^{c3}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;
  each $R^{b3}$ is independently selected from among $-OR^{c3}$, $-NR^{c3}R^{c3}$, halogen, $-C(O)R^{c3}$, $-C(O)OR^{c3}$, $-C(O)NR^{c3}R^{c3}$, $-CN$, $-NHC(O)R^{c3}$ and $-NHC(O)OR^{c3}$;
  each $R^{c3}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl, $C_{1-6}$alkyl-O-$C_{1-6}$alkyl, $(C_{1-4}$alkyl)HN-$C_{1-6}$alkyl, $(C_{1-4}$alkyl)$_2$N-$C_{1-6}$alkyl, $C_{1-6}$haloalkyl, 4-16 membered heterocyclylalkyl and 3-10 membered heterocyclyl, wherein the heterocyclyl ring in aforementioned groups is optionally substituted by one or more, identical or different $C_{1-6}$alkyl.

In another aspect (D8) the invention relates to compounds (I), wherein
m denotes 1 and
$R^4$ is imidazolyl, optionally substituted by one, two or three, identical or different $C_{1-4}$alkyl.

In another aspect (D9) the invention relates to compounds (I), wherein
m denotes 0.

In another aspect (CD1) the invention relates to compounds (I), wherein
m denotes 1;
$R^4$ and ring A together is

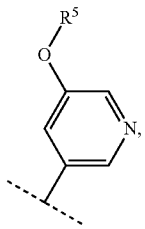

wherein
$R^5$ is $C_{1-6}$alkyl.

In another aspect (CD2) the invention relates to compounds (I), wherein
m denotes 1 and R⁴ and ring A together is

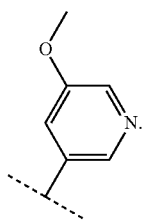

In another aspect (CD3) the invention relates to compounds (I), wherein
m denotes 1 and
R⁴ and ring A together is

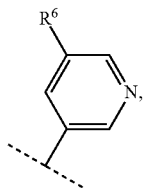

wherein
R⁶ is selected from among fluorine, chlorine and bromine.

In another aspect (CD4) the invention relates to compounds (I), wherein
m denotes 1 and
R⁴ and ring A together is

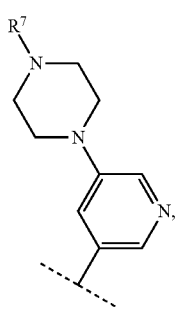

wherein
R⁷ is selected from among $C_{1-6}$alkyl, $C_{2-6}$alkynyl, $C_{3-6}$cycloalkyl, $C_{4-12}$cycloalkylalkyl, 3-6 membered heterocyclyl, —C(O)$C_{1-6}$alkyl and $C_{1-6}$alkyloxy-$C_{1-6}$alkyl.

In another aspect (CD5) the invention relates to compounds (I), wherein
m denotes 1 and
R⁴ and ring A together is

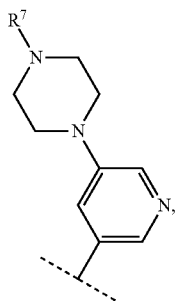

wherein
R⁷ is selected from $C_{1-6}$alkyl, $C_{3-6}$cycloalkyl, $C_{4-12}$cycloalkylalkyl, —C(O)$C_{1-6}$alkyl and $C_{1-6}$alkyloxy-$C_{1-6}$alkyl.

In another aspect (E1) the invention relates to compounds (I), wherein
X denotes chlorine.

In another aspect (E2) the invention relates to compounds (I), wherein
X denotes fluorine.

All the above-mentioned structural aspects A1 to A11, B1 and B2, C1 to C4, D1 to D9, CD1 to CD5, E1 and E2 are preferred embodiments of the various aspects A0, B0, C0, D0, CD0 and E0, respectively, wherein CD0 represents the combination of C0 and D0. The structural aspects A0 to A11, B0 to B2, C0 to C4, D0 to D9, CD0 to CD5 and E0 to E2 relating to different molecular parts of the compounds (I) according to the invention may be permutated with one another as desired in combinations ABCDE, so as to obtain preferred compounds (I). Each combination ABCDE represents and defines individual embodiments or generic amounts of compounds according to the invention. Each individual embodiment or partial quantity defined by this combination is expressly also included and is a subject of the invention.

The present invention further relates to hydrates, solvates, polymorphs, metabolites, derivatives and prodrugs of compounds of general formula (I).

The present invention further relates to a pharmaceutically acceptable salt of a compound of general formula (I) with anorganic or organic acids or bases.

In another aspect the invention relates to compounds of general formula (I)—or the pharmaceutically acceptable salts thereof—as medicaments.

In another aspect the invention relates to compounds of general formula (I)—or the pharmaceutically acceptable salts thereof—for use in a method for treatment of the human or animal body.

In another aspect the invention relates to compounds of general formula (I)—or the pharmaceutically acceptable salts thereof—for use in the treatment and/or prevention of cancer, infections, inflammations and autoimmune diseases.

In another aspect the invention relates to compounds of general formula (I)—or the pharmaceutically acceptable salts thereof—for use in a method for treatment and/or prevention of cancer, infections, inflammations and autoimmune diseases in the human and animal body.

In another aspect the invention relates to the use of compounds of general formula (I)—or the pharmaceutically acceptable salts thereof—for preparing a pharmaceutical composition for the treatment and/or prevention of cancer, infections, inflammations and autoimmune diseases.

In another aspect the invention relates to compounds of general formula (I)—or the pharmaceutically acceptable salts thereof—for use in the treatment and/or prevention of cancer.

In another aspect the invention relates to the use of compounds of general formula (I)—or the pharmaceutically acceptable salts thereof—for preparing a pharmaceutical composition for the treatment and/or prevention of cancer.

In another aspect the invention relates to compounds of general formula (I)—or the pharmaceutically acceptable salts thereof—for use in a method for treatment and/or prevention of cancer in the human or animal body.

In another aspect the invention relates to compounds of general formula (I)—or the pharmaceutically acceptable salts thereof—for use in the treatment and/or prevention of colon carcinomas, melanoma, cancer of the gall bladder and thyroid carcinomas.

In another aspect the invention relates to the use of compounds of general formula (I)—or the pharmaceutically acceptable salts thereof—for preparing a pharmaceutical composition for the treatment and/or prevention of colon carcinomas, melanoma, cancer of the gall bladder and thyroid carcinomas.

In another aspect the invention relates to a process for the treatment and/or prevention of cancer comprising administering a therapeutically effective amount of a compound of general formula (I)—or one of the pharmaceutically acceptable salts thereof—to a human being.

In another aspect the invention relates to a pharmaceutical preparation containing as active substance one or more compounds of general formula (I)—or the pharmaceutically acceptable salts thereof—optionally in combination with conventional excipients and/or carriers.

In another aspect the invention relates to a pharmaceutical preparation comprising a compound of general formula (I)—or one of the pharmaceutically acceptable salts thereof—and at least one other cytostatic or cytotoxic active substance, different from formula (I).

Definitions

Terms that are not specifically defined here have the meanings that are apparent to the skilled man in the light of the overall disclosure and the context as a whole.

As used herein, the following definitions apply, unless stated otherwise:

The use of the prefix $C_{x-y}$, wherein x and y each represent a natural number (x<y), indicates that the chain or ring structure or combination of chain and ring structure as a whole, specified and mentioned in direct association, may consist of a maximum of y and a minimum of x carbon atoms.

The indication of the number of members in groups that contain one or more heteroatom(s) (heteroalkyl, heteroaryl, heteroarylalkyl, heterocyclyl, heterocycylalkyl) relates to the total number of atoms of all the ring members or chain members or the total of all the ring and chain members.

The indication of the number of carbon atoms in groups that consist of a combination of carbon chain and carbon ring structure (cycloalkylalkyl, arylalkyl) relates to the total number of carbon atoms of all the carbon ring and carbon chain members.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$alkyl" includes for example $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

Further examples of alkyl are methyl(Me; —$CH_3$), ethyl (Et; —$CH_2CH_3$), 1-propyl(n-propyl; n-Pr; —$CH_2CH_2CH_3$), 2-propyl(i-Pr; iso-propyl; —$CH(CH_3)_2$), 1-butyl(n-butyl; n-Bu; —$CH_2CH_2CH_2CH_3$), 2-methyl-1-propyl(iso-butyl; i-Bu; —$CH_2CH(CH_3)_2$), 2-butyl(sec-butyl; sec-Bu; —$CH(CH_3)CH_2CH_3$), 2-methyl-2-propyl(tert-butyl; t-Bu; —$C(CH_3)_3$), 1-pentyl(n-pentyl; —$CH_2CH_2CH_2CH_2CH_3$), 2-pentyl(—$CH(CH_3)CH_2CH_2CH_3$), 3-pentyl(—$CH(CH_2CH_3)_2$), 3-methyl-1-butyl(iso-pentyl; —$CH_2CH_2CH(CH_3)_2$), 2-methyl-2-butyl(—$C(CH_3)_2CH_2CH_3$), 3-methyl-2-butyl(—$CH(CH_3)CH(CH_3)_2$), 2,2-dimethyl-1-propyl(neopentyl; —$CH_2C(CH_3)_3$), 2-methyl-1-butyl(—$CH_2CH(CH_3)CH_2CH_3$), 1-hexyl(n-hexyl; —$CH_2CH_2CH_2CH_2CH_2CH_3$), 2-hexyl(—$CH(CH_3)CH_2CH_2CH_2CH_3$), 3-hexyl(—$CH(CH_2CH_3)(CH_2CH_2CH_3)$), 2-methyl-2-pentyl(—$C(CH_3)_2CH_2CH_2CH_3$), 3-methyl-2-pentyl(—$CH(CH_3)CH(CH_3)CH_2CH_3$), 4-methyl-2-pentyl(—$CH(CH_3)CH_2CH(CH_3)_2$), 3-methyl-3-pentyl(—$C(CH_3)(CH_2CH_3)_2$), 2-methyl-3-pentyl(—$CH(CH_2CH_3)CH(CH_3)_2$), 2,3-dimethyl-2-butyl(—$C(CH_3)_2CH(CH_3)_2$), 3,3-dimethyl-2-butyl(—$CH(CH_3)C(CH_3)_3$), 2,3-dimethyl-1-butyl(—$CH_2CH(CH_3)CH(CH_3)CH_3$), 2,2-dimethyl-1-butyl(—$CH_2C(CH_3)_2CH_2CH_3$), 3,3-dimethyl-1-butyl(—$CH_2CH_2C(CH_3)_3$), 2-methyl-1-pentyl(—$CH_2CH(CH_3)CH_2CH_2CH_3$), 3-methyl-1-pentyl(—$CH_2CH_2CH(CH_3)CH_2CH_3$), 1-heptyl(n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl(n-octyl), 1-nonyl(n-nonyl); 1-decyl(n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkyloxy.

The term alkylene can also be derived from alkyl. Alkylene is bivalent, unlike alkyl, and requires two binding partners. Formally, the second valency is produced by removing a hydrogen atom in an alkyl. Corresponding groups are for example —$CH_3$ and —$CH_2$—, —$CH_2CH_3$ and —$CH_2CH_2$— or >$CHCH_3$ etc.

The term "$C_{1-4}$alkylene" includes for example —($CH_2$)—, —($CH_2$—$CH_2$)—, —($CH(CH_3)$)—, —($CH_2$—$CH_2$—$CH_2$)—, —($C(CH_3)_2$)—, —($CH(CH_2CH_3)$)—, —($CH(CH_3)$—$CH_2$)—, —($CH_2$—$CH(CH_3)$)—, —($CH_2$—$CH_2$—$CH_2$—$CH_2$)—, —($CH_2$—$CH_2$—$CH(CH_3)$)—, —($CH(CH_3)$—$CH_2$—$CH_2$)—, —($CH_2$—$CH(CH_3)$—$CH_2$)—, —($CH_2$—$C(CH_3)_2$)—, —($C(CH_3)_2$—$CH_2$)—, —($CH(CH_3)$—$CH(CH_3)$)—, —($CH_2$—$CH(CH_2CH_3)$)—, —($CH(CH_2CH_3)$—$CH_2$)—, —($CH(CH_2CH_2CH_3)$)—, —($CHCH(CH_3)_2$)— and —$C(CH_3)(CH_2CH_3)$—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another (combined) group such as for example in HO—$C_{x-y}$alkyleneamino or $H_2N$—$C_{x-y}$alkyleneoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl(ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another (combined) group such as for example in $C_{x-y}$alkenylamino or $C_{x-y}$alkenyloxy.

Unlike alkylene, alkenylene consists of at least two carbon atoms, wherein at least two adjacent carbon atoms are joined together by a C—C double bond and a carbon atom can only be part of one C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another (combined) group as for example in HO—$C_{x-y}$alkenyleneamino or $H_2N$—$C_{x-y}$alkenyleneoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl etc.

By the generic terms propynyl, butynyl, pentynyl, hexynyl, heptynyl, octynyl, nonynyl, decynyl etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another (combined) group, as for example in $C_{x-y}$alkynylamino or $C_{x-y}$alkynyloxy.

Unlike alkylene, alkenylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, hexynylene etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another (combined) group, as for example in HO—$C_{x-y}$alkynyleneamino or $H_2N$—$C_{x-y}$alkynyleneoxy.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —$CF$=$CF_2$, —$CCl$=$CH_2$, —$CBr$=$CH_2$, —$C$≡$C$—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenylene, haloalkynylene), unlike haloalkyl (haloalkenyl, haloalkynyl), is bivalent and requires two binding partners. Formally, the second valency is formed by removing a hydrogen atom from a haloalkyl (haloalkenyl, haloalkynyl).

Corresponding groups are for example —$CH_2F$ and —CHF—, —$CHCH_2F$ and —CHFCHF— or >$CFCH_2F$ etc.

The above definitions also apply if the corresponding halogen-containing groups are part of another (combined) group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together. In spiro-hydrocarbon rings one carbon atom (spiroatom) belongs to two rings together.

If a cycloalkyl is to be substituted, the substitutions may take place independently of one another, in the form of monoor polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl(octahydroindenyl), bicyclo[4.4.0]decyl (decahydronaphthyl), bicyclo[2.2.1]heptyl(norbornyl), bicyclo[4.1.0]heptyl(norcaranyl), bicyclo[3.1.1]heptyl(pinanyl), spiro[2.5]octyl, spiro[3.3]heptyl etc.

The above definition for cycloalkyl also applies if cycloalkyl is part of another (combined) group as for example in $C_{x-y}$cycloalkylamino, $C_{x-y}$cycloalkyloxy or $C_{x-y}$cycloalkylalkyl.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example:
cyclohexyl and

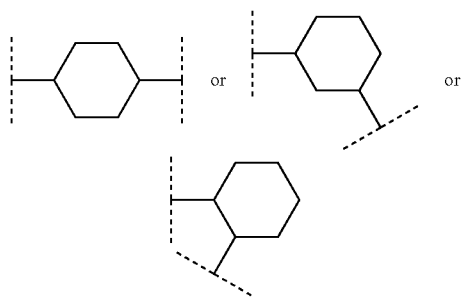

(cyclohexylene).

The above definition for cycloalkylene also applies if cycloalkylene is part of another (combined) group as for example in HO—$C_{x-y}$cycloalkyleneamino or $H_2N$—$C_{x-y}$cycloalkyleneoxy.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained.

If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl(norborna-2,5-dienyl), bicyclo[2.2.1]hept-2-enyl(norbornenyl), spiro[4,5]dec-2-enyl etc.

The above definition for cycloalkenyl also applies when cycloalkenyl is part of another (combined) group as for example in $C_{x-y}$cycloalkenylamino, $C_{x-y}$cycloalkenyloxy or $C_{x-y}$cycloalkenylalkyl.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally, the second valency is obtained by removing a hydrogen atom from a cycloalkenyl. Corresponding groups are for example:
cyclopentenyl and

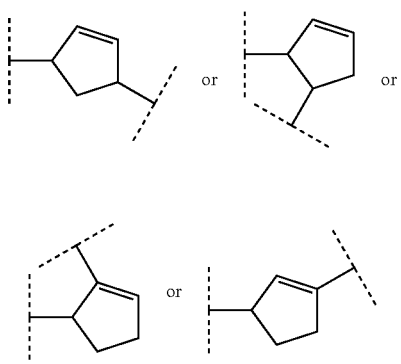

(cyclopentenylene) etc.

The above definition for cycloalkenylene also applies if cycloalkenylene is part of another (combined) group as for example in HO—$C_{x-y}$cycloalkenyleneamino or $H_2N$—$C_{x-y}$cycloalkenyleneoxy.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl(2,3-dihydroindenyl), indenyl, anthracenyl, phenanthrenyl, tetrahydronaphthyl(1,2,3,4-tetrahydronaphthyl, tetralinyl), dihydronaphthyl(1,2-dihydronaphthyl), fluorenyl etc.

The above definition of aryl also applies if aryl is part of another (combined) group as for example in arylamino, aryloxy or arylalkyl.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are for example:

phenyl and

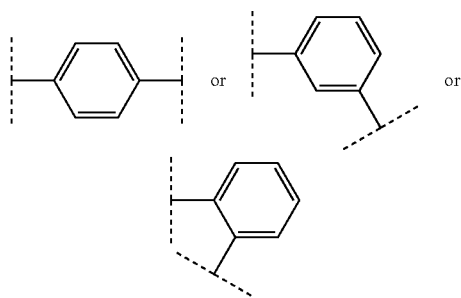

(o, m, p-phenylene),
naphthyl and

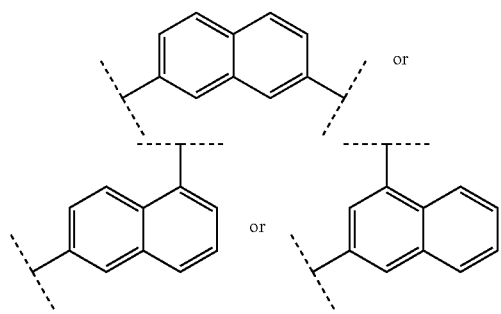

etc.

The above definition for arylene also applies if arylene is part of another (combined) group as for example in HO-aryleneamino or H$_2$N-aryleneoxy.

Heterocyclyl denotes ring systems, which are derived from the previously defined cycloalkyl, cycloalkenyl and aryl by replacing one or more of the groups —CH$_2$— independently of one another in the hydrocarbon rings by the groups —O—, —S— or —NH— or by replacing one or more of the groups =CH— by the group =N—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur→sulphoxide —SO—, sulphone —SO$_2$—; nitrogen→N-oxide). In a heterocyclyl there is no heteroaromatic ring, i.e. no heteroatom is part of an aromatic system.

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form.

By unsaturated is meant that there is at least one double bond in the ring system in question, but no heteroaromatic system is formed. In bicyclic heterorings two rings are linked together so that they have at least two (hetero)atoms in common. In spiro-heterorings one carbon atom (spiroatom) belongs to two rings together.

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1,4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydropyridinyl, 8-aza-bicyclo[3.2.1]octyl, 8-aza-bicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2,8-diaza-spiro[4,5]decyl etc.

Further examples are the structures illustrated below, which may be attached via each hydrogen-carrying atom (exchanged for hydrogen):

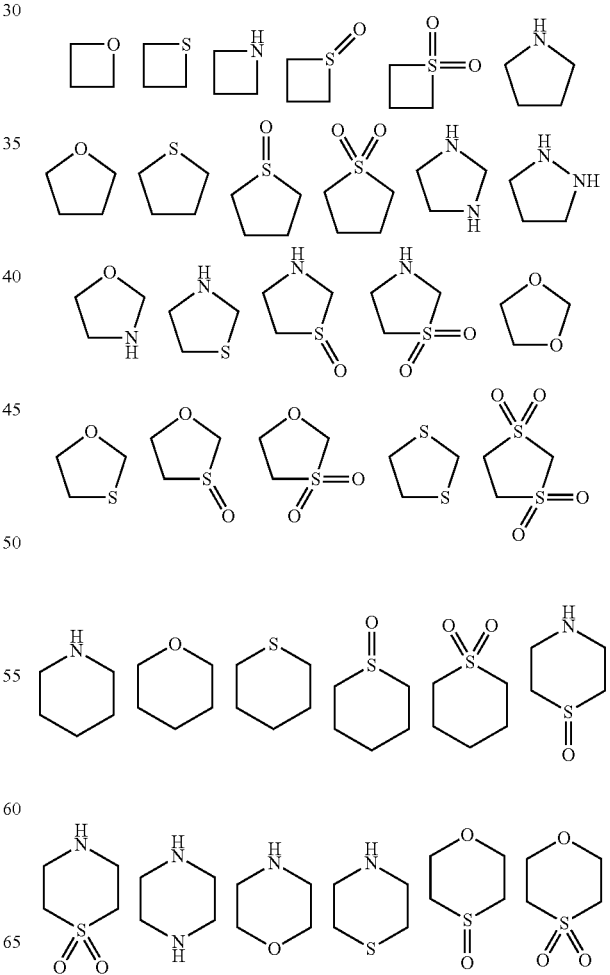

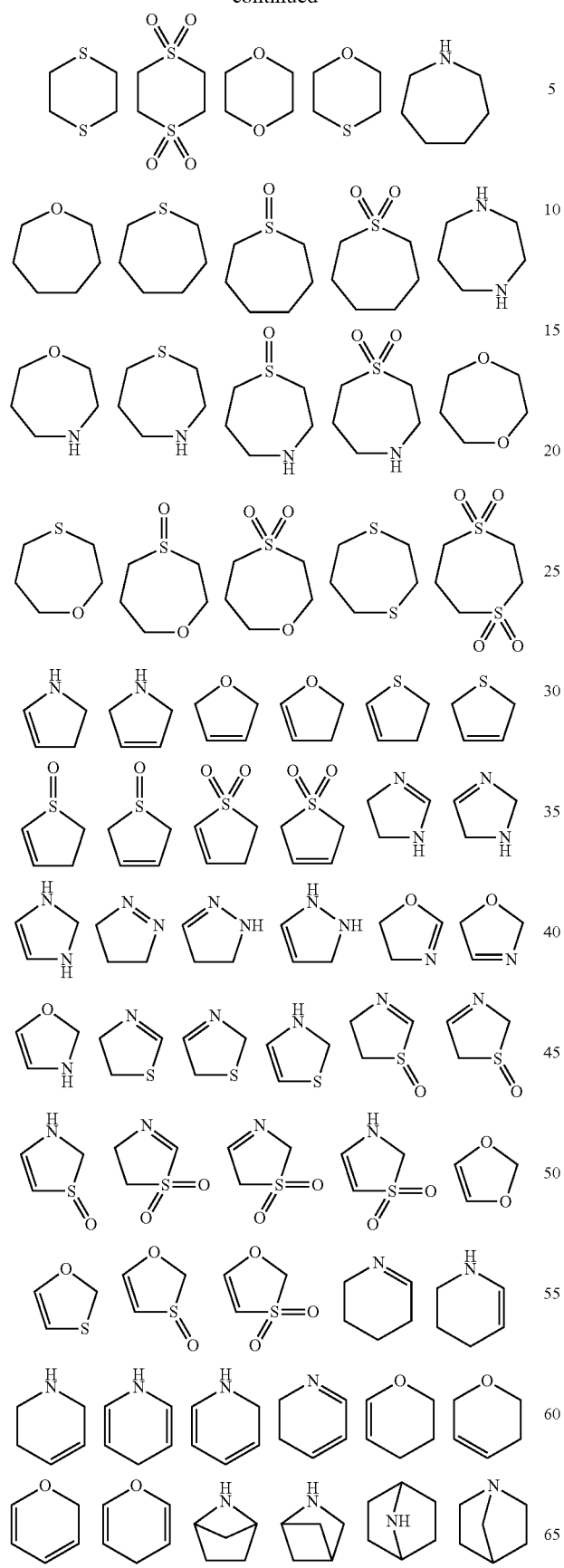
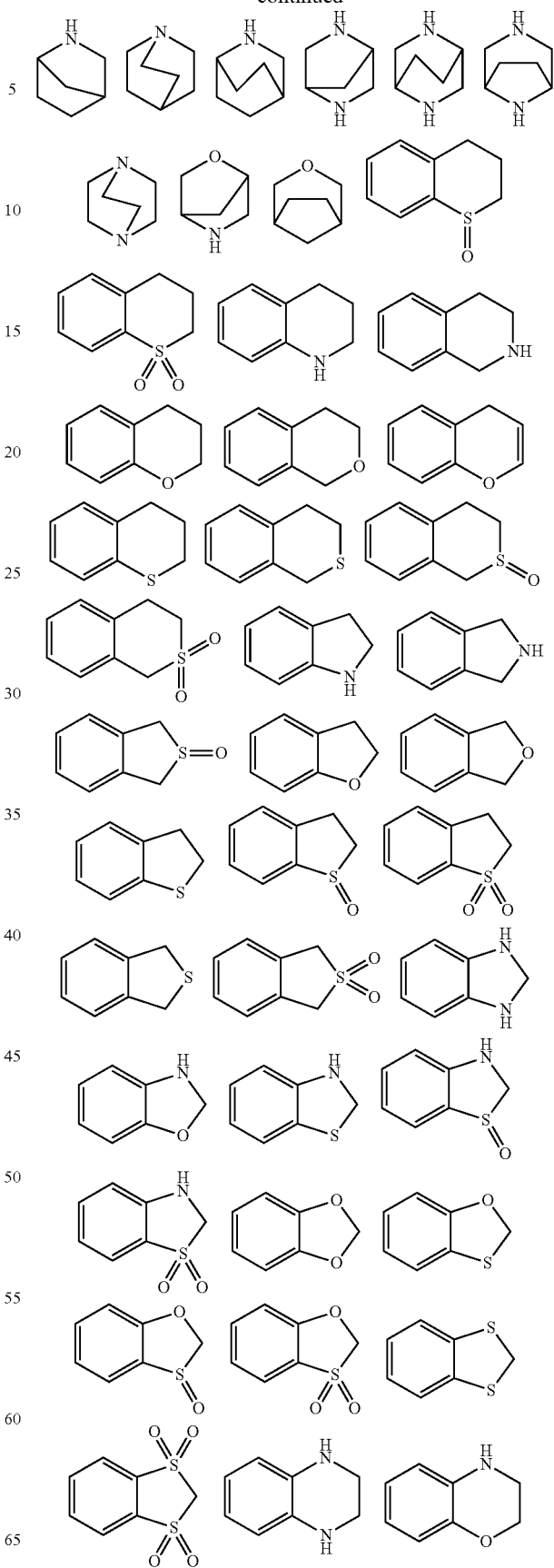

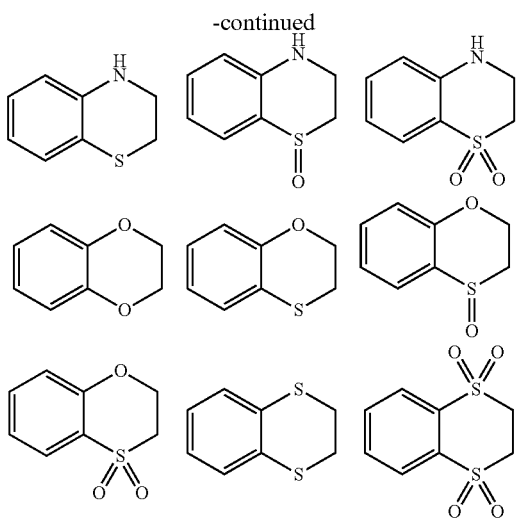

The above definition of heterocyclyl also applies if heterocyclyl is part of another (combined) group as for example in heterocyclylamino, heterocyclyloxy or heterocyclylalkyl.

If the free valency of a heterocyclyl is saturated, then a heterocyclic group is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example:

piperidinyl and

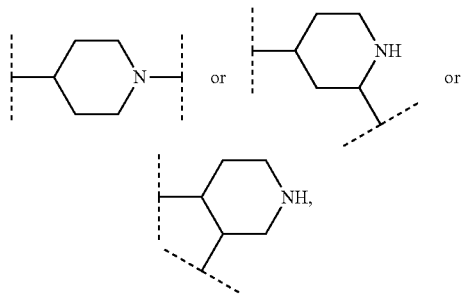

2,3-dihydro-1H-pyrrolyl and

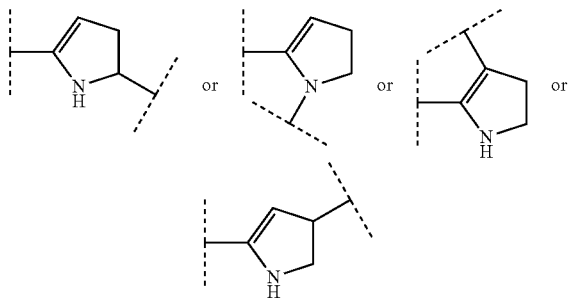

etc.

The above definition of heterocyclylene also applies if heterocyclylene is part of another (combined) group as for example in HO-heterocyclyleneamino or H₂N-heterocyclyleneoxy.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system. If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, pyrimidopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

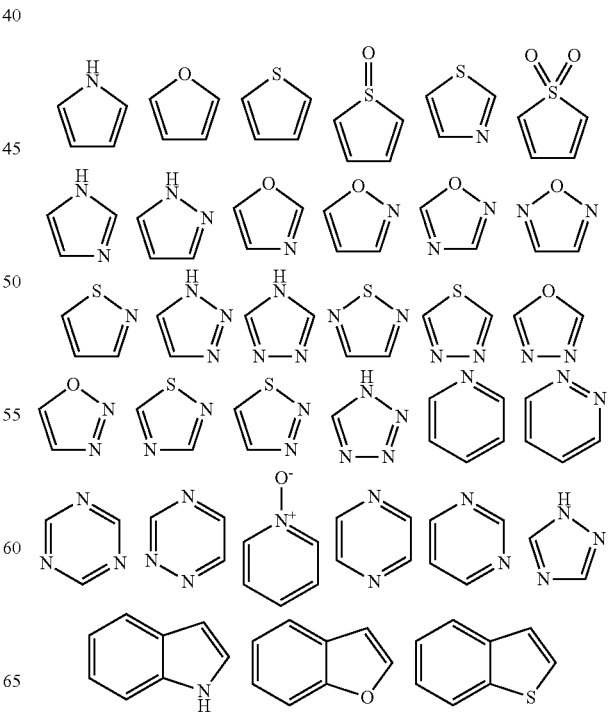

-continued

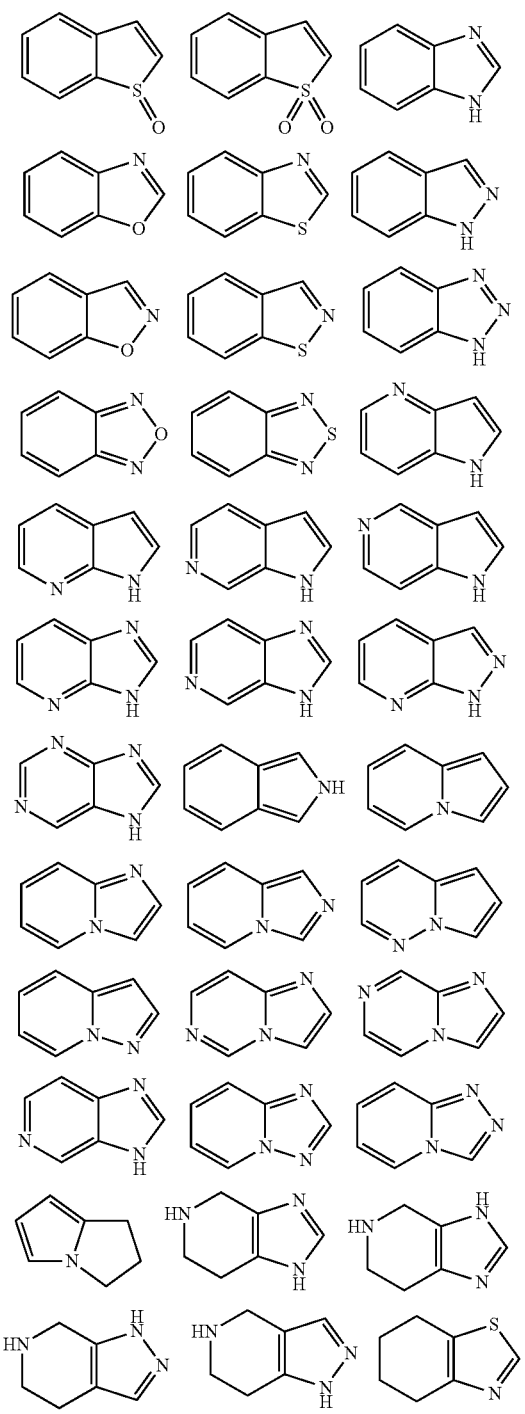

The above definition of heteroaryl also applies if heteroaryl is part of another (combined) group as for example in heteroarylamino, heteroaryloxy or heteroarylalkyl.

If the free valency of a heteroaryl is saturated, a heteroaromatic croup is obtained.

The term heteroarviene is also derived from the previously defined heteroaryl. Heteroarylene, unlike heteroaryl, is bivalent and requires two binding partners. Formally, the second valency is obtained by removing a hydrogen atom from a heteroaryl.

Corresponding groups are for example:
pyrrolyl and

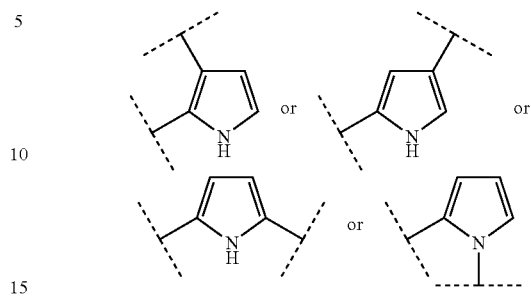

etc.

The above definition of heteroarylene also applies if heteroarylene is part of another (combined) group as for example in HO-heteroarylenamino or $H_2N$-heteroaryleneoxy.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =$N_2$ or the like, may only be substituents at carbon atoms, wherein the bivalent substituent =O may also be a substituent at sulphur. Generally, substitution may be carried out by a bivalent substituent only at ring systems and requires replacement by two geminal hydrogen atoms, i.e. hydrogen atoms that are bound to the same carbon atom that is saturated prior to the substitution. Substitution by a bivalent substituent is therefore only possible at the group —$CH_2$— or sulphur atoms of a ring system.

Stereochemistry/solvates/hydrates: Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof. The compounds and salts of the invention can exist in unsolvated as well as solvated forms with pharmaceutically acceptable solvents such as water, ethanol and the like. In general, the solvated forms such as hydrates are considered equivalent to the unsolvated forms for the purposes of the invention.

Salts: The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include acetates, ascorbates, benzenesulphonates, benzoates, besylates, bicarbonates, bitartrates, bromides/hydrobromides, Ca-edetates/edetates, camsylates, carbonates, chlorides/hydrochlorides, citrates, edisylates, ethane disulphonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulphonates, mesylates, methylbromides, methylnitrates, methylsulphates, mucates, napsylates, nitrates, oxalates, pamoates, pantothenates, phenyl acetates, phosphates/diphosphates, polygalacturonates, propionates, salicylates, stearates, subacetates, succinates, sulphamides, sulphates, tannates, tartrates, teoclates, toluenesulphonates, triethiodides, ammonium, benzathines, chloroprocaines, cholines, diethanolamines, ethylenediamines, meglumines and procaines.

Further pharmaceutically acceptable salts can be formed with cations from metals like aluminium, calcium, lithium, magnesium, potassium, sodium, zinc and the like (also see Pharmaceutical salts, Birge, S. M. et al., J. Pharm. Sci., (1977), 66, 1-19).

The pharmaceutically acceptable salts of the present invention can be synthesised from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoroacetates), also comprise a part of the invention.

Some abbreviated notations and their structure correspondences are listed below:

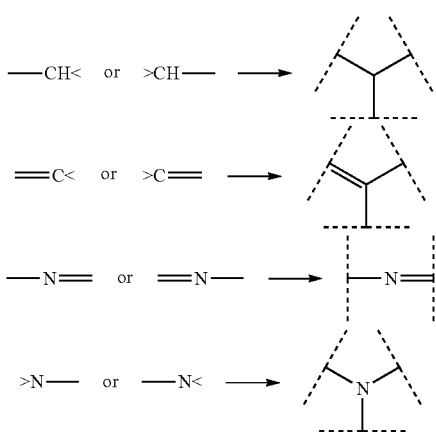

If for example in the sequence X-Y-Z the component Y is supposed to correspond to the structural section —N=, this means both X=N—Z and also X—N=Z.

In a representation such as for example

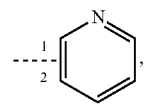

the dotted line means that the ring system may be attached to the molecule via the carbon atom 1 or 2, and is thus equivalent to the following representation

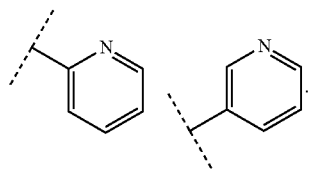

In a representation such as for example

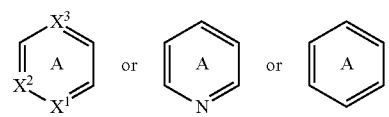

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets where necessary for clarification purposes, as in the following representations:

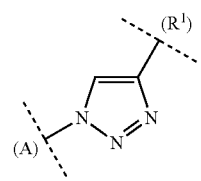

or $(R^2)$—C(O)NH— or $(R^2)$—NHC(O)—;

Groups or substituents are frequently selected from among a number of alternative groups/substituents with a corresponding group designation (e.g. $R^a$, $R^b$ etc). If such a group is used repeatedly to define a compound according to the invention in different parts of the molecule, it must always be borne in mind that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

List of Abbreviations

| | |
|---|---|
| Ac | acetyl |
| aq. | aquatic, aqueous |
| ATP | adenosine triphosphate |
| BiPh | biphenyl |
| Bn | benzyl |

-continued

| | |
|---|---|
| Boc | tert-butyloxycarbonyl |
| Bu | butyl |
| c | concentration |
| d | day(s) |
| dba | dibenzylideneacetone |
| TLC | thin layer chromatography |
| DCM | dichloromethane |
| DEA | diethylamine |
| DIPEA | N-ethyl-N,N-diisopropylamine (Hünig's base) |
| DMAP | 4-N,N-dimethylaminopyridine |
| DME | 1,2-dimethoxyethane |
| DMF | N,N-dimethylformamide |
| DMSO | dimethylsulphoxide |
| DPPA | diphenylphosphorylazide |
| dppf | 1.1'-bis(diphenylphosphino)ferrocene |
| EDTA | ethylenediaminetetraacetic acid |
| EGTA | ethyleneglycoltetraacetic acid |
| eq | equivalent(s) |
| ESI | electron spray ionization |
| Et | ethyl |
| $Et_2O$ | diethyl ether |
| EtOAc | ethyl acetate |
| EtOH | ethanol |
| h | hour |
| HATU | O-(7-azabenzotriazol-1-yl)-N,N,N',N'-tetramethyl-uronium hexafluorophosphate |
| HPLC | high performance liquid chromatography |
| i | iso |
| Kat., kat. | catalyst, catalytic |
| conc. | concentrated |
| LC | liquid chromatography |
| sln. | solution |
| Me | methyl |
| MeOH | methanol |
| min | minutes |
| MPLC | medium pressure liquid chromatography |
| MS | mass spectrometry |
| NBS | N-Bromo-succinimide |
| NMM | N-methylmorpholine |
| NMP | N-methylpyrrolidone |
| NP | normal phase |
| n.a. | not available |
| PBS | phosphate-buffered saline |
| Ph | phenyl |
| Pr | propyl |
| Py | pyridine |
| rac | racemic |
| red. | reduction |
| $R_f$(Rf) | retention factor |
| RP | reversed phase |
| rt | ambient temperature |
| $S_N$ | nucleophilic substitution |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | triethylamine |
| temp. | temperature |
| tert | tertiary |
| Tf | triflate |
| TFA | trifluoroacetic acid |
| THF | tetrahydrofuran |
| TMS | trimethylsilyl |
| $t_{Ret.}$ | retention time (HPLC) |
| TRIS | tris(hydroxymethyl)-aminomethane |
| TsOH | p-toluenesulphonic acid |
| UV | ultraviolet |

Features and advantages of the present invention will become apparent from the following detailed examples which illustrate the fundamentals of the invention by way of example without restricting its scope:

PREPARATION OF THE COMPOUNDS ACCORDING TO THE INVENTION

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with CAS rules using the software Autonom (Beilstein).

Microwave reactions are carried out in an initiator/reactor made by Biotage or in an Explorer made by CEM in sealed containers (preferably 2, 5 or 20 mL), preferably with stirring.

Chromatography

For preparative medium pressure chromatography (MPLC) silica gel made by Millipore (name: Granula Silica Si-60A 35-70 µm, NP phase) or C-18 RP-silica gel (RP-phase) made by Macherey Nagel (name: Polygoprep 100-50 C18) is used.

Automated normal phase chromatography is also carried out on a CombiFlash Companion XL apparatus in combination with a CombiFlash Foxy 200 fraction collector or a CombiFlash Companion Rf apparatus made by Isco. For this, commercially obtainable RediSepRf (120 g silica gel) one-way columns are used. Furthermore, automated normal phase chromatography can also be carried out on an Isolera Flash Purification apparatus made by Biotage. For this, commercially obtainable one-way SNAP-Cartridges (e.g. 50 g silica gel) are used.

The thin layer chromatography is carried out on ready-made silica gel 60 TLC plates on glass (with fluorescence indicator F-254) made by Merck.

The preparative high pressure chromatography (RP HPLC) of the example compounds according to the invention is carried out with columns made by Waters (names: XTerra Prep. MS C18, 5 µm, 30×100 mm or XTerra Prep. MS C18, 5 µm, 50×100 mm OBD or Symmetrie C18, 5 µm, 19×100 mm or Sunfire C18 OBD, 19×100 mm, 5 µm or Sunfire Prep C 10 µm OBD 50×150 mm or X-Bridge Prep C18 5 µm OBD 19×50 mm) or X-Bridge Prep C18 10 µm OBD 50×150 mm), Agilent (name: Zorbax SB-C8 5 µm PrepHT 21.2×50 mm) and Phenomenex (names: Gemini C18 5 µm AXIA 21.2×50 mm or Gemini C18 10 µm 50×150 mm). Different gradients of $H_2O$/acetonitrile or $H_2O$/MeOH are used to elute the compounds, while 0.1% HCOOH is added to the water (acidic conditions). For the chromatography under basic conditions $H_2O$/acetonitrile gradients are used as well, while the water is made alkaline as follows: 5 mL $NH_4HCO_3$ solution (158 g in 1 L $H_2O$) and 2 mL $NH_3$ (7 M in MeOH) are replenished to 1 L with $H_2O$.

The preparative high pressure chromatography on normal phase (NP HPLC) of the example compounds according to the invention is carried out with columns made by Macherey & Nagel (name: Nucleosil, 50-7, 40×250 mm) and VDSoptilab (name: Kromasil 100 $NH_2$, 10 µM, 50×250 mm). Different gradients of DCM/MeOH are used to elute the compounds, while 0.1% $NH_3$ is added to the MeOH.

The analytical HPLC (reaction control) of intermediate compounds is carried out using columns made by Agilent (names: Zorbax SB-C8, 5 µm, 21.2×50 mm or Zorbax SB-$C_8$-3.5 µm 2.1×50 mm) and Phenomenex (name: Gemini C18 3 µm 2×30 mm). The analytical equipment is also equipped with a mass detector in each case.

HPLC-Mass Spectroscopy/UV-Spectrometry

The retention times/MS-ESL for characterizing the example compounds according to the invention are produced using an HPLC-MS apparatus (high performance liquid chromatography with mass detector). Compounds that elute at the injection peak are given the retention time $t_{Ret.}$=0.00.

HPLC-MS Method A
HPLC: Agilent 1100 Series
MS: Agilent LC/MSD SL
Column: Waters, XBridge™ C18, 2.5 µm, 2.1×20 mm (Part. No. 186003201)
Eluent: A: 0.1% $NH_3$ (=pH 9-10)
 B: Acetonitrile HPLC grade
Detection: MS: Positive and negative mode
Mass Range: 120-800 m/z
Flow: 1.00 mL/min
Column temperature: 60° C.
Gradient: 0.00 min 5% B
 0.00-2.50 min 5%→95% B
 2.51-2.80 min 95% B
 2.81-3.10 min 95%→5% B The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

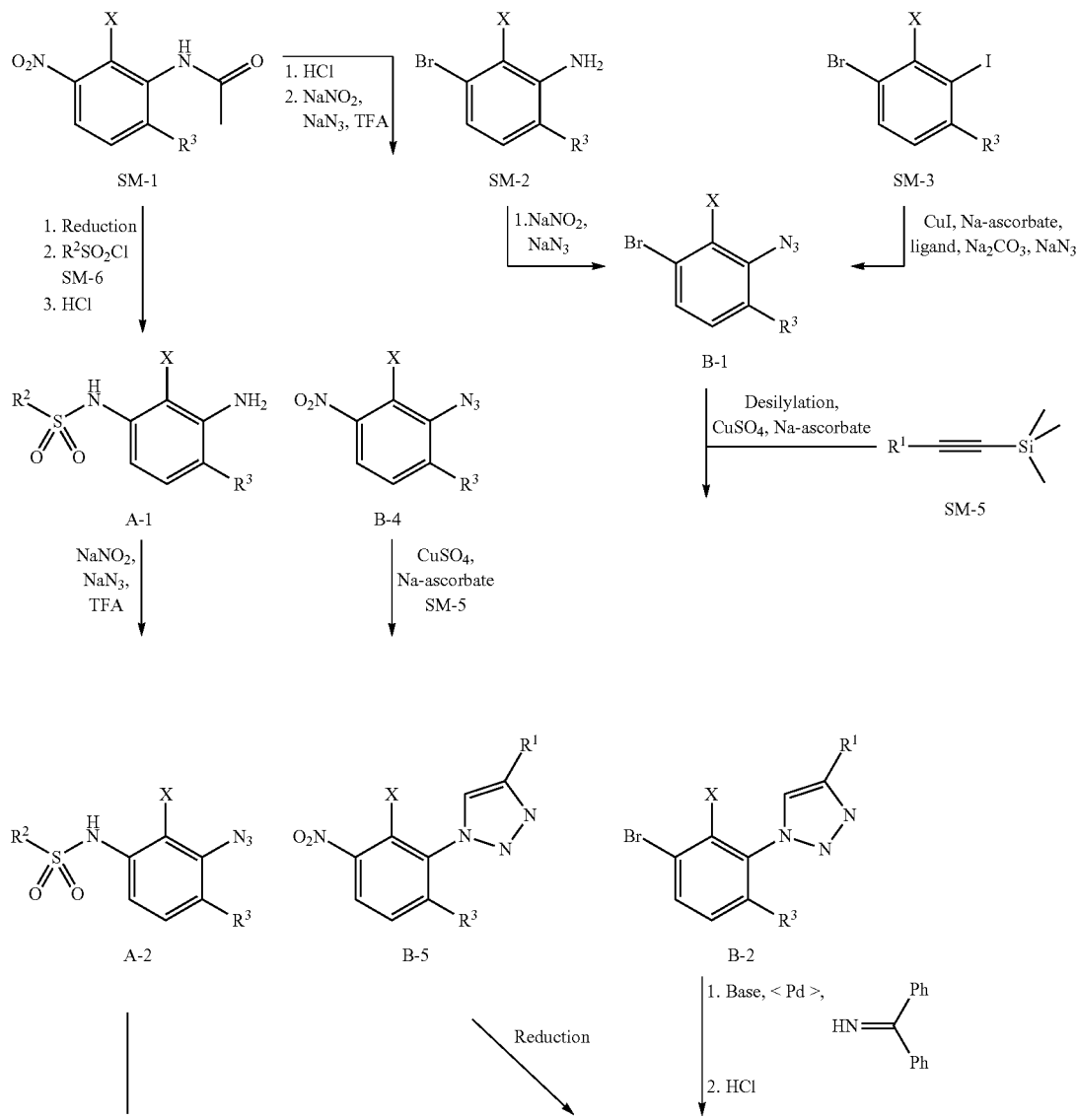

Scheme 1a: General synthetic routes towards compounds (I)

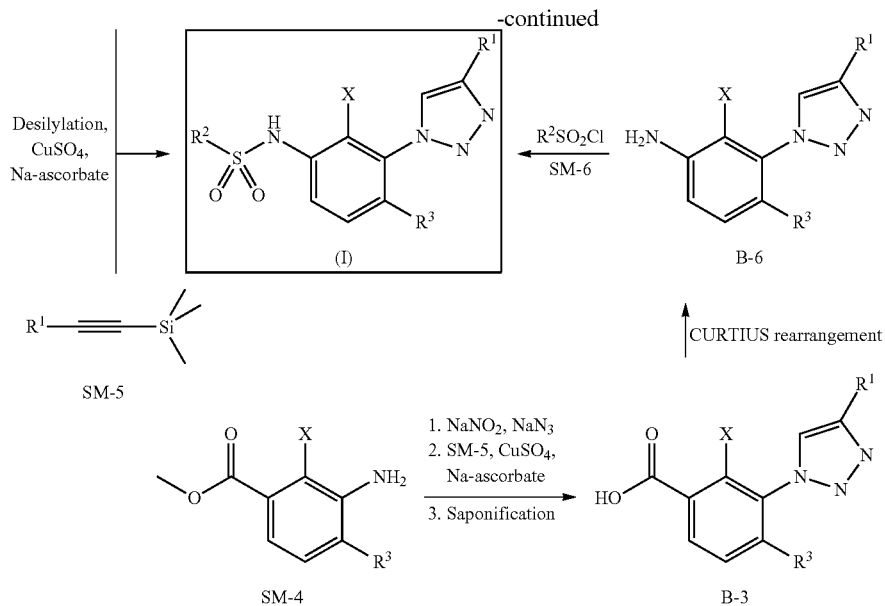

Compounds (I) according to the invention can be prepared in several ways as described in the general reaction scheme 1a starting from starting materials SM-1 to SM-6 which are either commercially available or can be synthesized as described below.

Compounds (I) can be prepared via a copper catalyzed [2+3] cyloaddition reaction of azides A-2 with deprotected alkynes SM-5. The azides A-2 can be obtained starting from the corresponding anilines A-1 via diazotation with $NaNO_2$ and azide formation with $NaN_3$ in TFA. The amines A-1 are made from nitro compounds SM-1 via reduction of the nitro function, sulfone amide formation with sulfonic acid chlorides or sulfamoyl chlorides SM-6 and subsequent deprotection of the amino function with e.g. aqueous HCl.

Following an alternative route compounds (I) can be prepared from the anilines B-6 and the sulfonic acide chlorides or sulfamoyl chlorides SM-6:

The anilines B-6 can be either prepared starting from the nitro compounds SM-1 which are deprotected, transformed to the azides B-4, subsequently cyclized to the triazoles B-5 and finally reduced. Alternatively, the anilines B-6 are prepared from bromo compounds B-2 via a palladium catalyzed amination reaction with benzophenone imine followed by deprotection under acidic conditions. The bromo compounds B-2 in turn are synthesized via a copper catalyzed [2+3] cycloaddition reaction starting from the deprotected alkynes SM-5 and the azides B-1 which in turn can be prepared either from the amino compounds SM-2 through diazotation with subsequent azide formation or from the iodo compounds SM-3 through copper catalyzed azide formation. In a third alternative the anilines B-6 are prepared from the corresponding benzoic acids B-3 via a CURTIUS degradation. The benzoic acids B-3 can be prepared from the benzoic acid esters SM-4 via azide formation, copper catalyzed [2+3] cycloaddition reaction followed by ester cleavage.

The group $R^1$ in final compounds (I) according to the invention as depicted in scheme 1a has structure

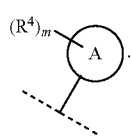

Compounds (I) which are directly synthesized following one of the synthetic routes depicted in scheme 1a and which carry functional groups, either in $R^1$ or $R^2$, that can be further modified such as e.g. halogen atoms, amino and hydroxy groups (including cyclic amines), carboxylic acid or ester functions, nitrils etc. can be optionally derivatized to further compounds (I) by well established organic chemical transformations such as palladium-catalyzed cross coupling reactions, acylation, amidation, addition, reduction or (reductive) alkylation. These additional steps are not depicted in scheme 1a (see however schemes 1b to 1e).

Likewise, it is also possible to include these additional steps in the synthetic routes depicted in scheme 1a, i.e. to carry out derivatization reactions with intermediate compounds.

In addition, it may also be possible that building blocks bearing protecting groups are used, i.e. further steps for deprotection are necessary.

Scheme 1b: Derivatization of compounds (I) of sort (I)$^a$ by BUCHWALD-HARTWIG cross coupling reaction

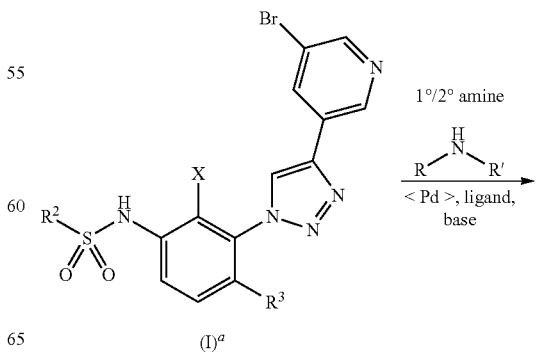

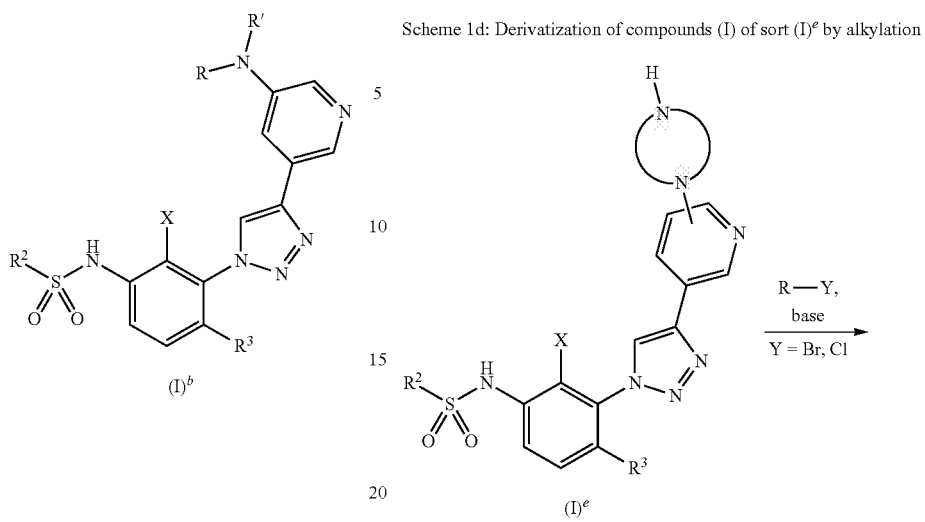
Scheme 1d: Derivatization of compounds (I) of sort (I)$^e$ by alkylation
Scheme 1c: Derivatization of compounds (I) of sort (I)$^c$ by acylation
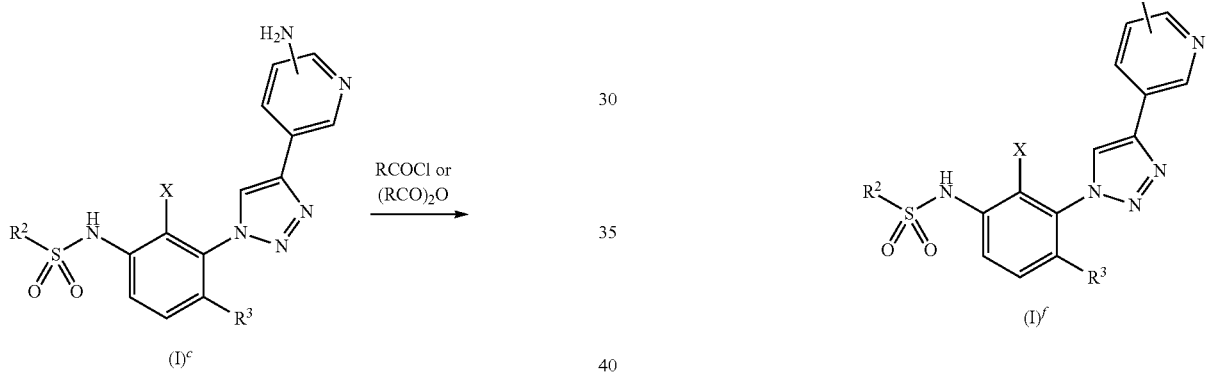
Scheme 1e: Derivatization of compounds (I) of sort (I)$^e$ by reductive amination
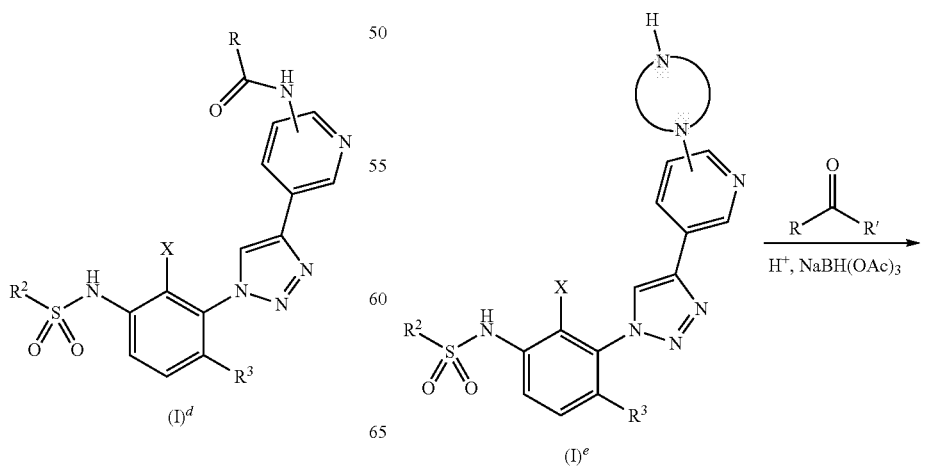

-continued

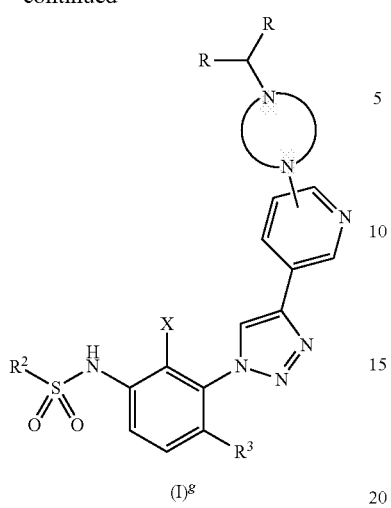

(I)<sup>g</sup>

A. Synthesis of Starting Materials

A.1. Synthesis of SM-1
A.1.1. Experimental Procedure for the Synthesis of SM-1a

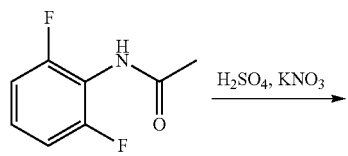

2,6-Difluoroacetanilide (4.00 g, 23.4 mmol) is taken-up in concentrated $H_2SO_4$ (10 mL) and cooled to −10° C. $KNO_3$ (4.73 g, 46.7 mmol) is added in small portions with stirring. After complete addition the cooling bath is removed, the mixture is slowly warmed to rt and stirred for 2 h. The reaction mixture is poured into ice water. The resulting precipitate is filtered off and dried in vacuo to give SM-1a (HPLC-MS: $t_{Ret.}$=0.50 min; MS (M+H)$^+$=215) which is used without further purification.

A.1.2. Experimental Procedure for the Synthesis of SM-1b

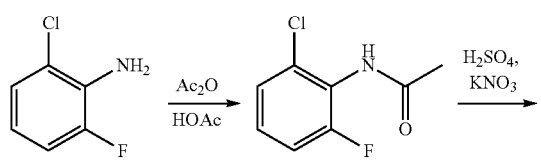

-continued

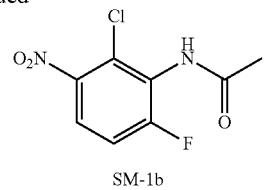

Step 1
To 2-chloro-6-fluoroaniline (24.8 g, 165 mmol) in HOAc (90 mL) is added $Ac_2O$ (18 mL, 189 mmol) and the mixture is stirred at 90° C. for 1 h. After cooling to rt $H_2O$ is added and the mixture is neutralized with 2 M NaOH solution with stirring. The aqueous layer is extracted twice with DCM. The combined organic layer is washed with semi-saturated $NaHCO_3$ solution and brine, dried over $MgSO_4$ and evaporated to give the acetanilide which is used without further purification.
Step 2
The acetanilide (31.0 g, 165 mmol) is taken-up in conc. $H_2SO_4$ (70 mL) and cooled to 0° C. $HNO_3$ (11.4 mL, 166 mmol) is added and the mixture is allowed to warm to rt overnight. $H_2O$ (cooled with ice) is added slowly and the resulting mixture is extracted twice with DCM. The combined organic layer is washed with semi-saturated $NaHCO_3$ solution and brine, dried over $MgSO_4$ and evaporated to give a mixture of SM-1b and its regioisomer. The crude material is recrystallized from MeCN to give pure SM-1b (HPLC-MS: $t_{Ret.}$=0.56 min; MS (M+H)$^+$=233).

A.2. Synthesis of SM-2
A.2.1 Experimental Procedure for the Synthesis of SM-2a

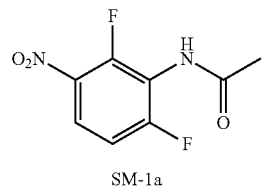

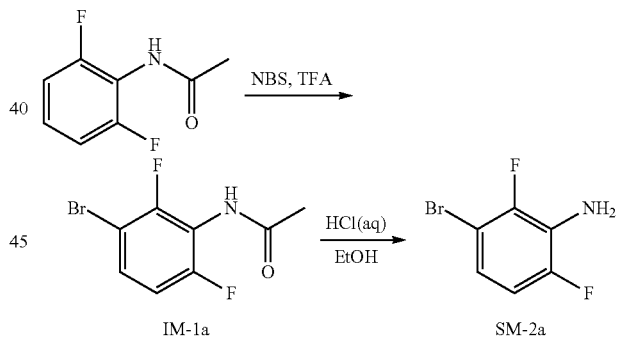

Step 1
2,6-difluoro-acetanilide (3.02 g, 17.3 mmol) is taken-up in TFA (15 mL) and conc. $H_2SO_4$ (20 mL). NBS (3.20 g, 17.9 mmol) is added in small portions and the resulting mixture is stirred at rt overnight. The reaction mixture is poured into ice water and the resulting precipitate is collected by filtration, washed with $H_2O$ and dried in vacuo to give the bromide IM-1a (HPLC-MS: $t_{Ret.}$=0.79 min; MS (M+H)$^+$=250/252) which is used without further purification.
Step 2
The bromide IM-1a (3.60 g, 14.4 mmol) is taken-up in EtOH (10 mL), conc. HCl (10 mL) is added and the mixture stirred at 70° C. for 18 h. After cooling to rt EtOH is evaporated whereupon a precipitate is formed which is collected by filtration and air-dried to give aniline SM-2a (HPLC-MS: $t_{Ret.}$=1.11 min; MS (M+H)$^+$=208/210) which is used without further purification.

A.3. Synthesis of SM-5

Scheme 2: General synthetic routes to alkynes for [2 + 3] cycloaddition

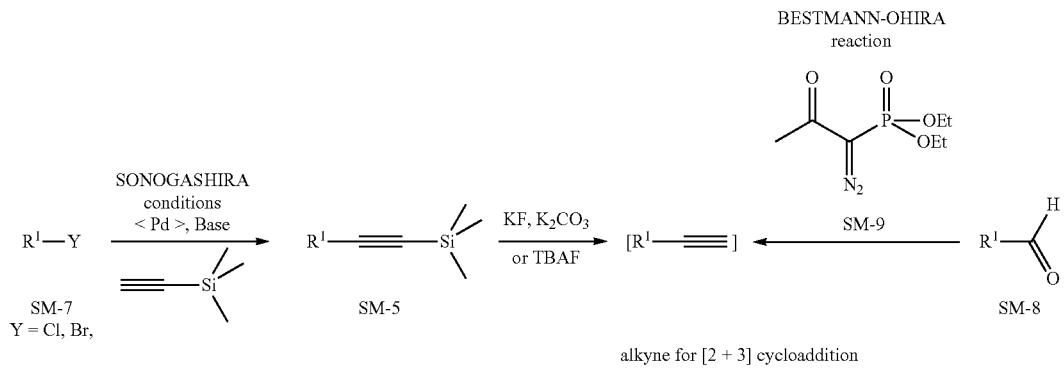

alkyne for [2 + 3] cycloaddition

All alkynes for [2+3] cycloaddition which are described and utilized in the present invention are either commercially available or can be synthesized as shown in scheme 2 starting from the corresponding halogen precursors SM-7 via a palladium-catalyzed SONOGASHIRA cross coupling reaction with subsequent silyl deprotection with KF, $K_2CO_3$ or TBAF or starting from the aldehydes SM-8 via a BESTMANN-OHIRA reaction using the diazophosphonate SM-9.

The reagent which is actually used for [2+3] cycloaddition, the free or deprotected alkyne, is usually generated in situ and directly converted to the corresponding triazoles. However, in some cases the silyl protected alkyne SM-5 is deprotected and used in isolated form for [2+3] cycloaddition.

A.3.1. Experimental Procedure for the Synthesis of alkyne SM-5a

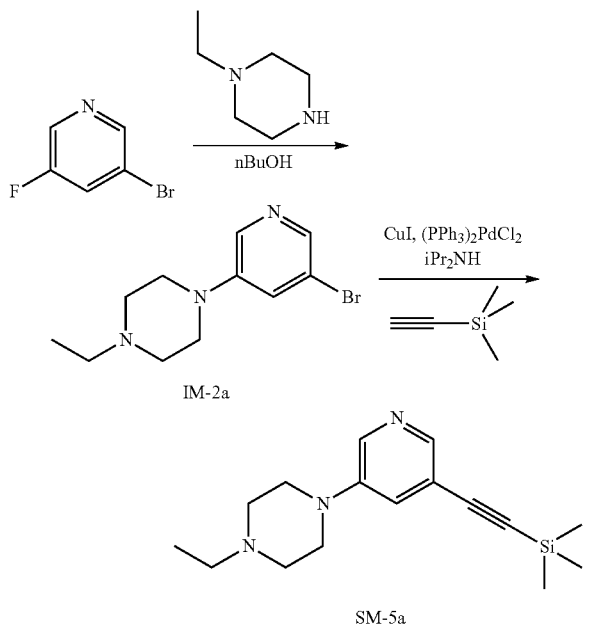

Step 1

3-Fluoro-5-bromo pyridine (998 mg, 5.50 mmol) and N-ethyl piperazine (1.9 mL, 14.7 mmol) are taken-up in n-BuOH (4 mL) and stirred at 100° C. for 6 d. The reaction mixture is acidified with 0.1 N hydrochloric acid and extracted 3× with EtOAc. The water layer is made alkaline and extracted 3× with DCM. The combined organic layer is dried over $MgSO_4$, filtered and evaporated to give IM-2a (HPLC-MS: $t_{Ret.}$=1.40 min; MS $(M+H)^+$=270) which is used without further purification.

Step 2

IM-2a (1.06 g, 3.52 mmol), CuI (60.9 mg, 0.32 mmol) and $Pd(PPh_3)_2Cl_2$ (55.5 mg, 0.08 mmol) are taken-up in N,N-diisopropylamine (2.0 mL). TMS-acetylene (750 µL, 5.31 mmol) is added and the mixture is stirred for 30 min at 100° C. After cooling to rt the pH is adjusted with 8 N hydrochloric acid to pH 4. The reaction mixture is extracted 3× with DCM and the combined organic layer is dried over $MgSO_4$, filtered and evaporated to give SM-5a (HPLC-MS: $t_{Ret.}$=2.00 min; MS $(M+H)^+$=288) which is used without further purification.

A.3.2. Experimental Procedure for the Aynthesis of alkyne SM-5b

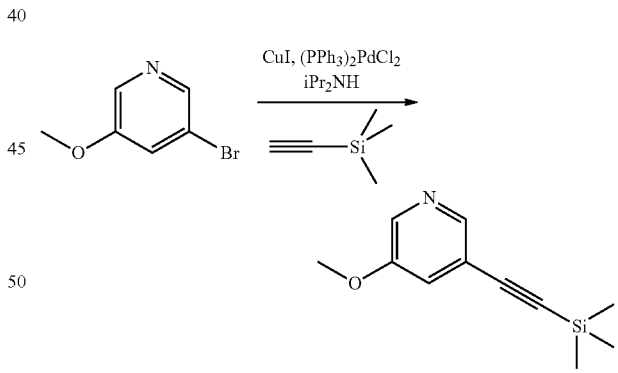

To a suspension of 3-bromo-5-methoxy-pyridine (1.15 g, 6.09 mmol), CuI (29.0 mg, 0.15 mmol) and $Pd(PPh_3)_2Cl_2$ (107 mg, 0.15 mmol) in N,N-diisopropylamine (2.6 mL) is added TMS-acetylene (947 µL, 6.70 mmol) under an inert atmosphere and the mixture is stirred at 70° C. for 1 h. After re-cooling MeCN is added, the mixture is filtered and evaporated. The residue is taken-up in HCl (1 N) and extracted 3× with DCM. The combined organic layer is dried over $Na_2SO_4$, filtered and evaporated. The residue is purified by Kugelrohr distillation to give SM-5b (HPLC-MS: $t_{Ret.}$=2.21 min; MS $(M+H)^+$=206).

A.3.3. Experimental Procedure for the Synthesis of Alkyne SM-5C

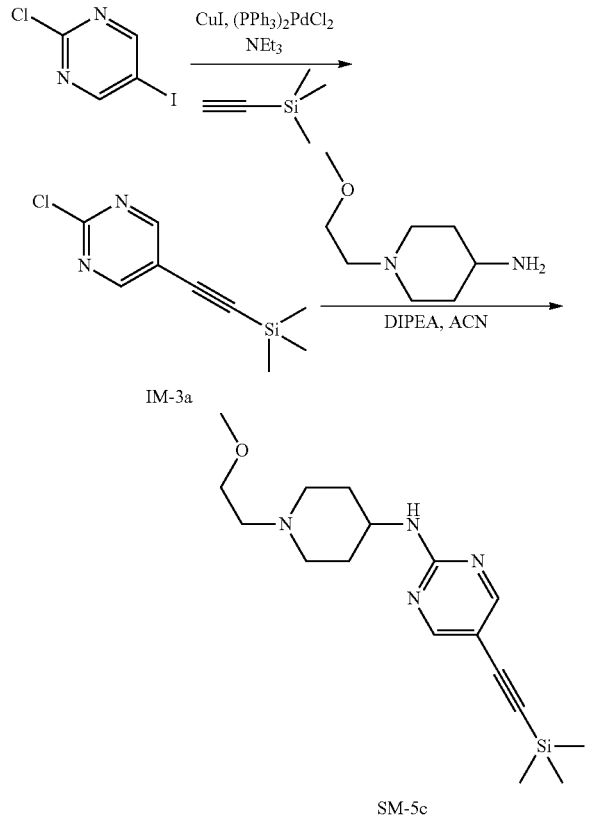

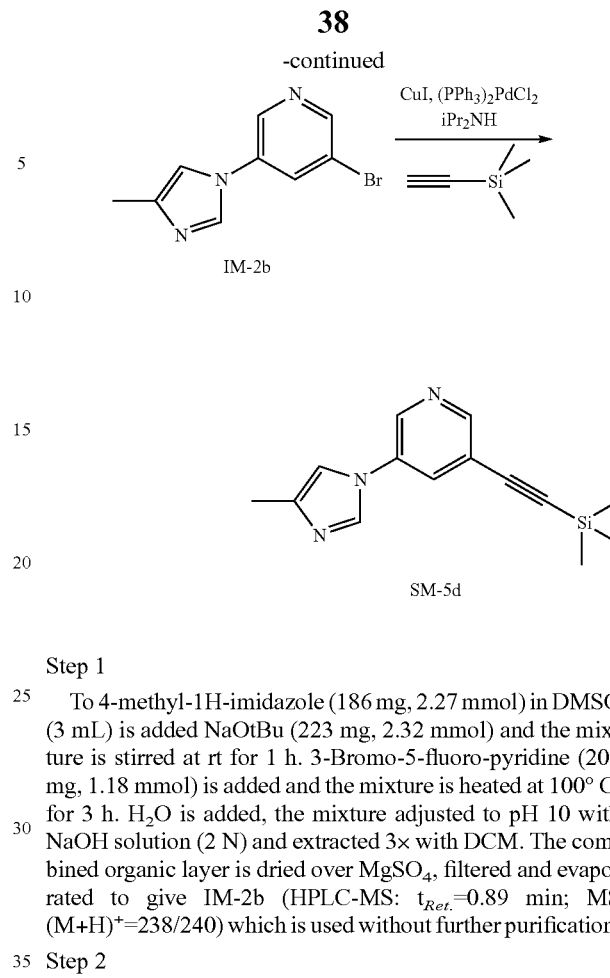

2-chloro-5-iodo-pyrimidine (513 mg, 2.14 mmol), CuI (13.3 mg, 0.07 mmol) and (PPh$_3$)$_2$PdCl$_2$ (40.7 mg, 0.06 mmol) are taken-up in dry THF (10 mL). NEt$_3$ (0.57 mL, 4.05 mmol) and TMS-acetylene (0.42 mL, 2.91 mmol) are added and the mixture is stirred at 50° C. overnight. The mixture is diluted with THF, filtered over Celite™ and evaporated. The residue is taken-up in water and extracted 3× with EtOAc. The combined organic layer is dried over MgSO$_4$, filtered and evaporated. The residual IM-3a (HPLC-MS: $t_{Ret.}$=2.06 min; MS (M+H)$^+$=211) is used without further purification.

IM-3a (400 mg, 1.90 mmol) is taken-up in MeCN (6 mL). 1-(2-Methoxy-ethyl)-piperidin-4-yl-amine (474 mg, 2.99 mmol) and DIPEA (0.5 mL, 2.93 mmol) are added, the vial is sealed and heated to 60° C. overnight until LC-MS indicates complete conversion. The reaction mixture containing SM-5c (HPLC-MS: $t_{Ret.}$=1.99 min; MS (M+H)$^+$=333) is directly used in the next step (deprotection and cyloaddition reaction).

A.3.4 Experimental procedure for the synthesis of alkyne SM-5d

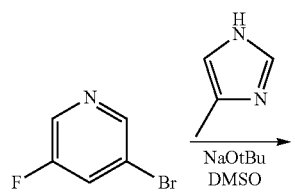

Step 1

To 4-methyl-1H-imidazole (186 mg, 2.27 mmol) in DMSO (3 mL) is added NaOtBu (223 mg, 2.32 mmol) and the mixture is stirred at rt for 1 h. 3-Bromo-5-fluoro-pyridine (208 mg, 1.18 mmol) is added and the mixture is heated at 100° C. for 3 h. H$_2$O is added, the mixture adjusted to pH 10 with NaOH solution (2 N) and extracted 3× with DCM. The combined organic layer is dried over MgSO$_4$, filtered and evaporated to give IM-2b (HPLC-MS: $t_{Ret.}$=0.89 min; MS (M+H)$^+$=238/240) which is used without further purification.

Step 2

IM-2b (280 mg, 1.18 mmol), CuI (25.2 mg, 0.13 mmol) and Pd(PPh$_3$)$_2$Cl$_2$ (41.7 mg, 0.06 mmol) are taken-up in N,N-diisopropylamine (1.7 mL). TMS-acetylene (332 μL, 2.35 mmol) is added and the mixture is stirred at 60° C. overnight. After cooling to rt DCM is added and the organic phase is extracted 2× with 1 N hydrochloric acid. The combined aqueous layer is adjusted to pH 10 with 1 N NaOH solution and extracted 3× with DCM. The combined organic layer is filtered, dried over Na$_2$SO$_4$, filtered again and evaporated to give SM-5d which is used without further purification. SM-5d can optionally be purified by RP HPLC to eliminate minor amounts of the imidazole regioisomer formed during the nucleophilic substitution reaction.

A.3.5. Experimental Procedure for the Synthesis of Alkyne SM-5e

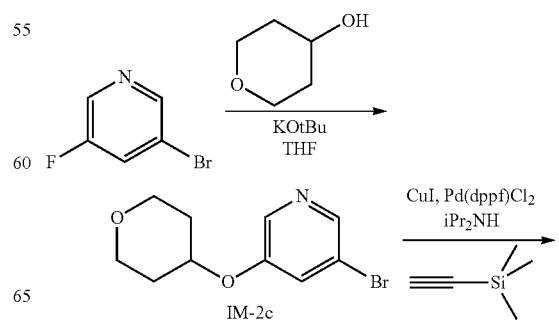

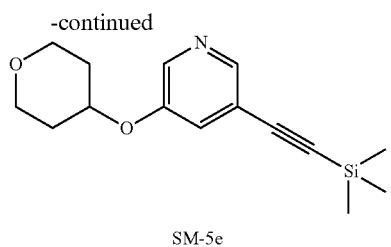

SM-5e

Step 1

To tetrahydro-4H-pyran-4-ol (534 mg, 5.23 mmol) in THF (5 mL) is added KOtBu (881 mg, 7.85 mmol) and the mixture is stirred at rt for 20 min. 3-Bromo-5-fluoro-pyridine (922 mg, 5.24 mmol) is added and the mixture stirred at rt overnight. $H_2O$ is added and the reaction mixture is extracted 3× with EtOAc. The combined organic layer is dried over $MgSO_4$, filtered and evaporated to give IM-2c (HPLC-MS: $t_{Ret.}$=1.07 min; MS $(M+H)^+$=258/260) which is used without further purification.

Step 2

To IM-2c (600 mg, 2.32 mmol), CuI (19.2 mg, 0.10 mmol) and Pd(dppf)Cl$_2$ (63.4 mg, 0.08 mmol) in THF (4 mL) is added N,N-diisopropylamine (2.5 mL) and after 5 min TMS-acetylene (750 μL, 5.35 mmol) under an inert atmosphere. The resulting mixture is stirred at 90° C. for 16 h. The reaction mixture is filtered and SM-5e is used as solution for the next step.

A.3.6. Experimental Procedure for the Synthesis of Alkyne SM-5f

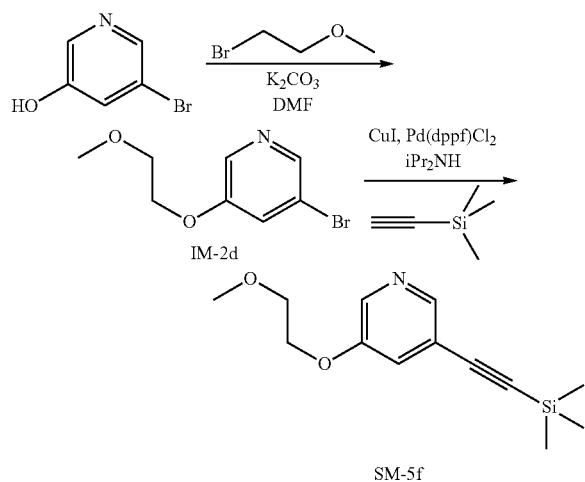

SM-5f

Step 1

To 3-bromo-5-hydroxy-pyridine (198 mg, 1.71 mmol) in DMF (7 mL) is added $K_2CO_3$ (335 mg, 2.44 mmol) and the mixture is stirred at 50° C. for 72 h. The reaction mixture is filtered and purified by RP MPLC. The product containing fractions are pooled, MeCN is evaporated and the aqueous residue is extracted 3× with DCM. The combined organic layer is dried over MgSO$_4$, filtered and evaporated to give IM-2d (HPLC-MS: $t_{Ret.}$=0.95 min; MS $(M+H)^+$=232/234).

Step 2

To IM-2d (100 mg, 0.43 mmol), CuI (4.70 mg, 0.03 mmol) and Pd(dppf)Cl$_2$ (13.0 mg, 0.02 mmol) in THF (3 mL) is added N,N-diisopropylamine (550 μL) and after 5 min TMS-acetylene (125 μL, 0.89 mmol) under an inert atmosphere. The resulting mixture is stirred at 90° C. for 16 h. The reaction mixture is filtered and SM-5f is used as solution for the next step.

A.3.7. Experimental Procedure for the Synthesis of Alkyne SM-5g

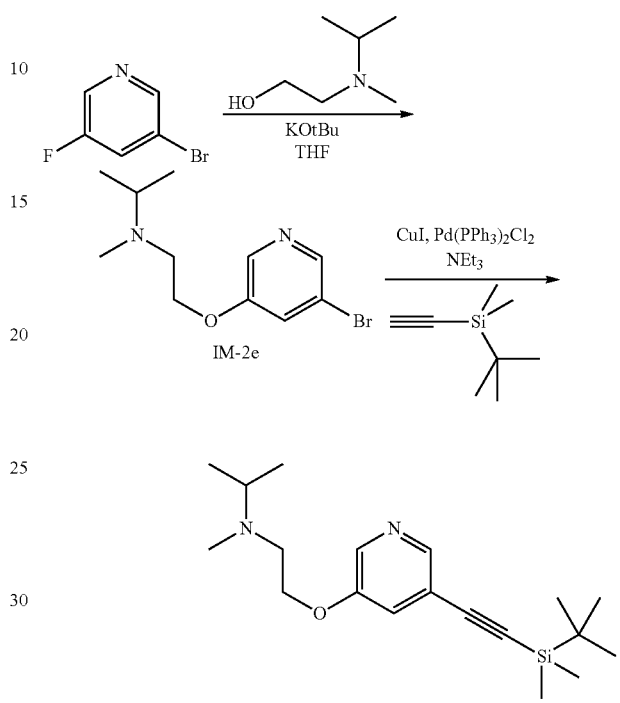

SM-5g

Step 1

To 2-(N-methyl-N-isopropylamino)-ethanol (2.00 g, 11.4 mmol) in THF (10 mL) is added KOtBu (1.91 g, 17.0 mmol) and the mixture is stirred at rt for 20 min. 3-Bromo-5-fluoro-pyridine (2.00 g, 11.4 mmol) is added and the mixture stirred at rt overnight. $H_2O$ is added and the reaction mixture is extracted 3× with EtOAc. The combined organic layer is dried over MgSO$_4$, filtered and evaporated to give IM-2e which is used without further purification.

Step 2

Under an inert atmosphere IM-2e (3.10 g, 11.4 mmol) is taken-up in EtOAc (20 mL). NEt$_3$ (13 mL), CuI (64.8 mg, 0.34 mmol), Pd(PPh$_3$)$_2$Cl$_2$ (239 mg, 0.34 mmol) and TBDMS-acetylene (4.0 mL, 28.4 mmol) is added and the mixture is stirred at 60° C. for 5 h. The reaction mixture is diluted with EtOAc, filtered and evaporated. The residue is taken-up in DCM and purified by flash chromatography using DCM/MeOH (9:1) as eluent. The product containing fractions of SM-5g (HPLC-MS: $t_{Ret.}$=2.45 min; MS $(M+H)^+$=333) are evaporated.

Analogously to the procedures described under A.3.1. to A.3.7. above additional alkynes SM-5 can be prepared using various amines, bromo or iodo aryls and silyl protected acetylenes. Most of the alkynes can be used without further purification. In order to obtain higher purity of the silyl protected alkynes either Kugelrohr distillation or flash chromatography using different gradients of cyclohexane/EtOAc as eluent can be used.

TABLE 1

| # | structure | $t_{Ret.}$ (HPLC) [min] | MS (M + H)+ |
|---|---|---|---|
| SM-5a | 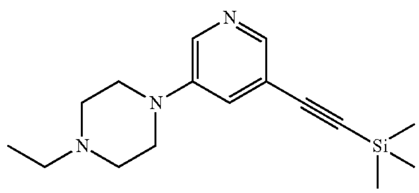 [SMILES: CCN1CCN(c2cncc(C#C[Si](C)(C)C)c2)CC1] | 2.00 | 288 |
| SM-5b | 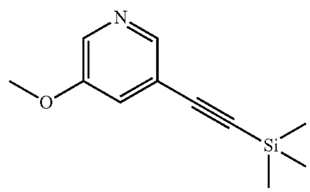 | 2.21 | 206 |
| SM-5c | 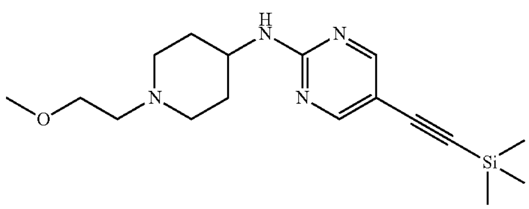 | 1.99 | 333 |
| SM-5d | 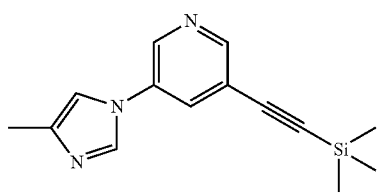 | n.d. | 256 |
| SM-5e | 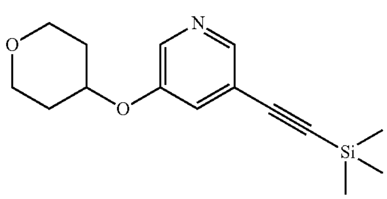 [SMILES: C[Si](C)(C)C#Cc1cncc(OC2CCOCC2)c1] | n.d. | 276 |
| SM-5f | 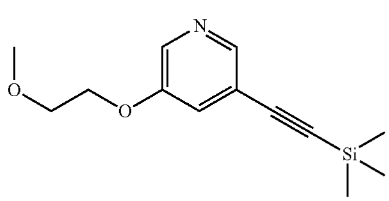 | n.d. | 233 |
| SM-5g | 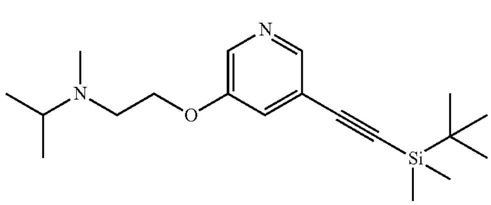 [SMILES: CC(C)N(C)CCOc1cncc(C#C[Si](C)(C)C(C)(C)C)c1] | 2.45 | 333 |

TABLE 1-continued
Silyl-protected alkynes SM-5
| # | structure | $t_{Ret.}$ (HPLC) [min] | MS (M + H)+ |
|---|---|---|---|
| SM-5h | 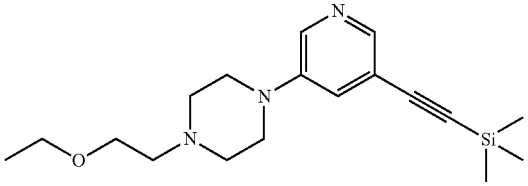 [SMILES: CCOCCN1CCN(c2cncc(C#C[Si](C)(C)C)c2)CC1] | 2.04 | 332 |
| SM-5i | 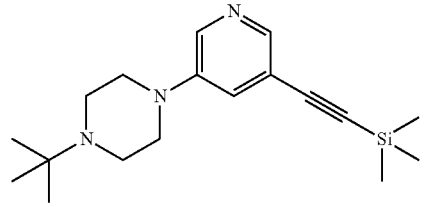 [SMILES: CC(C)(C)N1CCN(c2cncc(C#C[Si](C)(C)C)c2)CC1] | 2.23 | 316 |
| SM-5j | 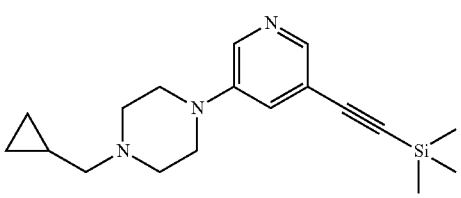 [SMILES: C[Si](C)(C)C#Cc1cncc(N2CCN(CC3CC3)CC2)c1] | 2.15 | 314 |
| SM-5k | 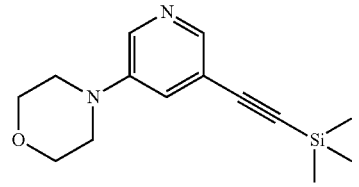 [SMILES: C[Si](C)(C)C#Cc1cncc(N2CCOCC2)c1] | 2.14 | 261 |
| SM-5l | 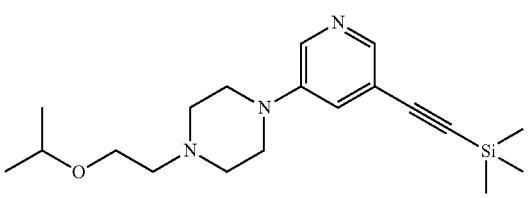 | 2.31 | 346 |
| SM-5m | 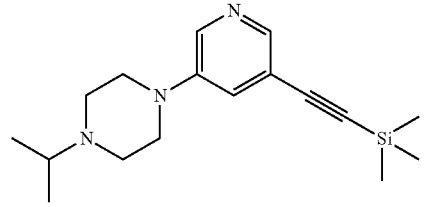 [SMILES: CC(C)N1CCN(c2cncc(C#C[Si](C)(C)C)c2)CC1] | 2.13 | 203 |
| SM-5n | 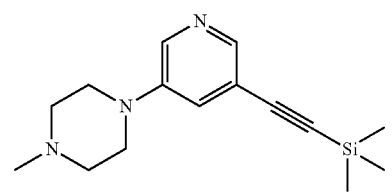 | 1.93 | 274 |

TABLE 1-continued

Silyl-protected alkynes SM-5

| # | structure | $t_{Ret.}$ (HPLC) [min] | MS (M + H)+ |
|---|---|---|---|
| SM-5o | 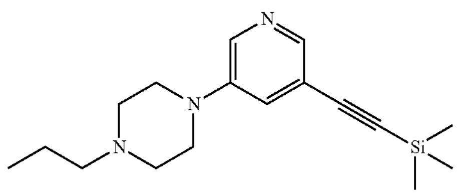 [SMILES: CCCN1CCN(c2cncc(C#C[Si](C)(C)C)c2)CC1] | 2.19 | 302 |
| SM-5p | 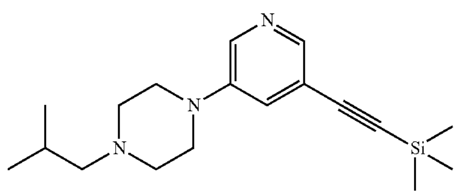 [SMILES: CC(C)CN1CCN(c2cncc(C#C[Si](C)(C)C)c2)CC1] | 2.44 | 316 |
| SM-5q | 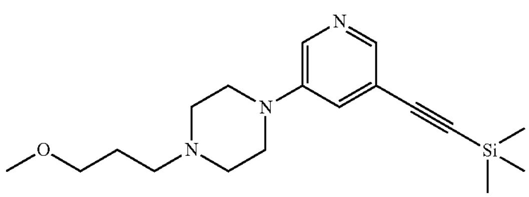 | 1.99 | 332 |
| SM-5r | 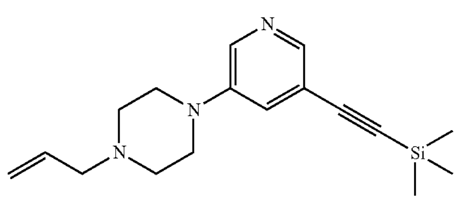 [SMILES: C=CCN1CCN(c2cncc(C#C[Si](C)(C)C)c2)CC1] | 2.12 | 300 |
| SM-5s | 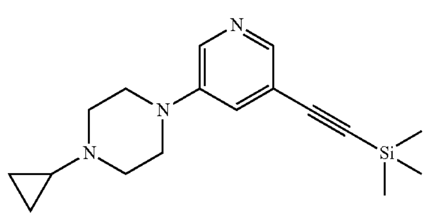 [SMILES: C[Si](C)(C)C#Cc1cncc(N2CCN(C3CC3)CC2)c1] | 2.16 | 300 |
| SM-5t | 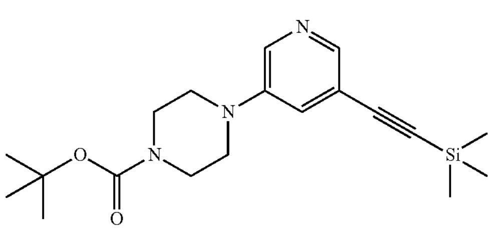 [SMILES: CC(C)(C)OC(=O)N1CCN(c2cncc(C#C[Si](C)(C)C)c2)CC1] | 2.27 | 360 |
| SM-5u[1] | 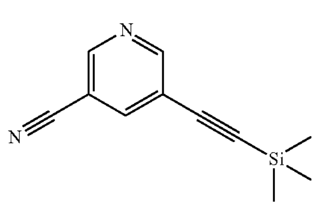 | 2.20 | 201 |

TABLE 1-continued

| Silyl-protected alkynes SM-5 | | | |
|---|---|---|---|
| # | structure | $t_{Ret.}$ (HPLC) [min] | MS (M + H)+ |
| SM-5v[2] | | 2.12 | 193 |
| SM-5w[3] | | 1.98 | 190 |
| SM-5x | | n.d. | 191 |
| SM-5y[4] | | 1.66 | 254/256 |
| SM-5z[5] | | n.d. | 220 |
| SM-5aa[6] | | n.d. | 234 |
| SM-5ab[7] | | n.d. | 211 |

[1] from commercially available 5-bromo-nicotinonitrile
[2] from commercially available 1,5-dimethyl-4-iodo-1H-pyrazole
[3] from commercially available 3-methyl-5-chloro-pyridine
[4] from commercially available 3,5-dibromo-pyridine
[5] from commercially available 3-bromo-5-ethoxy-pyridine
[6] from commercially available 3-bromo-5-isopropoxy-pyridine
[7] from commercially available 3-bromo-5-chloro-pyridine

B. Synthesis of Compounds (I) Starting from SM-1

B.1. Synthesis of Anilines A-1

B.1.1 Experimental Procedure for the Synthesis of Aniline A-1a

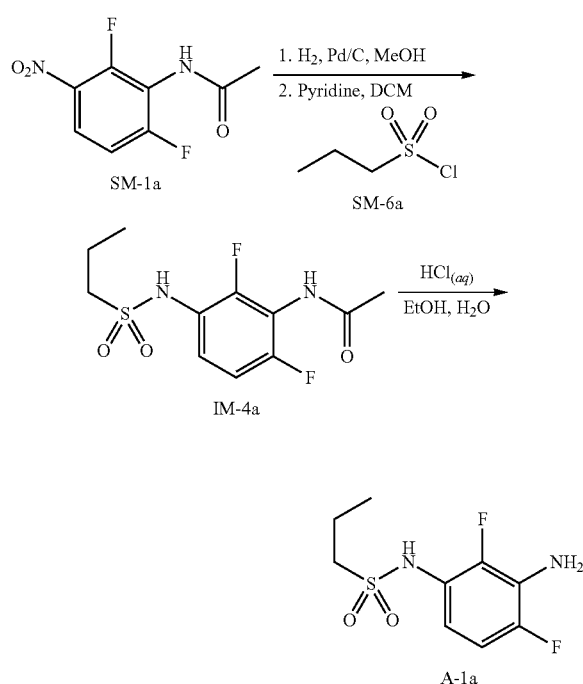

Step 1

SM-1a (55.0 g, 254 mmol) is taken-up in MeOH (1.0 L). Pd/C (10.0 g, 10%) is added and the mixture is hydrogenated in an autoclave at 200 psi for 3 h. The reaction mixture is filtered and concentrated under reduced pressure. The residue is purified by column chromatography on silica gel using DCM/MeOH (96:4) as eluent. The product containing fractions of the aniline intermediate (HPLC-MS: $t_{Ret.}$=0.25 min; MS (M−H)$^-$=185) are combined and evaporated.

Step 2

To the aniline intermediate (35.0 g, 188 mmol) in DCM (100 mL) and pyridine (6.6 mL, 75 mmol) is added n-propane sulfonyl chloride SM-6a (29.5 mL, 263 mmol) and the mixture is stirred at rt for 16 h. The reaction mixture is diluted with EtOAc (200 mL) and the layers are separated. The organic layer is washed with water and hydrochloric acid (1 N), dried over MgSO$_4$ and evaporated to yield IM-4a which was used without further purification.

Step 3

IM-4a (38.0 g, 130 mmol) is taken-up in EtOH (250 mL), H$_2$O (200 mL) and concentrated hydrochloric acid (200 mL) and heated to 80° C. for 2 h. The reaction mixture is concentrated under reduced pressure, aqueous NaOH (4 N) is added until pH=6 is reached and the mixture is extracted 2× with DCM. The combined organic layer is washed with saturated NaCl solution, dried over MgSO$_4$, filtered and evaporated to give A-1a (HPLC-MS: $t_{Ret.}$=0.22 min; MS (M−H)$^-$=249) as a hydrochloride which was used without further purification.

B.1.2 Experimental Procedure for the Synthesis of Aniline A-1d

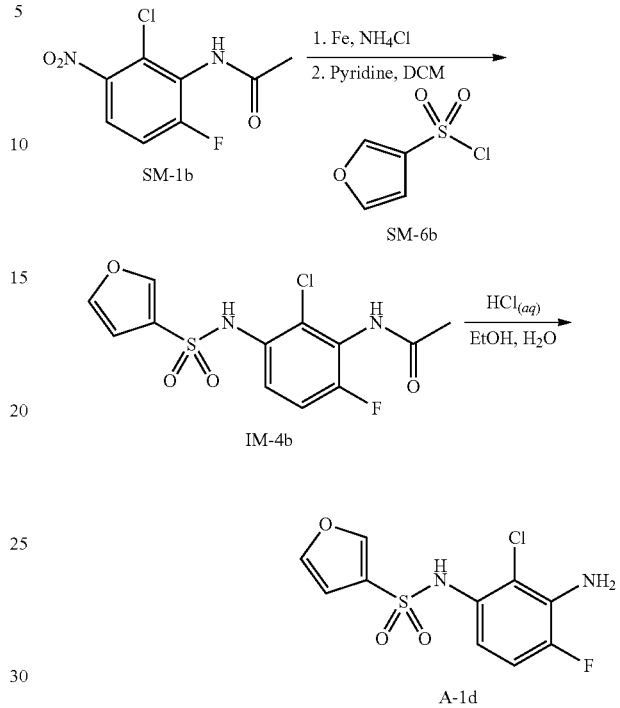

Step 1

To SM-1b (14.9 g, 64.0 mmol) in EtOH (450 mL) is added a solution of NH$_4$Cl (1.77 g, 33.1 mmol in 40 mL H$_2$O) and the mixture is stirred at 70° C. Fe powder (18.0 g, 322 mmol) is added in small portions and the mixture is stirred 20 h at 70° C. After cooling to rt EtOH is evaporated, the residue is taken-up in EtOAc, washed with H$_2$O and brine, dried over Na$_2$SO$_4$, filtered and evaporated to give the aniline which is used without further purification.

Step 2

To the aniline (1.80 g, 8.88 mmol) in DCM (85 mL) is added SM-6b (2.03 g, 11.8 mmol) and pyridine (1.8 mL) and the mixture is stirred at rt for 3 d. DCM is added and the resulting mixture is washed with semi-saturated KHSO$_4$ solution and brine, dried over MgSO$_4$, filtered and evaporated. The crude material is adsorbed on silica gel and purified by flash chromatography using DCM/MeOH gradients. The product containing fractions of IM-4b (HPLC-MS: $t_{Ret.}$=0.00 min; MS (M+H)$^+$=333) are evaporated.

Step 3

To IM-4b (2.30 g, 6.91 mmol) in EtOH (35 mL) is added semi-conc. HCl (35 mL) and the mixture is stirred 16 h at 80° C. After cooling to rt EtOH is evaporated, the aqueous residue is neutralized with 4 M NaOH to pH 6 and then extracted twice with DCM. The combined organic layer is washed with brine, dried over Na$_2$SO$_4$, filtered and evaporated. The residue is taken-up in MeCN/H$_2$O and freeze dried to give A-1d which is used without further purification.

Analogously to the procedures above additional anilines A-1 can be prepared (also using other nitro compounds SM-1) with various sulfonyl chlorides SM-6.

TABLE 2

Anilines A-1

| # | structure | t$_{Ret.}$ (HPLC) [min] | MS (M + H)$^+$ |
|---|---|---|---|
| A-1a | 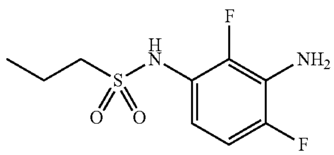 [SMILES: CCCS(=O)(=O)Nc1ccc(F)c(N)c1F] | 1.38 | 251 |
| A-1b | 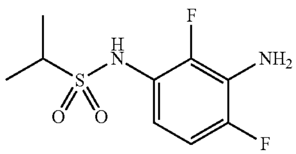 [SMILES: CC(C)S(=O)(=O)Nc1ccc(F)c(N)c1F] | n.d. | 251 |
| A-1c | 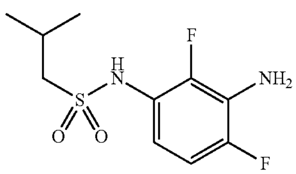 [SMILES: CC(C)CS(=O)(=O)Nc1ccc(F)c(N)c1F] | n.d. | 265 |
| A-1d | 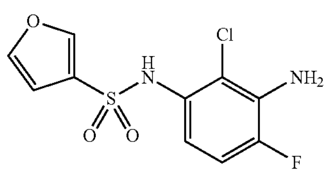 [SMILES: Nc1c(F)ccc(NS(=O)(=O)c2ccoc2)c1Cl] | n.d. | 290 |
| A-1e | 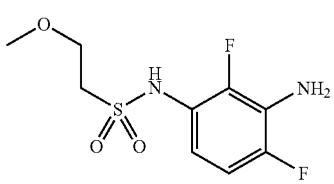 [SMILES: COCCS(=O)(=O)Nc1ccc(F)c(N)c1F] | n.d. | 267 |
| A-1f | 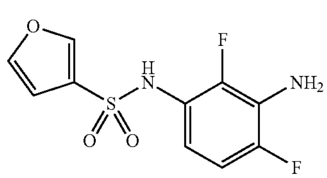 [SMILES: Nc1c(F)ccc(NS(=O)(=O)c2ccoc2)c1F] | n.d. | 275 |
| A-1g | 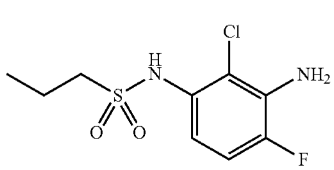 | n.d. | 266 |

B.2. Synthesis of Azides A-2

B.2.1 Experimental Procedure for the Synthesis of Azide a-2a

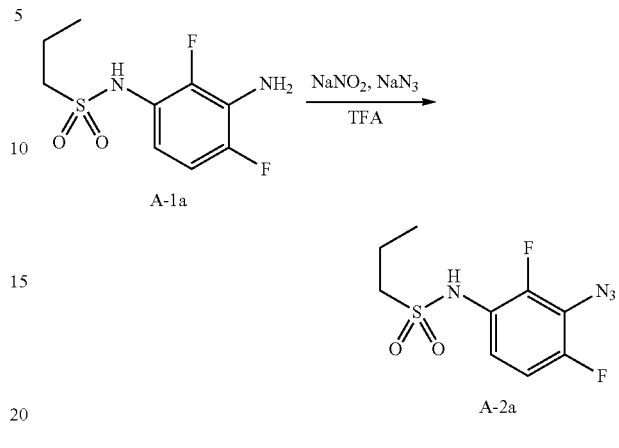

To the aniline A-1a (502 mg, 2.00 mmol) in TFA (4 mL) at 0° C. is added NaNO$_2$ (277 mg, 4.02 mmol) in small portions and the mixture is stirred for 30 min. NaN$_3$ (1.33 g, 20.2 mmol) is added and stirring is continued for additional 15 min. The reaction mixture is diluted dropwise with Et$_2$O and stirred for 1 h. Water is added and the mixture is extracted 3× with Et$_2$O. The combined organic layer is dried over MgSO$_4$, filtered and concentrated in vacuo to give A-2a (HPLC-MS: t$_{Ret.}$=0.78 min; MS (M−H)$^−$=275) which is used without further purification.

B.2.2 Experimental Procedure for the Synthesis of Azide A-2d

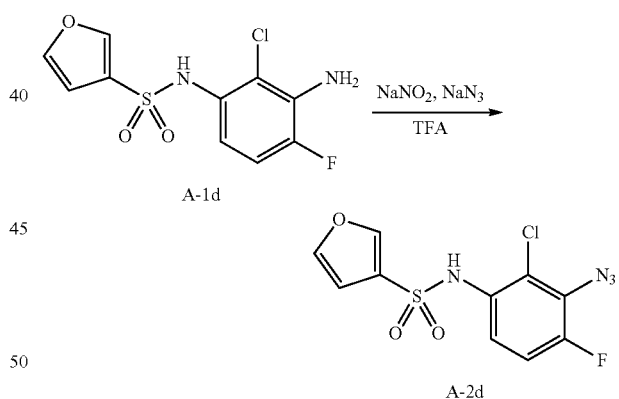

To the aniline A-1d (1.11 g, 3.82 mmol) in TFA (4 mL) at −10° C. is added NaNO$_2$ (316 mg, 4.58 mmol) in small portions and the mixture is stirred for 15 min below −5° C. NaN$_3$ (380 mg, 5.79 mmol) is added and stirring is continued for additional 60 min. The reaction mixture is diluted dropwise with Et$_2$O and stirred for 1 h. Water is added and the mixture is extracted twice with DCM. The combined organic layer is washed with semi-saturated NaHCO$_3$ and brine, dried over MgSO$_4$, filtered and concentrated in vacuo to give A-2d (HPLC-MS: t$_{Ret.}$=0.84 min; MS (M−H)$^−$=315) which is used without further purification.

Analogously to the procedures above additional azides A-2 can be prepared using anilines A-1.

TABLE 3

Azides A-2

| # | structure | $t_{Ret.}$ (HPLC) [min] | MS (M − H)⁻ |
|---|-----------|-------------------------|-------------|
| A-2a | 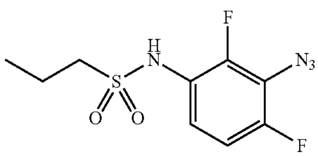 [SMILES: CCCS(=O)(=O)Nc1ccc(F)c(N=[N+]=[N-])c1F] | 0.78 | 275 |
| A-2b | 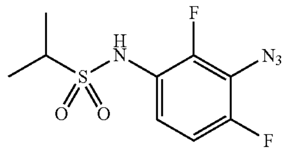 [SMILES: CC(C)S(=O)(=O)Nc1ccc(F)c(N=[N+]=[N-])c1F] | n.d. | 272 |
| A-2c | 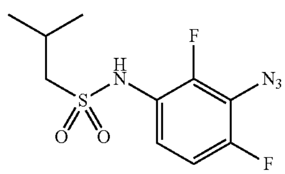 [SMILES: CC(C)CS(=O)(=O)Nc1ccc(F)c(N=[N+]=[N-])c1F] | n.d. | 289 |
| A-2d | 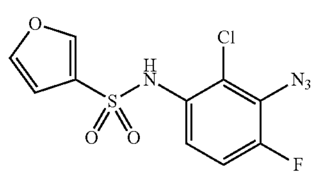 [SMILES: [N-]=[N+]=Nc1c(F)ccc(NS(=O)(=O)c2ccoc2)c1Cl] | 0.84 | 315 |
| A-2e | 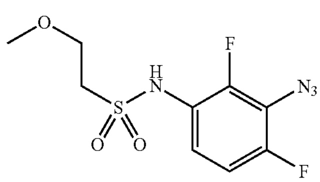 [SMILES: COCCS(=O)(=O)Nc1ccc(F)c(N=[N+]=[N-])c1F] | 0.60 | 291 |
| A-2f | 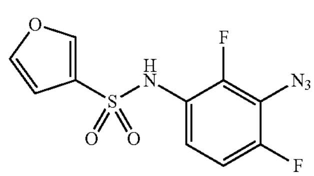 [SMILES: [N-]=[N+]=Nc1c(F)ccc(NS(=O)(=O)c2ccoc2)c1F] | n.d. | 299 |
| A-2g | 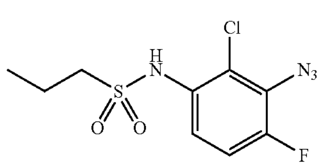 | n.d. | 291 |

B.3. Synthesis of Final Compounds (I)

B.3.1. Experimental Procedure for the Synthesis of Example I-1

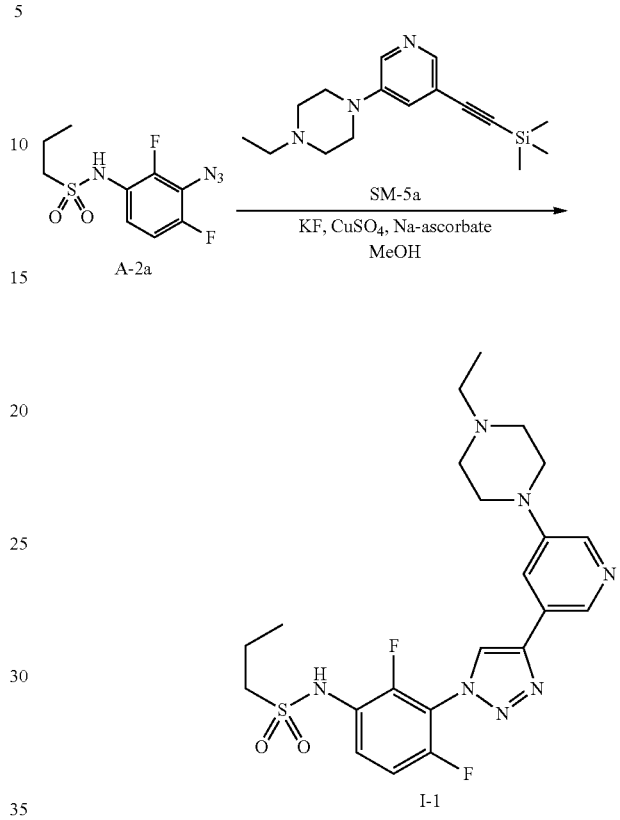

To the TMS-protected alkyne SM-5a (153 mg, 0.53 mmol) in MeOH (5 mL) is added KF (45.1 mg, 0.78 mmol) and the mixture is stirred at rt overnight. The azide A-2a (111 mg, 0.40 mmol) is added to the reaction mixture followed by Na-ascorbate (250 μL, 1 M aqueous solution, 0.25 mmol) and CuSO₄ (20 μL, 1 M in H₂O, 0.02 mmol). The resulting mixture is stirred at 45° C. for 16 h. The solvents are removed in vacuo, the residue is taken-up in H₂O and extracted 2× with EtOAc. The combined organic layer is dried over MgSO₄, filtered and evaporated. The residue is taken-up in DMF/H₂O/MeCN and purified by RP HPLC. The product containing fractions of I-1 (HPLC-MS: $t_{Ret.}$=1.15 min; MS (M+H)⁺=492) are freeze dried.

B.3.2. Experimental Procedure for the Synthesis of Example I-2

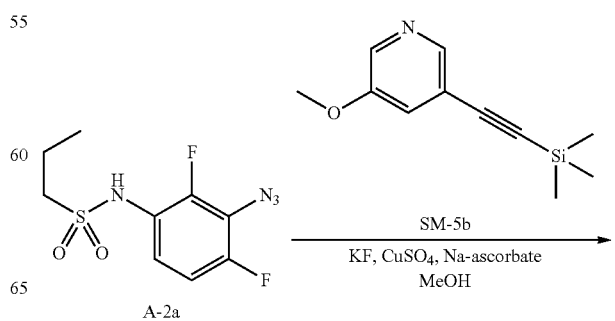

-continued

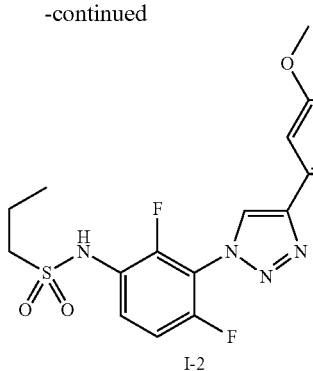

I-2

To the TMS-protected alkyne SM-5b (110 mg, 0.54 mmol) in MeOH (5 mL) is added KF (44.8 mg, 0.77 mmol) and the mixture is stirred at rt overnight. The azide A-2a (102 mg, 0.37 mmol) is added to the reaction mixture followed by Na-ascorbate (250 µL, 1M aqueous solution, 0.25 mmol) and CuSO$_4$ (20 µL, 1 M in H$_2$O, 0.02 mmol) and the resulting mixture is stirred at 45° C. for 16 h. The solvents are removed in vacuo, the residue is taken-up in H$_2$O and extracted 2× with EtOAc. The combined organic layer is dried over MgSO$_4$, filtered and evaporated. The residue is taken-up in DMF/H$_2$O/MeCN and purified by RP HPLC. The product containing fractions of I-2 (HPLC-MS: $t_{Ret.}$=1.05 min; MS (M+H)$^+$=410) are freeze dried.

B.3.3. Experimental Procedure for the Synthesis of Example I-3

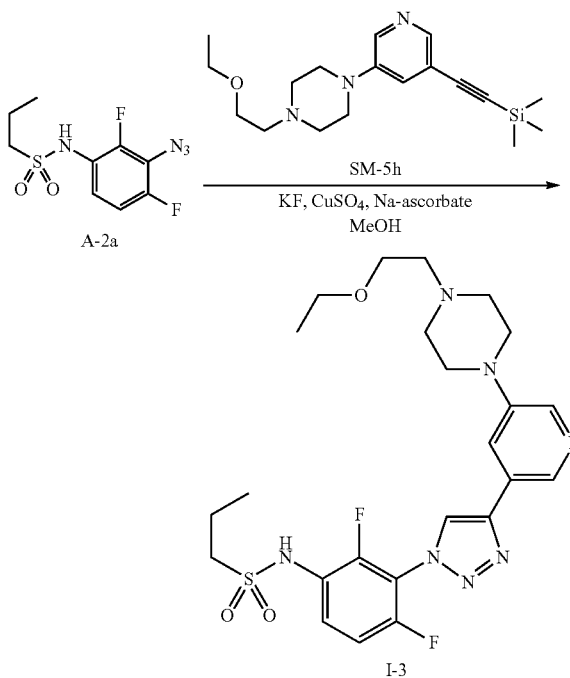

To the azide A-2a (155 mg, 0.56 mmol) in MeOH (5 mL) is added subsequently the TMS-protected alkyne SM-5h (213 mg, 0.64 mmol), KF (48.2 mg, 0.83 mmol), Na-ascorbate (83.4 mg, 0.42 mmol) and CuSO$_4$ (13.5 µL, 0.8 M in H$_2$O, 0.01 mmol) and the resulting mixture is stirred at 40° C. for 16 h. The solvents are evaporated and the residue is taken-up in DMF, filtered and purified by RP HPLC. The product containing fractions of I-3 (HPLC-MS: $t_{Ret.}$=1.17 min; MS (M+H)$^+$=536) are freeze dried.

B.3.4. Experimental Procedure for the Synthesis of Example I-4

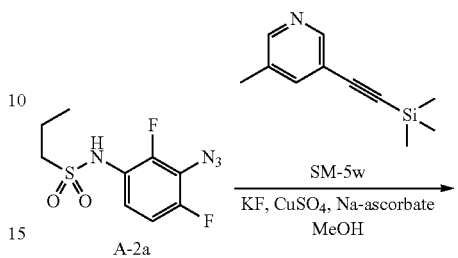

To the azide A-2a (152 mg, 0.55 mmol) in MeOH (5 mL) is added subsequently the TMS-protected alkyne SM-5w (106 mg, 0.56 mmol), KF (66.0 mg, 1.14 mmol), Na-ascorbate (79.6 mg, 0.40 mmol) and CuSO$_4$ (13.6 µL, 0.8 M in H$_2$O, 0.01 mmol) and the resulting mixture is stirred at 40° C. for 16 h. The solvents are evaporated and the residue is taken-up in DMF, filtered and purified by RP HPLC. The product containing fractions of I-4 (HPLC-MS: $t_{Ret.}$=0.00 min; MS (M+H)$^+$=394) are freeze dried.

B.3.5. Experimental Procedure for the Synthesis of I-5

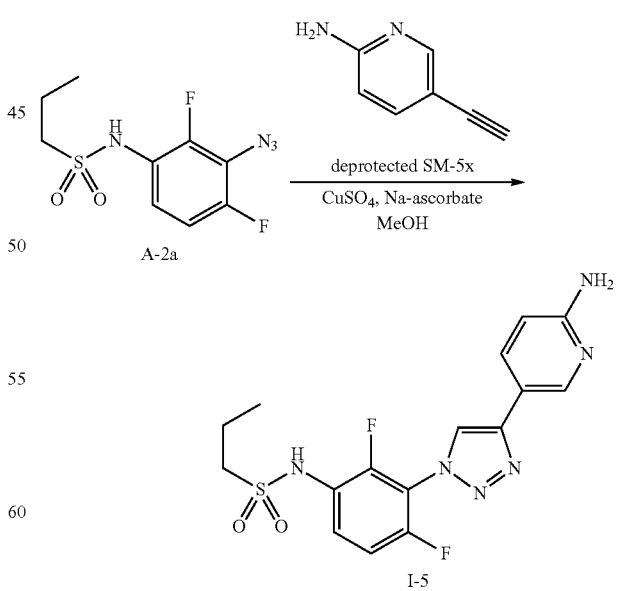

To the azide A-2a (199 mg, 0.72 mmol) in MeOH (10 mL) is added subsequently the deprotected alkyne SM-5x (96.3 mg, 0.82 mmol, deprotection is carried out with K$_2$CO$_3$), Na-ascorbate (107 mg, 0.54 mmol) and CuSO$_4$ (36.2 μL, 0.8 M in H$_2$O, 0.03 mmol). The resulting mixture is stirred at 40° C. for 3 d. The solvents are evaporated and the residue is taken-up in DMF, filtered and purified by RP HPLC. The product containing fractions of I-5 (HPLC-MS: $t_{Ret.}$=0.86 min; MS (M+H)$^+$=395) are freeze dried.

B.3.6. Experimental Procedure for the Synthesis of I-6

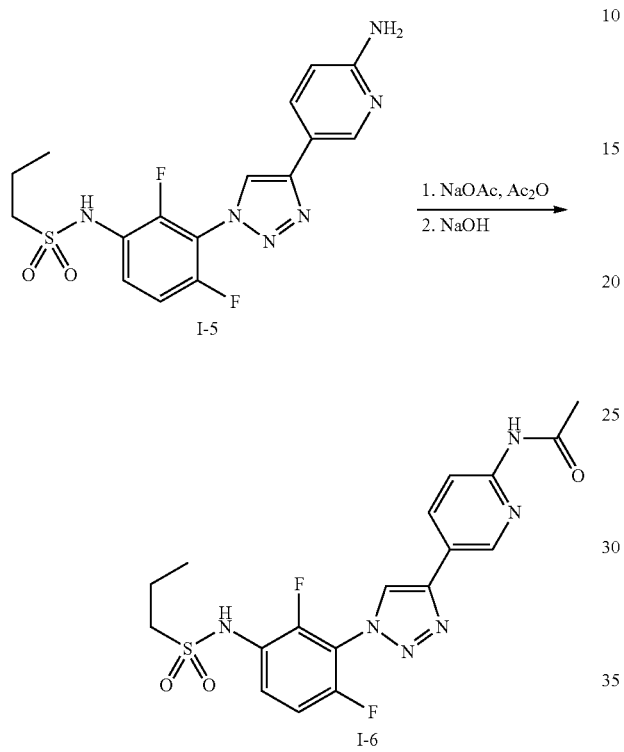

To I-5 (80.0 mg, 0.20 mmol) in Ac$_2$O (3 mL) is added NaOAc (26.5 mg, 0.32 mmol) and the mixture is refluxed for 2 h yielding the triple acetylated product. After re-cooling, H$_2$O and NaHCO$_3$ solution is added and the mixture is extracted 3× with DCM. The combined organic layer is dried over MgSO$_4$, filtered and evaporated. The residue is taken-up in MeOH (3 mL), NaOH (1 N, 1 mL) is added and the mixture stirred at 40° C. overnight. HCl (1 N, 1 mL) is added and the solvent is evaporated. The residue is taken-up in a small portion of DMF and purified by RP HPLC. The product containing fractions of I-6 (HPLC-MS: $t_{Ret.}$=0.95 min; MS (M+H)$^+$=437) are freeze dried.

B.3.7. Experimental Procedure for the Synthesis of I-7

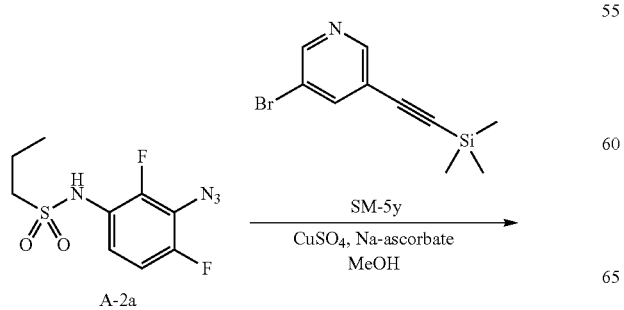

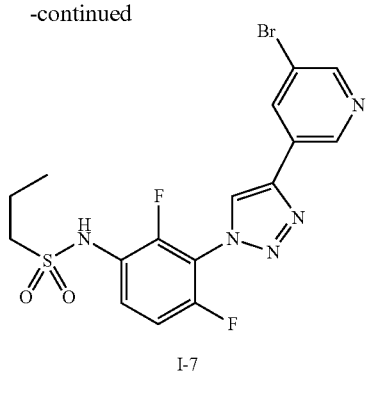

To the TMS-protected alkyne SM-5y (4.40 g, 17.3 mmol) in MeOH (70 mL) is added KF (4.89 g, 31.1 mmol) and the mixture is stirred at 45° C. overnight. The azide A-2a (4.78 g, 17.3 mmol) is added to the reaction mixture followed by Na-ascorbate (685 mg, 3.46 mmol) and CuSO$_4$ (4.3 mL, 0.8 M in H$_2$O, 3.46 mmol) and the resulting mixture is stirred at 45° C. for 3 d. The solvents are removed in vacuo, the residue is taken-up in H$_2$O and extracted 3× with DCM. The combined organic layer is dried over MgSO$_4$, filtered and evaporated. The residue is recrystallized from MeCN to yield I-7 (HPLC-MS: $t_{Ret.}$=0.96 min; MS (M+H)$^+$=458/460). Material with higher purity can be obtained by silica gel chromatography using cyclohexane/EtOAc gradients.

B.3.8. Experimental Procedure for the Synthesis of I-8

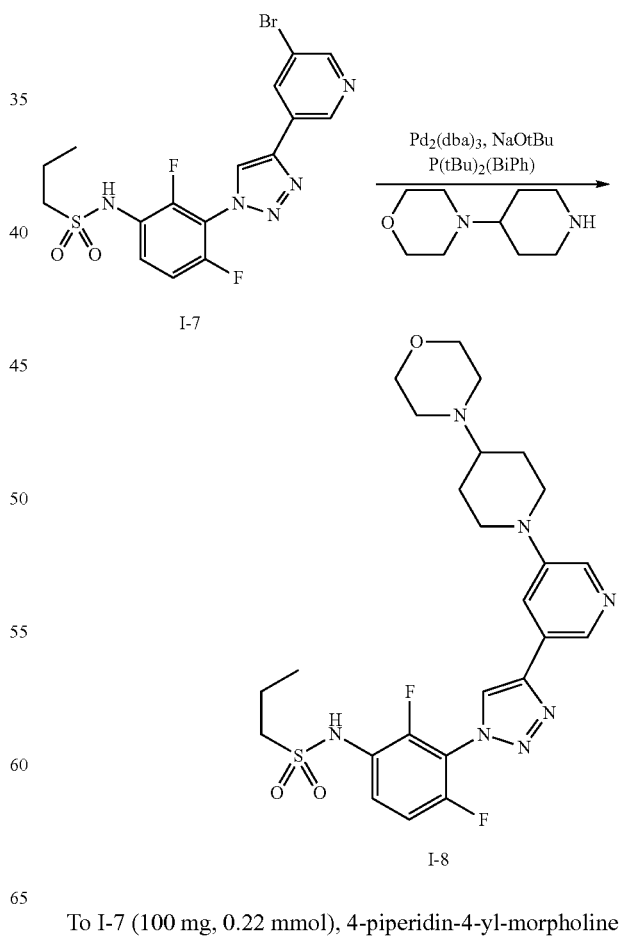

To I-7 (100 mg, 0.22 mmol), 4-piperidin-4-yl-morpholine (44.6 mg, 0.26 mmol), Pd$_2$(dba)$_3$ (20.0 mg, 0.02 mmol), (2-biphenyl)-di-tert-butyl-phosphine (13.2 mg, 0.04 mmol) and NaOtBu (86.5 mg, 0.87 mmol) is added 1,4-dioxane (2.5 mL) under an inert atmosphere. The mixture is stirred at 100° C. for 6 h and evaporated. The residue is taken-up in H$_2$O and EtOAc and the aqueous layer is extracted 3× with DCM. The combined organic layer is dried over MgSO$_4$, filtered and evaporated. The residue is taken-up in DCM/MeOH and purified by NP HPLC (DCM/MeOH gradient). The product containing fractions of I-8 (HPLC-MS: t$_{Ret.}$=0.88 min; MS (M+H)$^+$=548) are evaporated, taken-up in MeCN/H$_2$O and freeze dried.

B.3.9. Experimental Procedure for the Synthesis of I-33

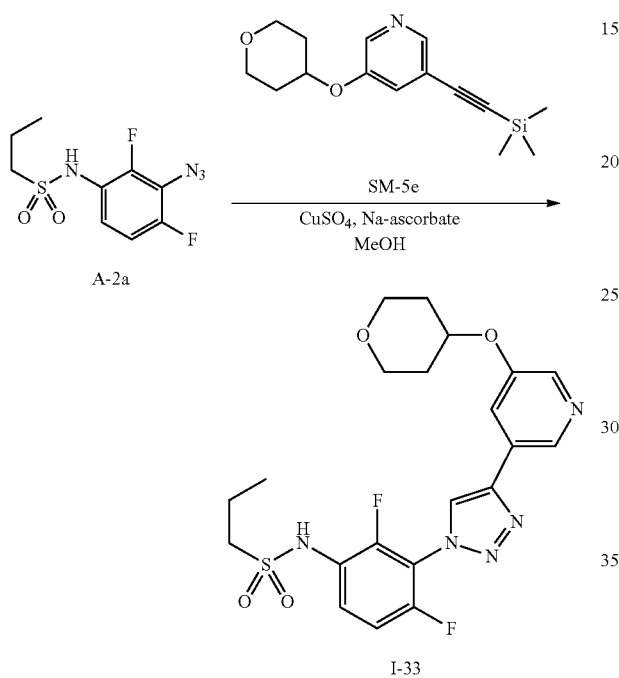

To the filtered reaction solution of SM-5e (636 mg [representing the theoretical yield], 2.31 mmol) from the former step (A.3.5.) is added MeOH (9 mL) and KF (452 mg, 7.78 mmol) and the mixture is stirred at 45° C. for 16 h. A-2a (287 mg, 1.04 mmol), Na-ascorbate (180 µL, 1 M aqueous solution, 0.18 mmol) and CuSO$_4$ (120 µL, 1 M aqueous solution, 0.12 mmol) is added and the reaction mixture is stirred for another 24 h. The solvents are evaporated, the residue is taken-up in H$_2$O and extracted 3× with EtOAc. The combined organic layer is evaporated, the residue taken-up in DMF/MeCN and purified by RP HPLC. The product containing fractions of I-33 (HPLC-MS: t$_{Ret.}$=0.88 min; MS (M+H)$^+$=480) are freeze dried.

B.3.10. Experimental Procedure for the Synthesis of I-48

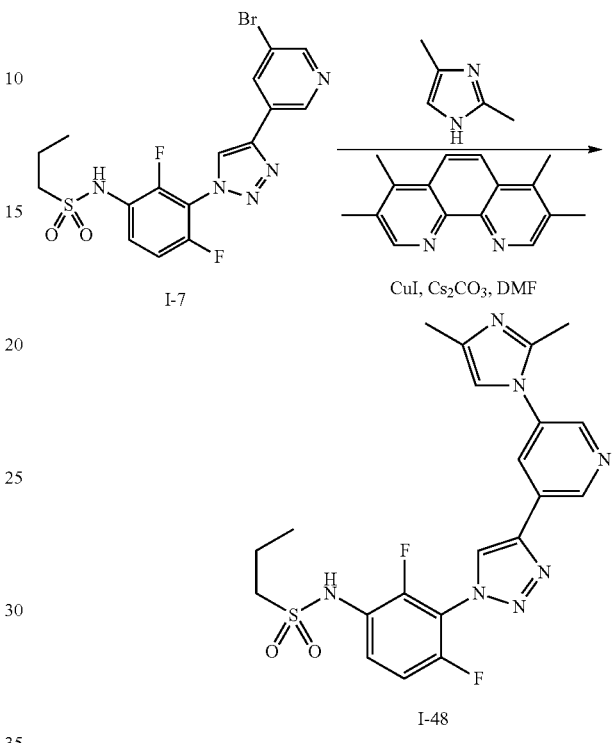

To I-7 (100 mg, 0.22 mmol) in DMF (3.0 mL) is added subsequently 2,4-dimethyl imidazole (228 mg, 2.30 mmol), 3,4,7,8-tetramethyl-1,10-phenanthroline (52.0 mg, 0.22 mmol), CuI (64.0 mg, 0.34 mmol) and Cs$_2$CO$_3$ (198 mg, 0.60 mmol) and the resulting mixture is stirred under an inert atmosphere (Ar) for 2 d at 105° C. After cooling to rt MeCN (25 mL) is added, the mixture is filtered and the volume of the filtrate is reduced in vacuo. A small amount of H$_2$O and some drops of formic acid are added to the residue and the mixture is purified twice by RP HPLC. The product containing fractions I-48 (HPLC-MS: t$_{Ret.}$=0.87 min; MS (M+H)$^+$=474) are freeze dried.

B.3.11. Experimental Procedure for the Synthesis of I-49 and I-50

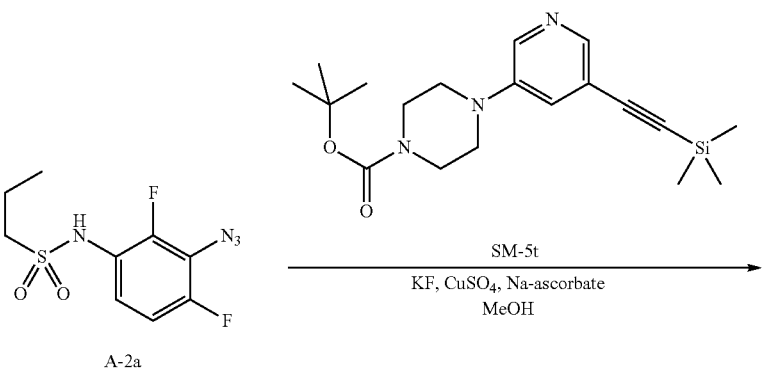

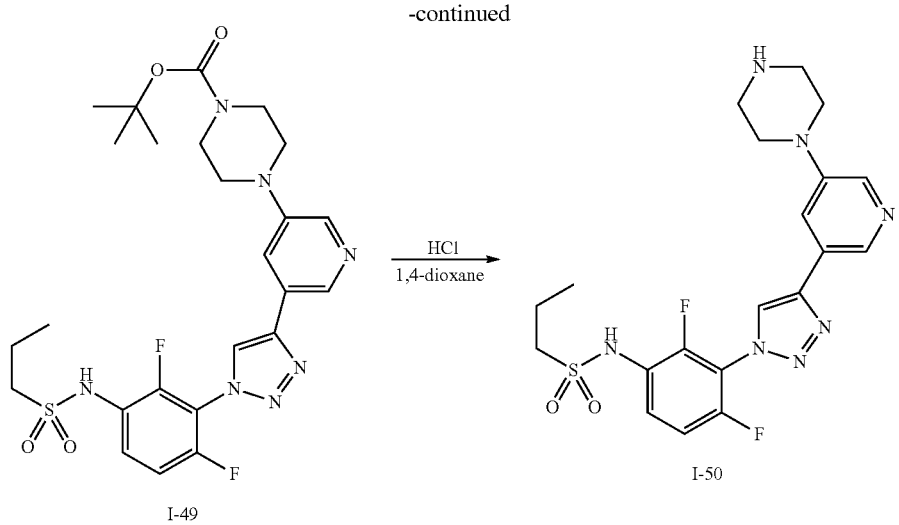

Step 1

To the TMS-protected alkyne SM-5t (3.46 g, 9.62 mmol) in MeOH (80 mL) is added KF (649 mg, 11.2 mmol) and the mixture is stirred at rt for 3 h. The azide A-2a (1.26 g, 8.16 mmol), Na-ascorbate (500 μL, 1.0 M in H$_2$O, 500 mmol) and CuSO$_4$ (200 μL, 1.0 M in H$_2$O, 200 mmol) are added subsequently and the resulting mixture is stirred at 45° C. for 16 h. The solvents are evaporated and the residue is taken-up in H$_2$O and extracted 3× with EtOAc. The combined organic layer is washed with brine, dried over MgSO$_4$, filtered and evaporated to give I-49 (HPLC-MS: t$_{Ret.}$=1.09 min; MS (M+H)$^+$=564) which is used without further purification.

Step 2

I-49 (4.61 g, 8.18 mmol) is taken-up in 1,4-dioxane (40 mL) and conc. HCl (1.0 mL) is added and the mixture is stirred at rt for 3 h. The solvents are removed in vacuo, the residue is taken-up in H$_2$O and the pH is adjusted. The mixture is extracted twice with EtOAc at pH 4 and at pH 8. The combined organic layer is evaporated, taken-up in MeCN/H$_2$O and freeze dried to give I-50 (HPLC-MS: t$_{Ret.}$=0.87 min; MS (M+H)$^+$=464). In order to increase the yield of I-50 the aqueous phase is freeze dried and the residue purified by RP HPLC.

B.3.12. Experimental Procedure for the Synthesis of I-51

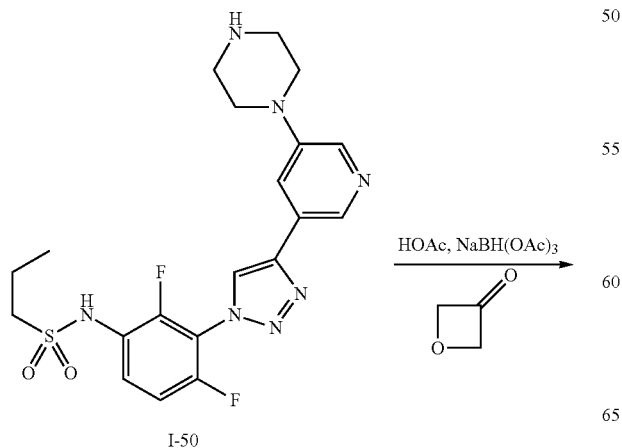

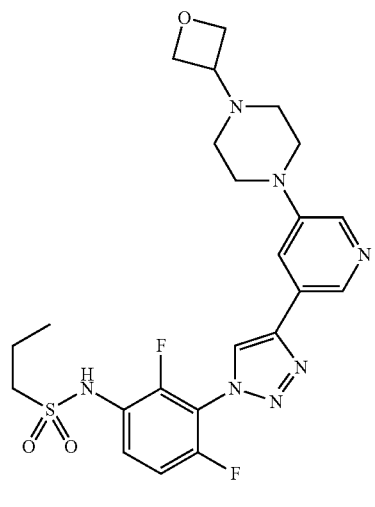

I-50 (152 mg, 0.33 mmol) is taken-up in DMF (3 mL), 3-oxetanone (69.0 mg, 0.96 mmol) and HOAc (20 μL) is added and the mixture is shaken for 1 min. NaBH(OAc)$_3$ (349 mg, 1.65 mmol) is added and the mixture is stirred at rt for 18 h. H$_2$O is added and the mixture is purified by RP HPLC. The product containing fractions of I-51 (HPLC-MS: t$_{Ret.}$=0.83 min; MS (M+H)$^+$=520) are freeze dried.

B.3.13. Experimental Procedure for the Synthesis of I-52

B.3.14. Experimental Procedure for the Synthesis of I-53

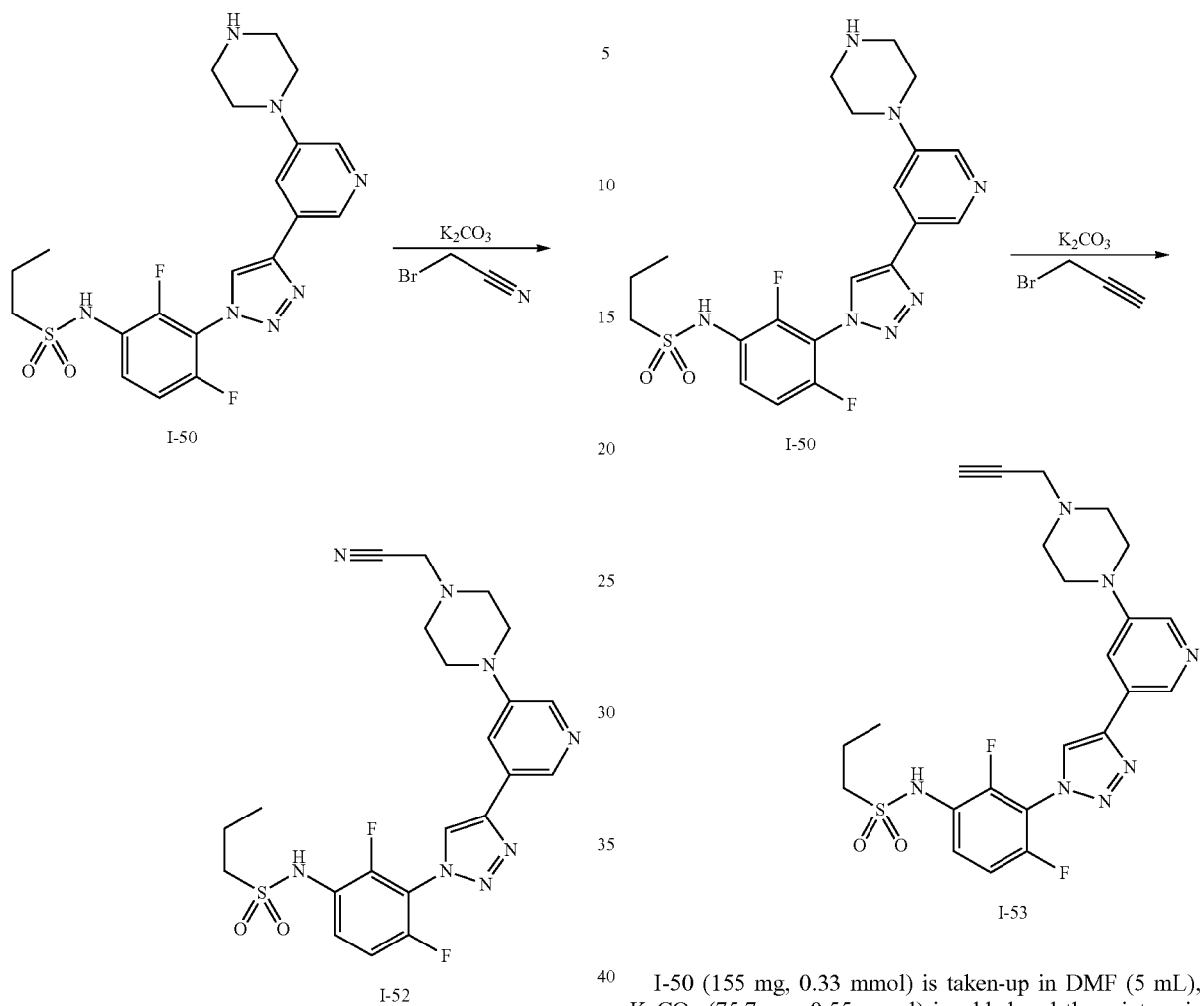

I-50 (149 mg, 0.32 mmol) is taken-up in DMF (5 mL), K₂CO₃ (75.1 mg, 0.54 mmol) is added and the mixture is stirred for 10 min. Bromoacetonitrile (72.5 mg, 0.59 mmol) is added and the mixture is stirred at 50° C. for 72 h. After cooling to rt 1 N HCl is added, the reaction mixture is filtered and purified by RP HPLC and subsequently by NP HPLC. The product containing fractions of I-52 (HPLC-MS: t_{Ret.}=0.99 min; MS (M+H)⁺=503) are evaporated, taken-up in H₂O/MeCN and freeze dried.

I-50 (155 mg, 0.33 mmol) is taken-up in DMF (5 mL), K₂CO₃ (75.7 mg, 0.55 mmol) is added and the mixture is stirred for 10 min. Propargyl bromide (as 80% solution in toluene; 74.4 mg, 0.50 mmol) is added and the mixture is stirred at 50° C. for 72 h. After cooling to rt 1 N HCl is added, the reaction mixture is filtered and purified by RP HPLC and subsequently by NP HPLC. The product containing fractions of I-53 (HPLC-MS: t_{Ret.}=1.05 min; MS (M+H)⁺=502) are evaporated, taken-up in H₂O/MeCN and freeze dried.

to B.3.15. Experimental Procedure for the Synthesis of Example I-54

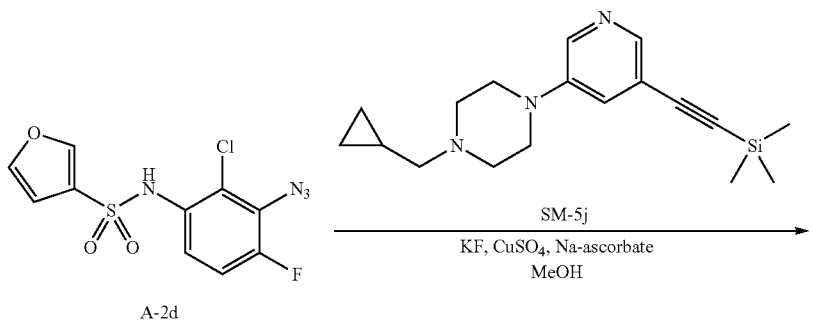

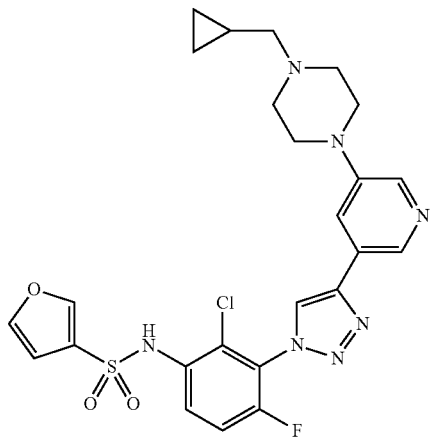

I-54

To the azide A-2d (100 mg, 0.32 mmol) in MeOH (3 mL) is added subsequently the TMS-protected alkyne SM-5j (103 mg, 0.33 mmol), KF (30.0 mg, 0.51 mmol), H$_2$O (500 μL), Na-ascorbate (33.0 mg, 0.17 mmol) and CuSO$_4$ (6.00 mg, 0.04 mmol) and the resulting mixture is stirred at rt for 20 h. The reaction mixture is diluted with MeCN (2 mL), filtered and purified by RP HPLC. The product containing fractions of I-54 (HPLC-MS: t$_{Ret.}$=0.95 min; MS (M+H)$^+$=558) are freeze dried.

B.3.16. Experimental Procedure for the Synthesis of Example I-55

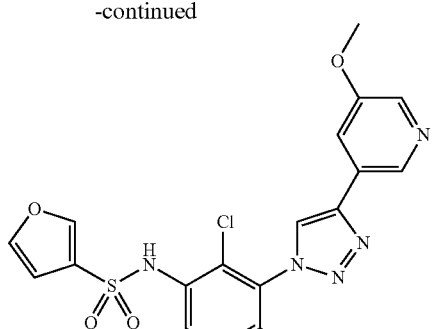

I-55

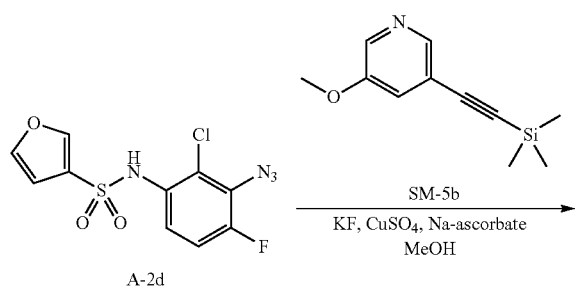

To the azide A-2d (100 mg, 0.32 mmol) in MeOH (3 mL) is added subsequently the TMS-protected alkyne SM-5b (71.0 mg, 0.35 mmol), KF (30.0 mg, 0.51 mmol), H$_2$O (500 μL), Na-ascorbate (32.0 mg, 0.16 mmol) and CuSO$_4$ (5.00 mg, 0.03 mmol) and the resulting mixture is stirred at rt for 20 h. The resulting precipitate is filtered, washed with H$_2$O and cooled MeCN and air dried. The material is taken-up in MeCN/H$_2$O and freeze dried to give I-55 (HPLC-MS: t$_{Ret.}$=0.80 min; MS (M+H)$^+$=450).

Analogously to the procedures B.3.1. to B.3.16. above additional final compounds are prepared using additional azides A-2 and silyl-protected alkynes SM-5.

TABLE 4

Structures and analytical data of example compound I-1 to I-37 and I-48 to I-76.

| # | structure | procedure | tRet. (HPLC) [min] | MS (M + H)+ |
|---|---|---|---|---|
| I-1 | 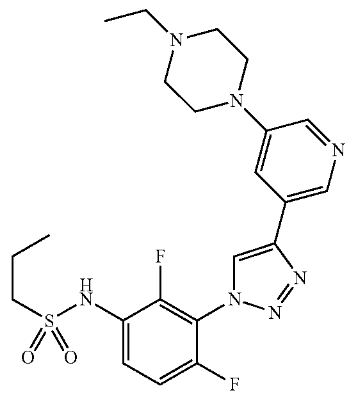 [SMILES: CCCS(=O)(=O)Nc1ccc(F)c(-n2cc(-c3cncc(N4CCN(CC)CC4)c3)nn2)c1F] | B.3.1. | 1.15 | 492 |
| I-2 | 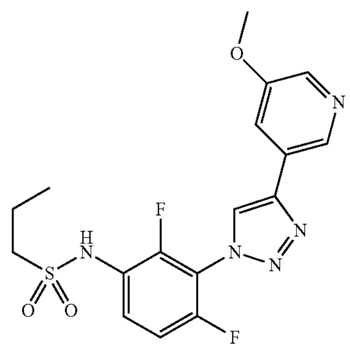 [SMILES: CCCS(=O)(=O)Nc1ccc(F)c(-n2cc(-c3cncc(OC)c3)nn2)c1F] | B.3.2. | 1.05 | 410 |
| I-3 | 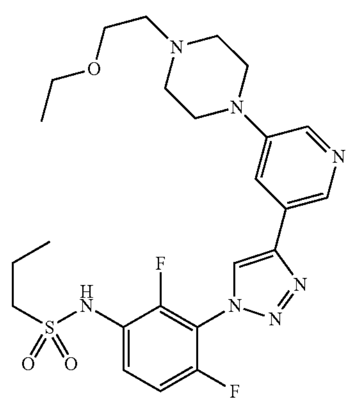 [SMILES: CCCS(=O)(=O)Nc1ccc(F)c(-n2cc(-c3cncc(N4CCN(CCOCC)CC4)c3)nn2)c1F] | B.3.3. | 1.17 | 536 |
| I-4 | 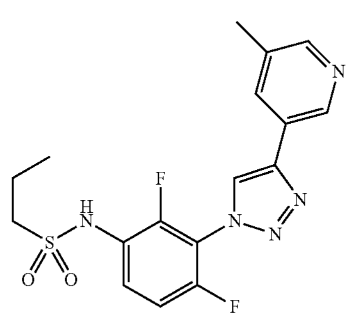 [SMILES: CCCS(=O)(=O)Nc1ccc(F)c(-n2cc(-c3cncc(C)c3)nn2)c1F] | B.3.4. | 0.00 | 394 |

TABLE 4-continued

Structures and analytical data of example compound I-1 to I-37 and I-48 to I-76.

| # | structure | procedure | tRet. (HPLC) [min] | MS (M + H)+ |
|---|---|---|---|---|
| I-5 | 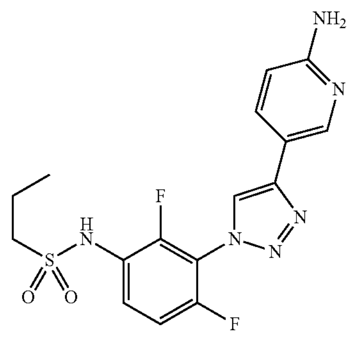 [SMILES: CCCS(=O)(=O)Nc1ccc(F)c(-n2cc(-c3ccc(N)nc3)nn2)c1F] | B.3.5. | 0.86 | 395 |
| I-6 | 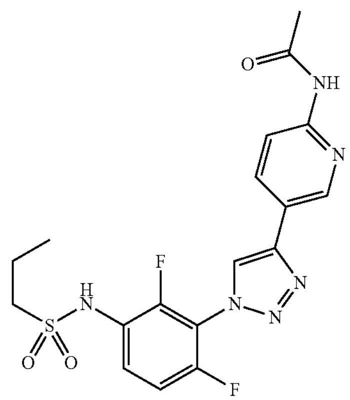 [SMILES: CCCS(=O)(=O)Nc1ccc(F)c(-n2cc(-c3ccc(NC(C)=O)nc3)nn2)c1F] | B.3.6. | 0.95 | 437 |
| I-7 | 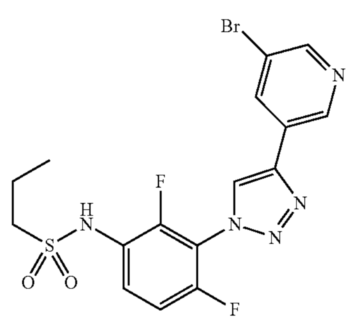 [SMILES: CCCS(=O)(=O)Nc1ccc(F)c(-n2cc(-c3cncc(Br)c3)nn2)c1F] | B.3.7. | 0.96 | 458/460 |
| I-8 | 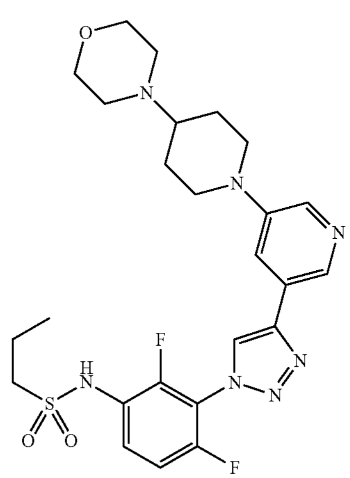 [SMILES: CCCS(=O)(=O)Nc1ccc(F)c(-n2cc(-c3cncc(N4CCC(N5CCOCC5)CC4)c3)nn2)c1F] | B.3.8. | 0.88 | 548 |

TABLE 4-continued
Structures and analytical data of example compound
I-1 to I-37 and I-48 to I-76.
| # | structure | procedure | tRet. (HPLC) [min] | MS (M + H)+ |
|---|---|---|---|---|
| I-9 | 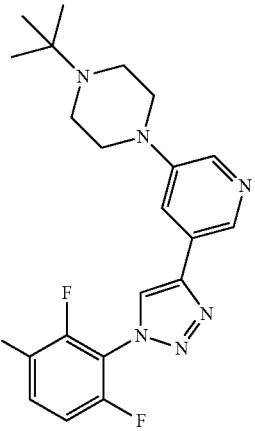 | B.3.1. | 0.95 | 520 |
| I-10 | 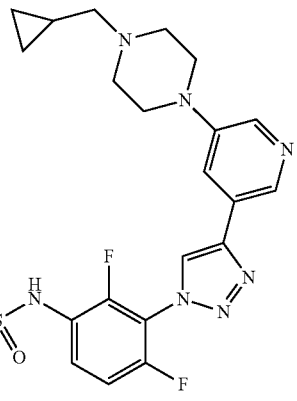 | B.3.1. | 0.93 | 518 |
| I-11 | 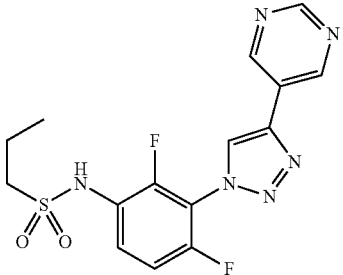 [SMILES: CCCS(=O)(=O)Nc1ccc(F)c(-n2cc(-c3cncnc3)nn2)c1F] | B.3.2. | 0.96 | 381 |
| I-12 | 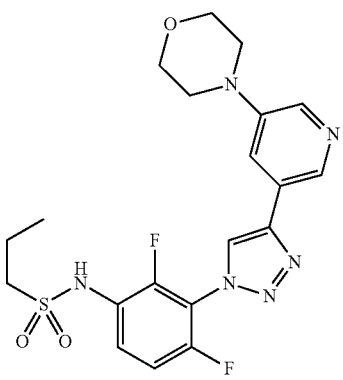 [SMILES: CCCS(=O)(=O)Nc1ccc(F)c(-n2cc(-c3cncc(N4CCOCC4)c3)nn2)c1F] | B.3.1. | 1.12 | 465 |

TABLE 4-continued

Structures and analytical data of example compound
I-1 to I-37 and I-48 to I-76.

| # | structure | procedure | tRet. (HPLC) [min] | MS (M + H)+ |
|---|---|---|---|---|
| I-13 | 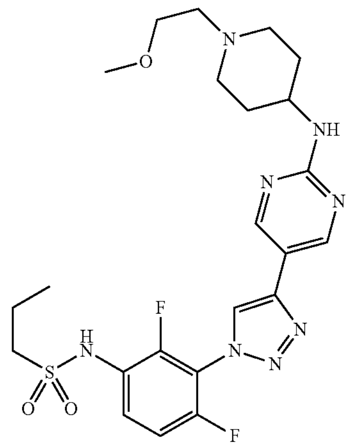 [SMILES: CCCS(=O)(=O)Nc1ccc(F)c(-n2cc(-c3cnc(NC4CCN(CCOC)CC4)nc3)nn2)c1F] | B.3.1. | 1.13 | 537 |
| I-14 | 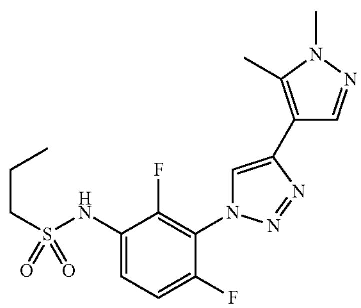 [SMILES: CCCS(=O)(=O)Nc1ccc(F)c(-n2cc(-c3cnn(C)c3C)nn2)c1F] | B.3.2. | 0.96 | 397 |
| I-15 | 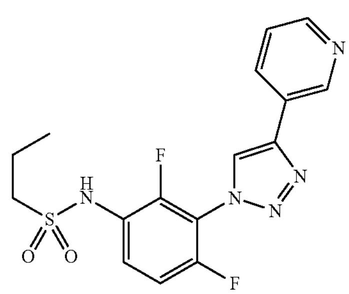 [SMILES: CCCS(=O)(=O)Nc1ccc(F)c(-n2cc(-c3cccnc3)nn2)c1F] | B.3.2. | 0.88 | 380 |
| I-16 | 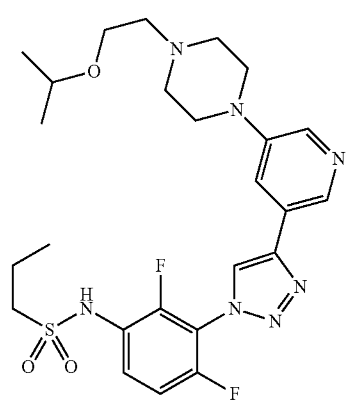 [SMILES: CCCS(=O)(=O)Nc1ccc(F)c(-n2cc(-c3cncc(N4CCN(CCOC(C)C)CC4)c3)nn2)c1F] | B.3.3. | 1.22 | 550 |

TABLE 4-continued

Structures and analytical data of example compound
I-1 to I-37 and I-48 to I-76.

| # | structure | procedure | tRet. (HPLC) [min] | MS (M + H)+ |
|---|---|---|---|---|
| I-17 | 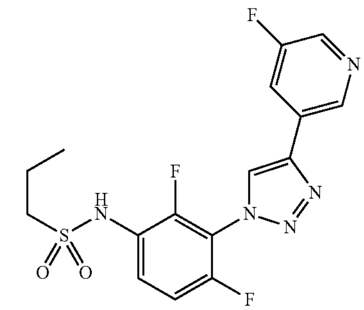 [SMILES: CCCS(=O)(=O)Nc1ccc(F)c(-n2cc(-c3cncc(F)c3)nn2)c1F] | B.3.2. | 0.00 | 398 |
| I-18 | 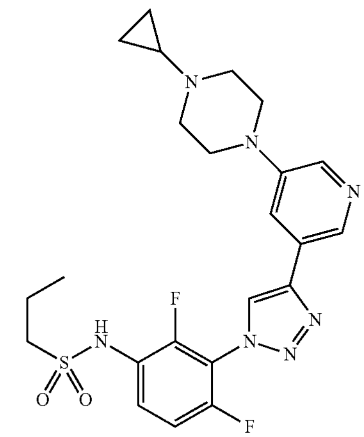 [SMILES: CCCS(=O)(=O)Nc1ccc(F)c(-n2cc(-c3cncc(N4CCN(C5CC5)CC4)c3)nn2)c1F] | B.3.1. | 0.93 | 504 |
| I-19 | 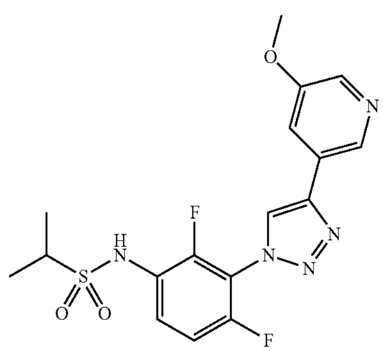 [SMILES: COc1cncc(-c2cn(-c3c(F)ccc(NS(=O)(=O)C(C)C)c3F)nn2)c1] | B.3.2. | 0.85 | 410 |
| I-20 | 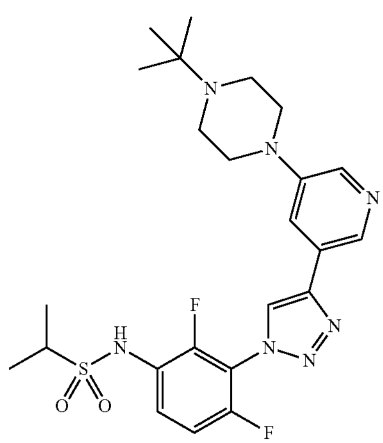 [SMILES: CC(C)S(=O)(=O)Nc1ccc(F)c(-n2cc(-c3cncc(N4CCN(C(C)(C)C)CC4)c3)nn2)c1F] | B.3.1. | 0.97 | 520 |

TABLE 4-continued

Structures and analytical data of example compound
I-1 to I-37 and I-48 to I-76.

| # | structure | procedure | tRet. (HPLC) [min] | MS (M + H)+ |
|---|---|---|---|---|
| I-21 | 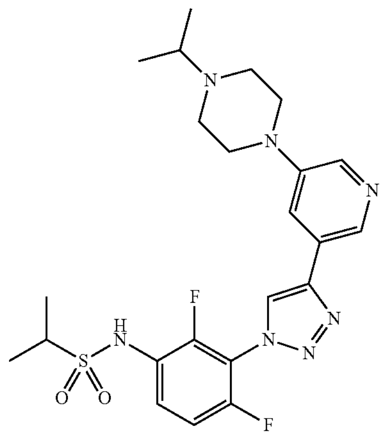 [SMILES: CC(C)N1CCN(c2cncc(-c3cn(-c4c(F)ccc(NS(=O)(=O)C(C)C)c4F)nn3)c2)CC1] | B.3.1. | 0.93 | 506 |
| I-22 | 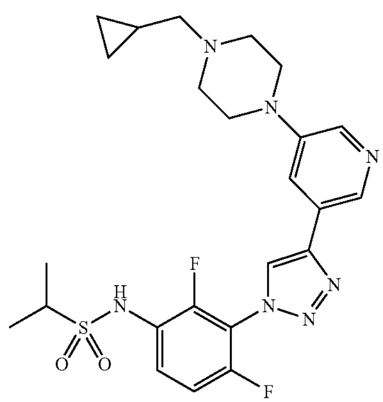 [SMILES: CC(C)S(=O)(=O)Nc1ccc(F)c(-n2cc(-c3cncc(N4CCN(CC5CC5)CC4)c3)nn2)c1F] | B.3.1. | 0.95 | 518 |
| I-23 | 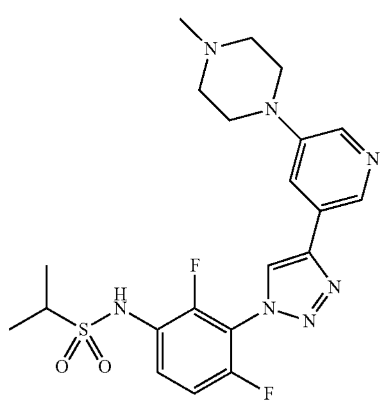 [SMILES: CC(C)S(=O)(=O)Nc1ccc(F)c(-n2cc(-c3cncc(N4CCN(C)CC4)c3)nn2)c1F] | B.3.1. | 0.89 | 478 |

TABLE 4-continued

Structures and analytical data of example compound
I-1 to I-37 and I-48 to I-76.

| # | structure | procedure | tRet. (HPLC) [min] | MS (M + H)+ |
|---|---|---|---|---|
| I-24 | 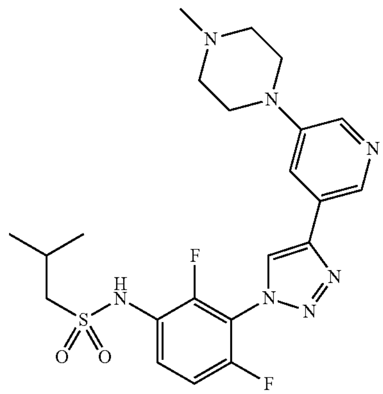 [SMILES: CC(C)CS(=O)(=O)Nc1ccc(F)c(-n2cc(-c3cncc(N4CCN(C)CC4)c3)nn2)c1F] | B.3.1. | 0.94 | 492 |
| I-25 | 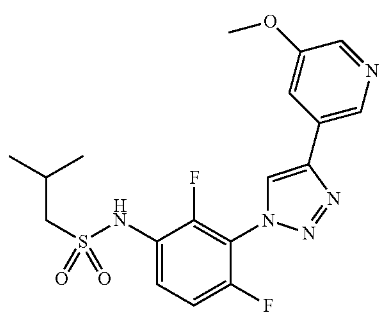 [SMILES: COc1cncc(-c2cn(-c3c(F)ccc(NS(=O)(=O)CC(C)C)c3F)nn2)c1] | B.3.2. | 0.91 | 424 |
| I-26 | 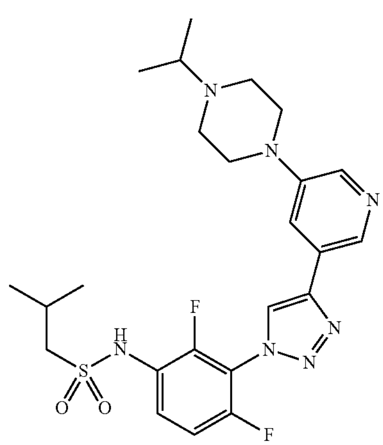 [SMILES: CC(C)CS(=O)(=O)Nc1ccc(F)c(-n2cc(-c3cncc(N4CCN(C(C)C)CC4)c3)nn2)c1F] | B.3.1. | 1.03 | 520 |

TABLE 4-continued
Structures and analytical data of example compound
I-1 to I-37 and I-48 to I-76.
| # | structure | procedure | tRet. (HPLC) [min] | MS (M + H)+ |
|---|---|---|---|---|
| I-27 | 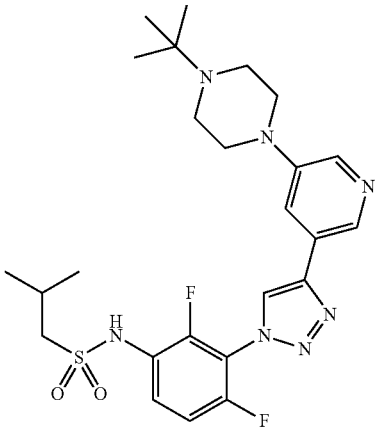 [SMILES: CC(C)CS(=O)(=O)Nc1ccc(F)c(-n2cc(-c3cncc(N4CCN(C(C)(C)C)CC4)c3)nn2)c1F] | B.3.1. | 1.08 | 534 |
| I-28 | 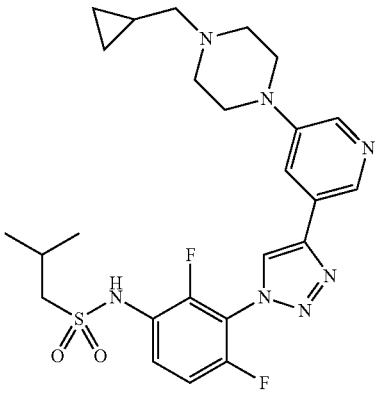 [SMILES: CC(C)CS(=O)(=O)Nc1ccc(F)c(-n2cc(-c3cncc(N4CCN(CC5CC5)CC4)c3)nn2)c1F] | B.3.1. | 1.04 | 532 |
| I-29 | 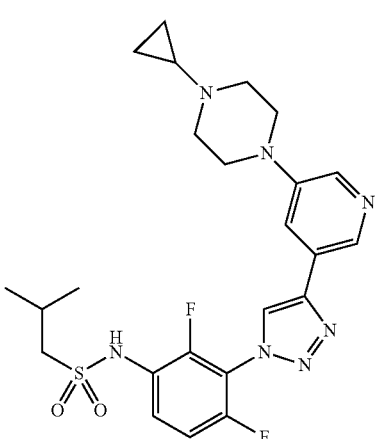 | B.3.1. | 1.09 | 518 |

TABLE 4-continued

Structures and analytical data of example compound
I-1 to I-37 and I-48 to I-76.

| # | structure | procedure | tRet. (HPLC) [min] | MS (M + H)+ |
|---|---|---|---|---|
| I-30 | 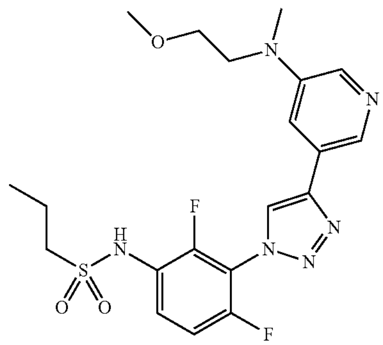 [SMILES: CCCS(=O)(=O)Nc1ccc(F)c(-n2cc(-c3cncc(N(C)CCOC)c3)nn2)c1F] | B.3.8. | 0.93 | 467 |
| I-31 | 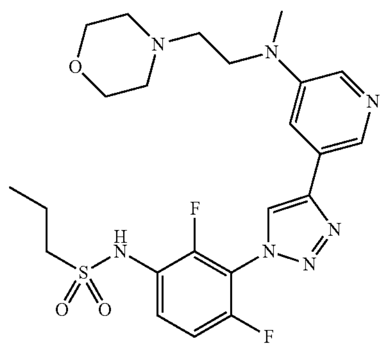 [SMILES: CCCS(=O)(=O)Nc1ccc(F)c(-n2cc(-c3cncc(N(C)CCN4CCOCC4)c3)nn2)c1F] | B.3.8. | 0.88 | 522 |
| I-32 | 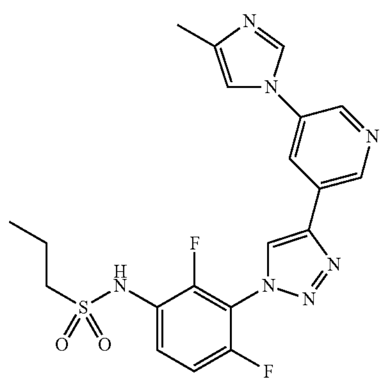 [SMILES: CCCS(=O)(=O)Nc1ccc(F)c(-n2cc(-c3cncc(-n4cnc(C)c4)c3)nn2)c1F] | B.3.3. | 1.06 | 460 |
| I-33 | 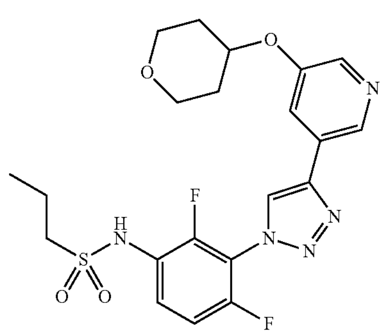 [SMILES: CCCS(=O)(=O)Nc1ccc(F)c(-n2cc(-c3cncc(OC4CCOCC4)c3)nn2)c1F] | B.3.9. | 0.88 | 480 |

TABLE 4-continued

Structures and analytical data of example compound
I-1 to I-37 and I-48 to I-76.

| # | structure | procedure | tRet. (HPLC) [min] | MS (M + H)+ |
|---|---|---|---|---|
| I-34 | 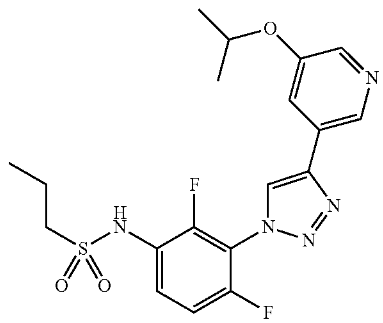 [SMILES: CCCS(=O)(=O)Nc1ccc(F)c(-n2cc(-c3cncc(OC(C)C)c3)nn2)c1F] | B.3.9. | 0.98 | 438 |
| I-35 | 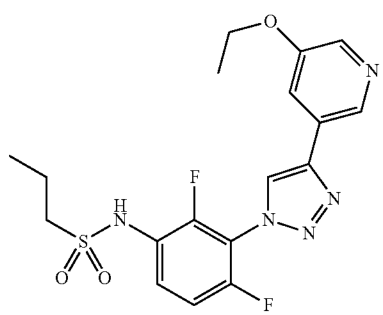 [SMILES: CCCS(=O)(=O)Nc1ccc(F)c(-n2cc(-c3cncc(OCC)c3)nn2)c1F] | B.3.9. | 0.94 | 424 |
| I-36 | 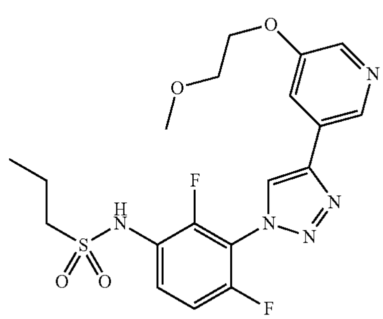 [SMILES: CCCS(=O)(=O)Nc1ccc(F)c(-n2cc(-c3cncc(OCCOC)c3)nn2)c1F] | B.3.9. | 0.89 | 454 |
| I-37 | 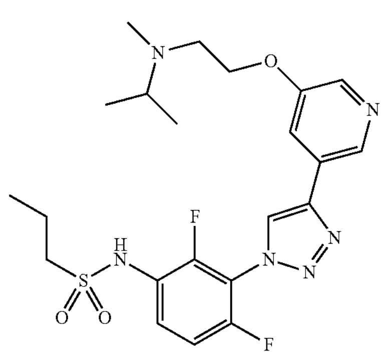 [SMILES: CCCS(=O)(=O)Nc1ccc(F)c(-n2cc(-c3cncc(OCCN(C)C(C)C)c3)nn2)c1F] | B.3.2.[7] | 1.00 | 495 |

TABLE 4-continued

Structures and analytical data of example compound
I-1 to I-37 and I-48 to I-76.

| # | structure | procedure | tRet. (HPLC) [min] | MS (M + H)+ |
|---|---|---|---|---|
| I-48 | 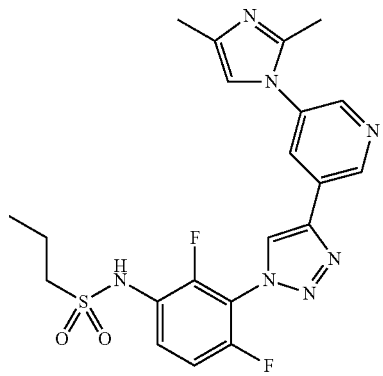 [SMILES: CCCS(=O)(=O)Nc1ccc(F)c(-n2cc(-c3cncc(-n4cc(C)nc4C)c3)nn2)c1F] | B.3.10. | 0.87 | 474 |
| I-49 | 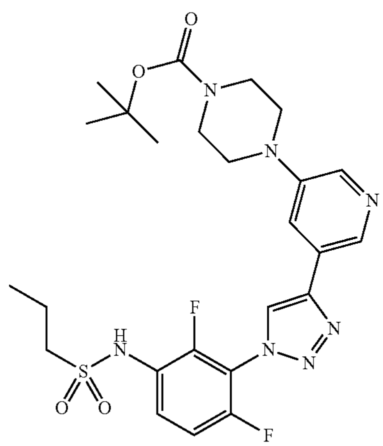 [SMILES: CCCS(=O)(=O)Nc1ccc(F)c(-n2cc(-c3cncc(N4CCN(C(=O)OC(C)(C)C)CC4)c3)nn2)c1F] | B.3.11. | 1.09 | 564 |
| I-50 | 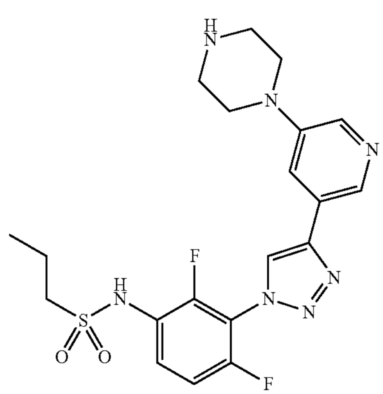 [SMILES: CCCS(=O)(=O)Nc1ccc(F)c(-n2cc(-c3cncc(N4CCNCC4)c3)nn2)c1F] | B.3.11. | 0.87 | 464 |

TABLE 4-continued
Structures and analytical data of example compound I-1 to I-37 and I-48 to I-76.
| # | structure | procedure | tRet. (HPLC) [min] | MS (M + H)+ |
|---|---|---|---|---|
| I-51 | 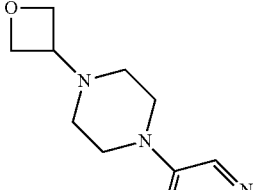 | B.3.12. | 0.83 | 520 |
| I-52 | 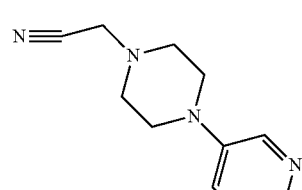 | B.3.13. | 0.99 | 503 |
| I-53 | 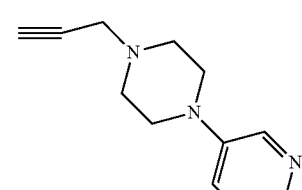 | B.3.14. | 1.05 | 502 |

TABLE 4-continued
Structures and analytical data of example compound
I-1 to I-37 and I-48 to I-76.
| # | structure | procedure | tRet. (HPLC) [min] | MS (M + H)+ |
|---|---|---|---|---|
| I-54 | 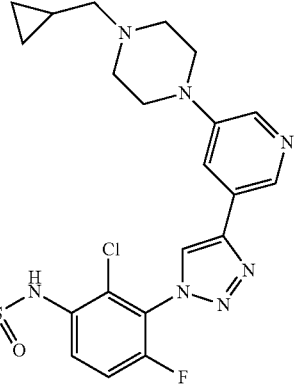 | B.3.15. | 0.95 | 558 |
| I-55 | 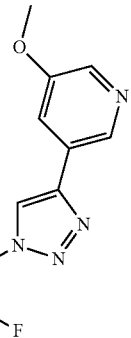 | B.3.16. | 0.80 | 450 |
| I-56 | 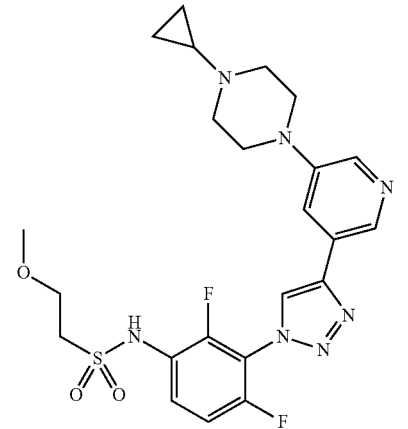 [SMILES: COCCS(=O)(=O)Nc1ccc(F)c(-n2cc(-c3cncc(N4CCN(C5CC5)CC4)c3)nn2)c1F] | B.3.3. | 0.98 | 520 |

TABLE 4-continued
Structures and analytical data of example compound
I-1 to I-37 and I-48 to I-76.
| # | structure | procedure | tRet. (HPLC) [min] | MS (M + H)⁺ |
|---|---|---|---|---|
| I-57 | 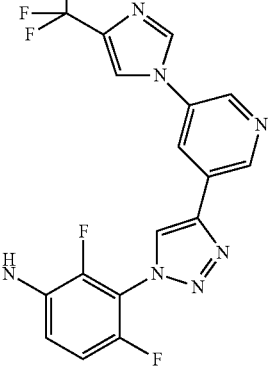 | B.3.10. | 0.94 | (M − H)⁻ = 512 |
| I-58 | 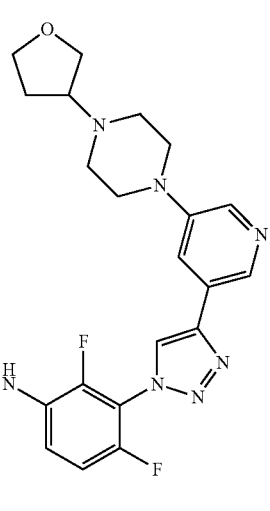 | B.3.12. | 0.86 | 534 |
| I-59 | 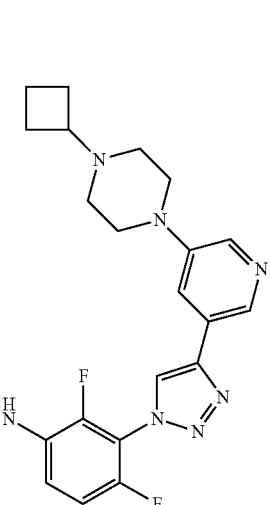 | B.3.12. | 0.98 | 518 |

TABLE 4-continued
Structures and analytical data of example compound
I-1 to I-37 and I-48 to I-76.
| # | structure | procedure | tRet. (HPLC) [min] | MS (M + H)+ |
|---|---|---|---|---|
| I-60 | 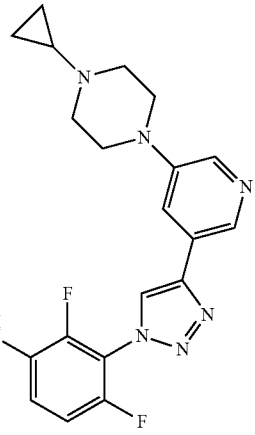 | B.3.3. | 0.92 | 528 |
| I-61 | 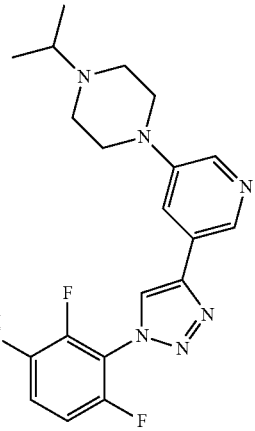 | B.3.3. | 0.95 | 530 |
| I-62 | 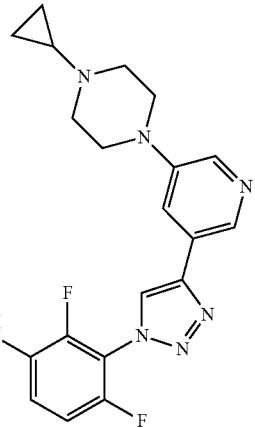 | B.3.3. | 0.94 | 542 |

TABLE 4-continued
Structures and analytical data of example compound
I-1 to I-37 and I-48 to I-76.
| # | structure | procedure | tRet. (HPLC) [min] | MS (M + H)+ |
|---|---|---|---|---|
| I-63 | 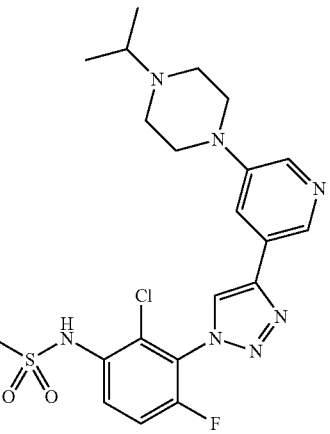 | B.3.15. | 0.92 | 522 |
| I-64 | 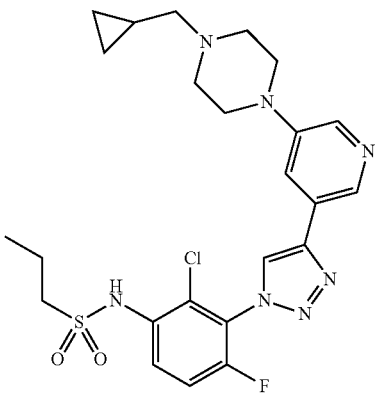 [SMILES: CCCS(=O)(=O)Nc1ccc(F)c(-n2cc(-c3cncc(N4CCN(CC5CC5)CC4)c3)nn2)c1Cl] | B.3.15. | 0.95 | 534 |
| I-65 | 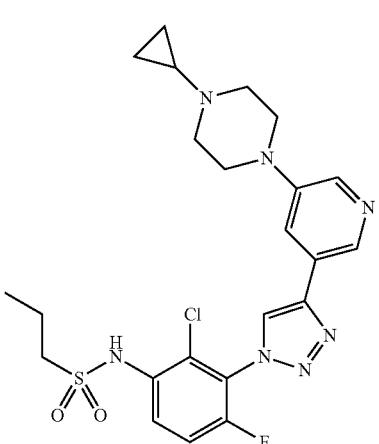 | B.3.15. | 0.76 | 520 |

TABLE 4-continued

Structures and analytical data of example compound
I-1 to I-37 and I-48 to I-76.

| # | structure | procedure | tRet. (HPLC) [min] | MS (M + H)+ |
|---|---|---|---|---|
| I-66 | 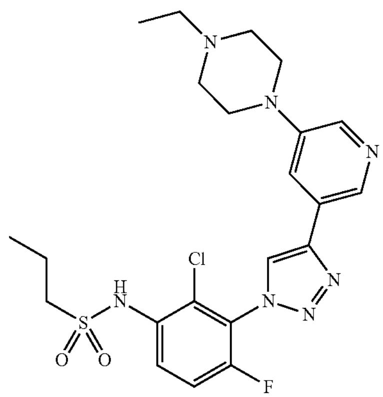 [SMILES: CCCS(=O)(=O)Nc1ccc(F)c(-n2cc(-c3cncc(N4CCN(CC)CC4)c3)nn2)c1Cl] | B.3.15. | 0.87 | 508 |
| I-67 | 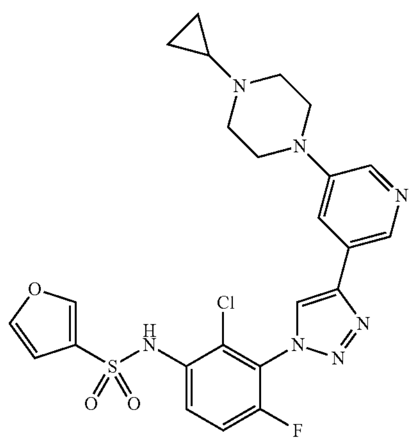 [SMILES: O=S(=O)(Nc1ccc(F)c(-n2cc(-c3cncc(N4CCN(C5CC5)CC4)c3)nn2)c1Cl)c1ccoc1] | B.3.15. | 0.93 | 544 |
| I-68 | 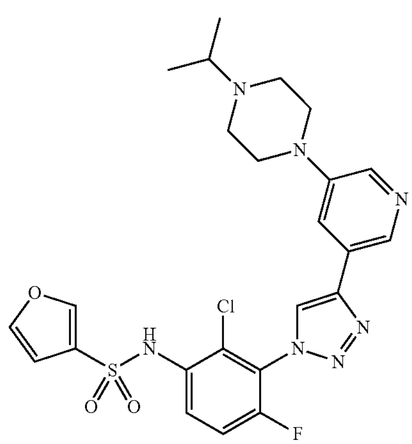 [SMILES: CC(C)N1CCN(c2cncc(-c3cn(-c4c(F)ccc(NS(=O)(=O)c5ccoc5)c4Cl)nn3)c2)CC1] | B.3.15. | 0.92 | 546 |

TABLE 4-continued

Structures and analytical data of example compound
I-1 to I-37 and I-48 to I-76.

| # | structure | procedure | tRet. (HPLC) [min] | MS (M + H)+ |
|---|---|---|---|---|
| I-69 | 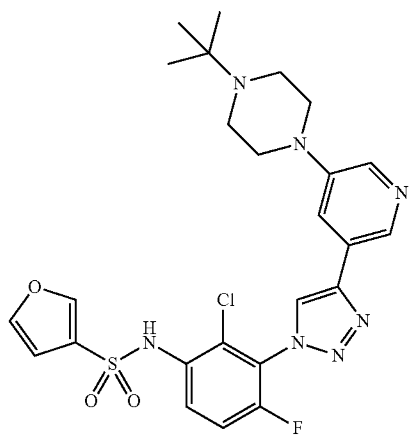 [SMILES: CC(C)(C)N1CCN(c2cncc(-c3cn(-c4c(F)ccc(NS(=O)(=O)c5ccoc5)c4Cl)nn3)c2)CC1] | B.3.15. | 0.95 | 560 |
| I-70 | 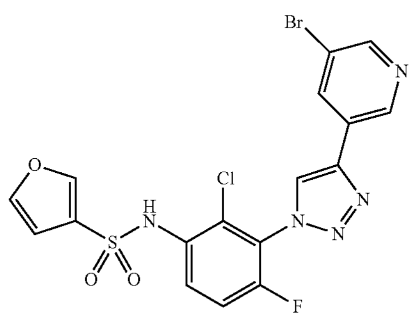 [SMILES: O=S(=O)(Nc1ccc(F)c(-n2cc(-c3cncc(Cl)c3)nn2)c1Cl)c1ccoc1] | B.3.16. | 0.73 | 498 |
| I-71 | 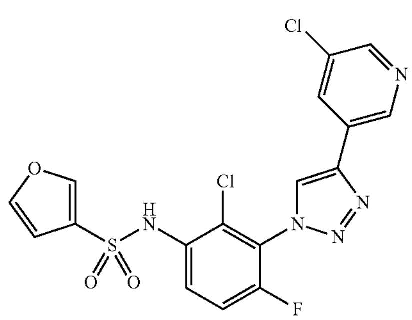 | B.3.16. | 0.70 | 454 |
| I-72 | 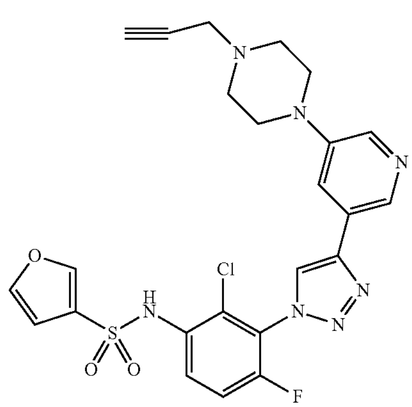 [SMILES: C#CCN1CCN(c2cncc(-c3cn(-c4c(F)ccc(NS(=O)(=O)c5ccoc5)c4Cl)nn3)c2)CC1] | 3.14. | 0.71 | 542 |

TABLE 4-continued
Structures and analytical data of example compound
I-1 to I-37 and I-48 to I-76.
| # | structure | procedure | tRet. (HPLC) [min] | MS (M + H)+ |
|---|-----------|-----------|--------------------|-----|
| I-73 | 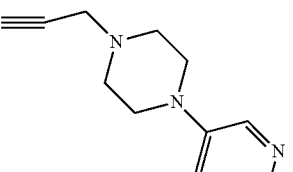 | 3.14. | 0.86 | 518 |
| I-74 | 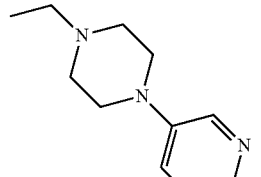 | 3.15. | 0.87 | 532 |
| I-75 | 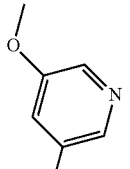 | 3.16. | 0.85 | 426 |

TABLE 4-continued

Structures and analytical data of example compound
I-1 to I-37 and I-48 to I-76.

| # | structure | procedure | tRet. (HPLC) [min] | MS (M + H)+ |
|---|-----------|-----------|---------------------|-------------|
| I-76 | 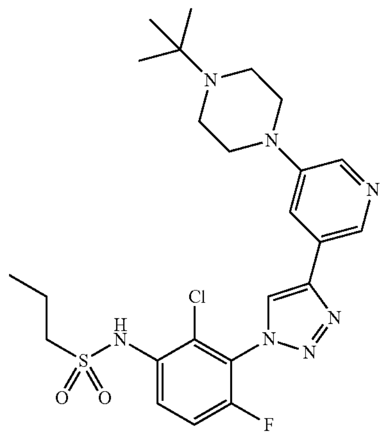 [SMILES: CCCS(=O)(=O)Nc1ccc(F)c(-n2cc(-c3cncc(N4CCN(C(C)(C)C)CC4)c3)nn2)c1Cl] | 3.15. | 1.01 | 536 |

[7] In situ silyl deprotection with TBAF instead of KF

C. Synthesis of Compounds (I) Starting from SM-2

C.1. Synthesis of Azides B-1
C.I.1. Experimental Procedure for the Synthesis of B1-a

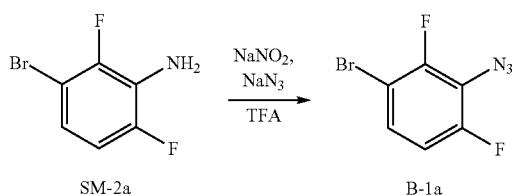 [SMILES: Nc1c(F)ccc(Br)c1F ; [N-]=[N+]=Nc1c(F)ccc(Br)c1F]

SM-2a → B-1a

The aniline SM-2a (2.66 g, 12.8 mmol) is suspended in TFA (60 mL) and cooled to 0° C. NaNO$_2$ (1.39 g, 20.1 mmol) is added and the mixture stirred for 30 min. NaN$_3$ (1.06 g, 16.2 mmol) is slowly added at 0° C. and the mixture is stirred for additional 60 min. Et$_2$O (25 mL) is added dropwise, the cooling bath is removed and the reaction mixture is allowed to warm to rt. H$_2$O is added and the mixture is extracted 3× with Et$_2$O. The combined organic layer is dried over MgSO$_4$, filtered and evaporated to yield the azide B-1a which is used without further purification.

Analogously to this procedure additional azides B-1 can be prepared from anilines SM-2.

TABLE 5

| Azides B-1 | | | |
|---|---|---|---|
| # | structure | $t_{Ret.}$ (HPLC) [min] | MS (M + H)+ |
| B-1a | | 1.46 | n.a. |

TABLE 5-continued

| Azides B-1 | | | |
|---|---|---|---|
| # | structure | $t_{Ret.}$ (HPLC) [min] | MS (M + H)+ |
| B-1b | | 1.52 | n.a. |

C.2. Synthesis of Triazoles B-2
C.2.1. Experimental Procedure for the Synthesis of B2-a

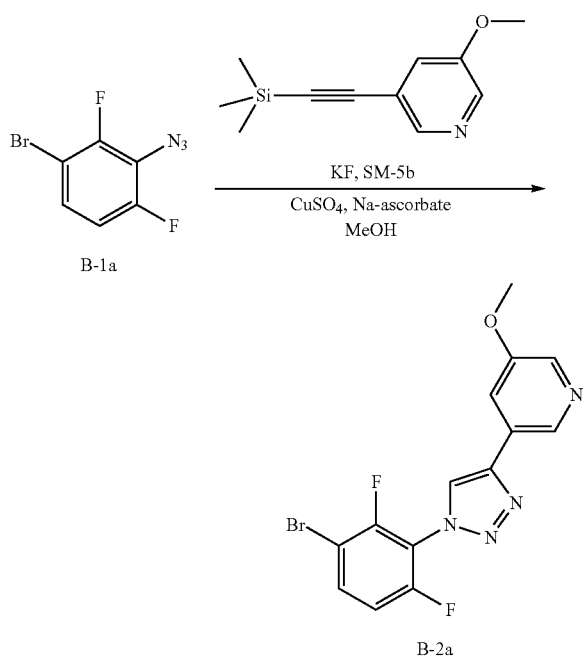

B-1a → B-2a

KF, SM-5b
CuSO$_4$, Na-ascorbate
MeOH

The azide B-1a (2.99 g, 12.8 mmol), the alkyne SM-5b (3.35 g, 16.3 mmol) and KF (1.33 g, 22.8 mmol) are taken-up in MeOH (60 mL). Na-ascorbate (7.49 mL, 1 N in $H_2O$, 7.49 mmol) and $CuSO_4$ (0.64 mL, 1 N in $H_2O$, 0.64 mmol) are added and the mixture is stirred at 45° C. overnight. The solvents are evaporated, the residue is taken-up in $H_2O$ and extracted 2× with EtOAc. The combined organic layer is dried over $MgSO_4$, filtered and evaporated. The residue is re-crystallized from isopropanol to yield the triazole B-2a (HPLC-MS: $t_{Ret.}$=1.25 min; MS $(M+H)^+$=367/369).

Analogously to this procedure additional triazoles B-2 can be prepared using various azides B-1 and alkynes SM-5.

TABLE 6

Triazoles B-2

| # | structure | $t_{Ret.}$ (HPLC) [min] | MS $(M + H)^+$ |
|---|---|---|---|
| B-2a | 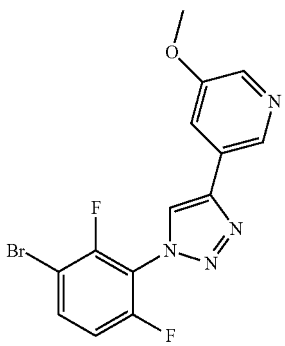 [SMILES: COc1cncc(-c2cn(-c3c(F)ccc(Br)c3F)nn2)c1] | 1.25 | 367/369 (Br) |
| B-2b | 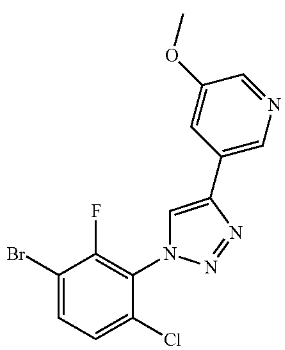 [SMILES: COc1cncc(-c2cn(-c3c(Cl)ccc(Br)c3F)nn2)c1] | 1.31 | 383/385/387 (Br, Cl) |

C.3. Synthesis of Anilines B-6
C.3.1. Experimental Procedure for the Synthesis of B6-a

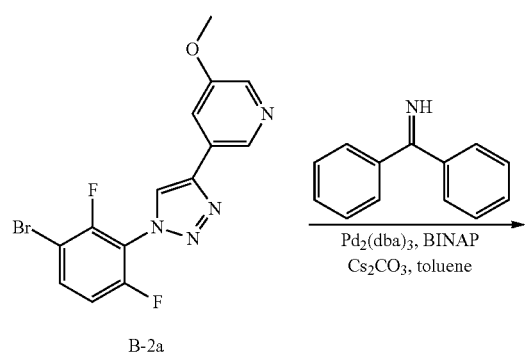

B-2a

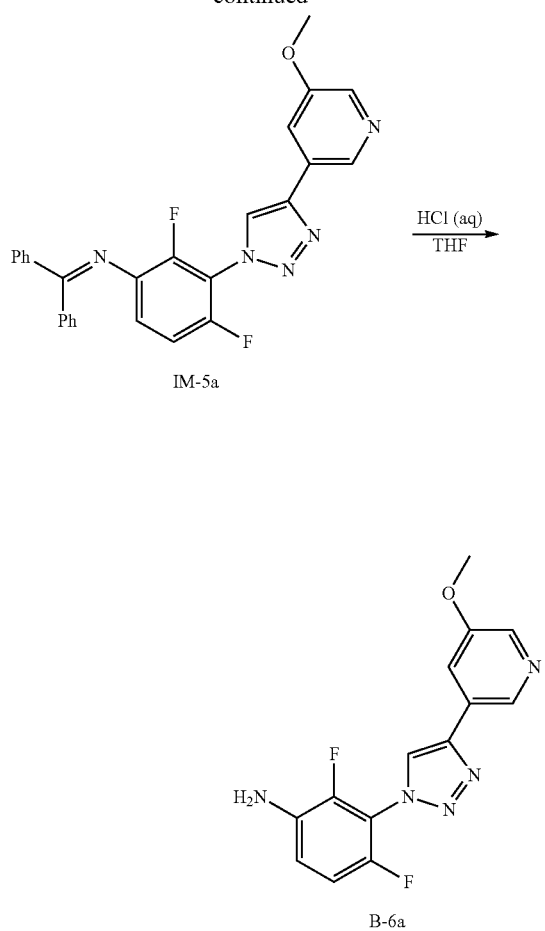

IM-5a

B-6a

Step 1

The triazole B-2a (1.70 g, 3.70 mmol), benzophenone-imine (794 mg, 4.25 mmol), $Pd_2(dba)_3$ (197 mg, 0.22 mmol), rac-BINAP (160 mg, 0.25 mmol) and $Cs_2CO_3$ (4.83 g, 14.8 mmol) are suspended under an inert atmosphere ($N_2$) in toluene (40 mL) and stirred at 100° C. overnight. After cooling to rt the mixture is filtered, adsorbed on silica gel and purified with NP MPLC using a gradient of DCM/MeOH (120 min., 100:0 to 95:5). The product containing fractions of IM-5a are evaporated, taken-up in $MeCN/H_2O$ and freeze dried.

Step 2

IM-5a (1.37 g, 1.76 mmol) is taken-up in THF (10 mL), conc. HCl (3 mL) is added and the mixture stirred at 40° C. for 2 h whereupon a precipitate is formed which is collected by to filtration. The solid is recrystallized from MeCN to yield the aniline B-6a (HPLC-MS: $t_{Ret.}$=0.99 min; MS $(M+H)^+$=304) which is used without further purification.

Analogously to this procedure additional anilines B-6 can be prepared using triazoles B-2 and the BUCHWALD HARTWIG conditions described above.

TABLE 7

Anilines B-6

| # | structure | $t_{Ret.}$ (HPLC) [min] | MS (M+H)+ |
|---|---|---|---|
| B-6a | 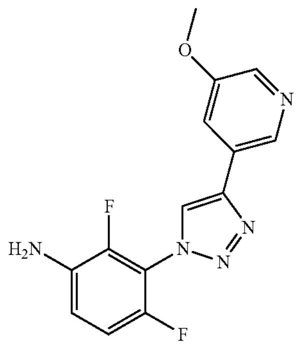 [SMILES: COc1cncc(-c2cn(-c3c(F)ccc(N)c3F)nn2)c1] | 0.99 | 304 |
| B-6b | 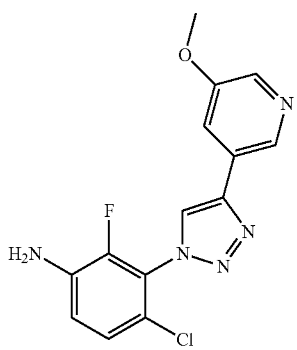 [SMILES: COc1cncc(-c2cn(-c3c(Cl)ccc(N)c3F)nn2)c1] | 1.10 | 320 |

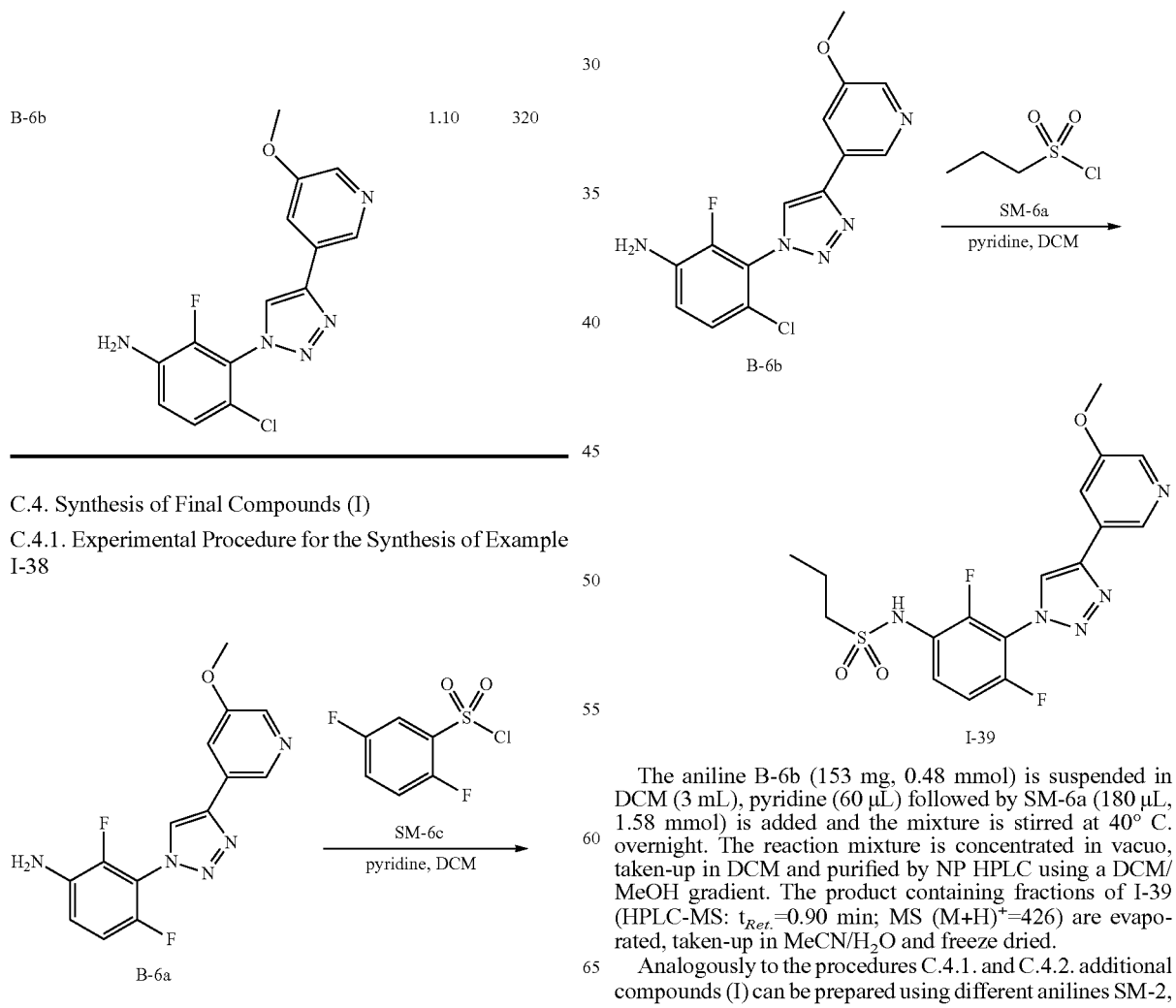

C.4. Synthesis of Final Compounds (I)

C.4.1. Experimental Procedure for the Synthesis of Example I-38

The aniline B-6a (56.6 mg, 0.19 mmol) is suspended in DCM (3 mL), pyridine (60 µL) followed by SM-6c (33 µL, 0.24 mmol) is added and the mixture is stirred at 40° C. overnight. Aqueous HCl (2 N) is added, the mixture is filtered and the filtrate evaporated. The residue is taken-up in MeCN/H$_2$O and purified by RP HPLC. The product containing fractions of I-38 (HPLC-MS: $t_{Ret.}$=0.94 min; MS (M+H)$^+$=480) are freeze dried.

C.4.2. Experimental Procedure for the Synthesis of Example I-39

The aniline B-6b (153 mg, 0.48 mmol) is suspended in DCM (3 mL), pyridine (60 µL) followed by SM-6a (180 µL, 1.58 mmol) is added and the mixture is stirred at 40° C. overnight. The reaction mixture is concentrated in vacuo, taken-up in DCM and purified by NP HPLC using a DCM/MeOH gradient. The product containing fractions of I-39 (HPLC-MS: $t_{Ret.}$=0.90 min; MS (M+H)$^+$=426) are evaporated, taken-up in MeCN/H$_2$O and freeze dried.

Analogously to the procedures C.4.1. and C.4.2. additional compounds (I) can be prepared using different anilines SM-2, alkynes SM-5 and sulfonyl chlorides SM-6.

TABLE 8

Structures and analytical data of compounds I-38 to I-47

| # | Struktur | Procedure | t_Ret. (HPLC) [min] | MS (M + H)+ |
|---|---|---|---|---|
| I-38 | | C.4.1. | 0.94 | 480 |
| I-39 | | C.4.2. | 0.90 | 426 |
| I-40 | | C.4.2. | 0.88 | 412 |
| I-41 | | C.4.2. | 0.89 | 426 |

TABLE 8-continued

Structures and analytical data of compounds I-38 to I-47

| # | Struktur | Procedure | t$_{Ret.}$ (HPLC) [min] | MS (M + H)$^+$ |
|---|---|---|---|---|
| I-42 | | C.4.1. | 0.81 | 445 |
| I-43 | | C.4.1. | 0.85 | 424 |
| I-44 | | C.4.1. | 0.88 | 480 |
| I-45 | | C.4.1. | 0.00 | 434 |

TABLE 8-continued

Structures and analytical data of compounds I-38 to I-47

| # | Struktur | Procedure | $t_{Ret.}$ (HPLC) [min] | MS $(M + H)^+$ |
|---|---|---|---|---|
| I-46 | 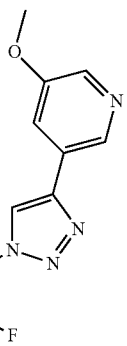 | C.4.1. | 0.84 | 422 |
| I-47 | 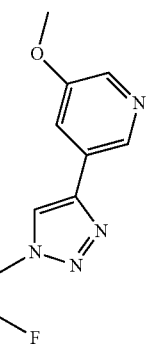 | C.4.1. | 1.04 | 434 |

The following examples describe the biological activity of the compounds according to the invention without restricting the invention to these examples.

Compounds of general formula (I) are characterised by their many possible applications in the therapeutic field. Particular mention should be made of those applications in which the inhibition of specific signal enzymes, particularly the inhibiting effect on the proliferation of cultivated human tumour cells but also on the proliferation of other cells such as endothelial cells, for example, are involved.

Kinase Test B-Raf (V600E)

In a dilution series 10 µL/well of test substance solution are placed in a multiwell plate. The dilution series is selected so that generally a range of concentrations of 2 µM to 0.119 nM or 0.017 nM is covered. If necessary the initial concentration of 2 µM is changed to 50 µM, 10 µM, 0.4 µM or 0.2857 µM and further dilution is carried out accordingly. The final concentration of DMSO is 5%. 10 µL/well of the B-Raf (V600E)-kinase solution are pipetted in (containing 0.5 ng B-Raf (V600E)-kinase, e.g. from Upstate) in 20 mM Tris-HCl pH 7.5, 0.1 mM EDTA, 0.1 mM EGTA, 0.286 mM sodium orthovanadate, 10% glycerol, 1 mg/mL bovine serum albumin, 1 mM dithiothreitol) and the mixture is incubated for 1 h at RT with shaking. The kinase reaction is started by the addition of 20 µL/well ATP solution [final concentration: 250 µM ATP, 30 mM Tris-HCl pH 7.5, 0.02% Brij, 0.2 mM sodium orthovanadate, 10 mM magnesium acetate, 0.1 mM EGTA, phosphatase cocktail (Sigma, # P2850, dilution recommended by the manufacturer)] and 10 µL/well MEK1 solution [containing 50 ng biotinylated MEK1 (prepared from purified MEK1 according to standard procedure, e.g. with EZ-Link Sulpho-NHS-LC-Biotin reagent, Pierce, #21335)] and carried out for 60 min at RT with constant shaking. The reaction is stopped by the addition of 12 µL/well of a 100 mM EDTA solution and incubation is continued for a further 5 min. 55 µL/well of the reaction solution are transferred into a streptavidin-coated plate (e.g. Streptawell HighBond, Roche, #11989685001) and gently shaken for 1 h at RT in order to bind biotinylated MEK1 to the plate. After elimination of the liquid the plate is washed five times with 200 µL/well of 1× PBS and 100 µL/well solution of primary antibody plus europium-labelled secondary antibody [Anti Phospho-MEK (Ser217/221), Cell Signaling, #9121 and Eu—N1 labelled goat-anti-rabbit antibody, Perkin Elmer, # AD0105] is added, the primary antibody is diluted 1:2000 and the secondary antibody is diluted to 0.4-0.5 µg/mL in Delfia Assay Buffer (Perkin Elmer, #1244-111). After 1 h shaking at RT the solution is poured away and washed five times with 200 µL/well Delfia Wash Buffer (Perkin Elmer, #4010-0010/#1244-114). After the addition of 200 µL/well Enhancement Solution (Perkin Elmer, #4001-0010/#1244-105) the mixture is shaken for 10 min at RT and then measured in a Wallac Victor using the program "Delfia Time Resolved Fluorescence (Europium)". $IC_{50}$ values are obtained from these dosage-activity curves using a software program (GraphPadPrizm).

Measurement of the Inhibition of the Proliferation of Cultivated Human Melanoma Cells (SK-MEL-28, B-RAF$^{V600E}$ Mutated)

For measuring the proliferation of cultivated human tumour cells, cells of the melanoma cell line SK-MEL-28 [from American Type Culture Collection (ATCC)] are cultivated in MEM medium, supplemented with 10% foetal calf serum, 2% sodium bicarbonate, 1 mM sodium pyruvate, 1% non-essential amino acids (e.g. from Cambrex, # BE13-

114E) and 2 mM glutamine. SK-MEL-28 cells are placed in 96-well flat bottomed dishes in a density of 2500 cells per well in supplemented MEM medium (see above) and incubated overnight in an incubator (at 37° C. and 5% $CO_2$). The active substances are added to the cells in different concentrations, so that a concentration range of 50 μM to 3.2 nM is covered. If necessary the initial concentration of 50 μM is changed to 10 μM or 2 μM and further dilution is carried out accordingly (up to 0.6 nM or 0.12 nM). After an incubation period of a further 72 h 20 μL AlamarBlue reagent (Serotec Ltd., # BUF012B) are added to each well and the cells are incubated for a further 3-6 h. The colour change of the AlamarBlue reagent is determined in a fluorescence spectrophotometer (e.g. Gemini, Molecular Devices). $EC_{50}$ values are calculated using a software program (GraphPadPrizm).

The $EC_{50}$ values of the example compounds determined using the above assay are shown in Table 9.

TABLE 9

| # | $EC_{50}$ SK-MEL-28 [nM] |
|---|---|
| I-1 | 113 |
| I-2 | 216 |
| I-3 | 82 |
| I-4 | 535 |
| I-5 | 1642 |
| I-6 | 559 |
| I-7 | 279 |
| I-8 | 305 |
| I-9 | 132 |
| I-10 | 107 |
| I-11 | 506 |
| I-12 | 201 |
| I-13 | 1018 |
| I-14 | 1716 |
| I-15 | 1822 |
| I-16 | 87 |
| I-17 | 1262 |
| I-18 | 75 |
| I-19 | 493 |
| I-20 | 245 |
| I-21 | 314 |
| I-22 | 231 |
| I-23 | 459 |
| I-24 | 117 |
| I-25 | 158 |
| I-26 | 98 |
| I-27 | 96 |
| I-28 | 88 |
| I-29 | 37 |
| I-30 | 1226 |
| I-31 | 1454 |
| I-32 | 114 |
| I-33 | 671 |
| I-34 | 218 |
| I-35 | 358 |
| I-36 | 589 |
| I-37 | 928 |
| I-38 | 363 |
| I-39 | 145 |
| I-40 | 327 |
| I-41 | 403 |
| I-42 | 292 |
| I-43 | 432 |
| I-44 | 776 |
| I-45 | 24 |
| I-46 | 480 |
| I-47 | 159 |
| I-48 | 545 |
| I-50 | 493 |
| I-51 | 114 |
| I-52 | 153 |
| I-53 | 68 |
| I-54 | 7 |
| I-55 | 32 |
| I-56 | 675 |
| I-57 | 306 |
| I-58 | 71 |
| I-59 | 98 |
| I-60 | 9 |
| I-61 | 10 |
| I-62 | 13 |
| I-63 | 44 |
| I-64 | 38 |
| I-65 | 32 |
| I-66 | 55 |
| I-67 | 4 |
| I-68 | 6 |
| I-69 | 5 |
| I-70 | 73 |
| I-71 | 61 |
| I-72 | 10 |
| I-73 | 44 |
| I-74 | 5 |
| I-75 | 273 |
| I-76 | 65 |

Measurement of the Inhibition of the Proliferation of Cultivated Human Melanoma Cells (A375, B-RAF$^{V600E}$ Mutated)

For measuring the proliferation of cultivated human tumour cells, cells of the melanoma cell line A375 [from the American Type Culture Collection (ATCC)] are cultivated in DMEM medium, supplemented with 10% foetal calf serum and 2% sodium bicarbonate. Test substances are tested on A375 cells according to the procedure described for SK-MEL-28 cells (see above), but seeding them at 5000 cells per well.

Most of the example compounds I-1 to I-76 show good to very good activity in the cellular A375 assay, i.e. an $EC_{50}$ value of less than 1000 nM, generally less than 500 nM.

The active substances are characterised in that they have a significantly lower antiproliferative activity on cell lines which have no B-RAF mutation. Thus, for example, example compounds I-1 to I-76 have an $EC_{50}$ value on melanoma cells (e.g. A375) without a B-Raf V600E mutation which is generally higher than that of B-RAF mutated melanoma cells (e.g. A375) by at least a factor of 10.

The $EC_{50}$ value of the phospho-ERK reduction and the $EC_{50}$ value of the antiproliferative activity in B-RAF mutated cell lines correlate well with cellular selectivity of the active substances.

Measurement of the Reduction of the Phospho-ERK Signal in Cultivated Human Melanoma Cells (SK-MEL-28, B-RAF$^{V600E}$ Mutated)

To measure the reduction in the phospho-ERK signal of cultivated human tumour cells, cells of the melanoma cell line SK-MEL-28 [from the American Type Culture Collection (ATCC)] in MEM medium, supplemented with 10% foetal calf serum, 2% sodium bicarbonate, 1 mM sodium pyruvate, 1% non-essential amino acids (e.g. obtained from Cambrex, # BE13-114E) and 2 mM glutamine, are cultivated. SK-MEL-28 cells are placed in 96-well flat bottomed dishes in a density of 7500 cells per well in supplemented MEM medium (see above) and incubated overnight in an incubator (at 37° C. and 5% $CO_2$). The active substances are added to the cells in different concentrations, so that a concentration range of 10 μM to 2.4 nM is covered. If necessary the initial concentration of 10 μM is changed to 50 μM or 2.5 μM and further dilution is carried out accordingly (up to 12.2 nM or 0.6 nM). After an incubation period of a further 2 h the cells are fixed with 4% formaldehyde and permeabilised with 0.1% Triton X-100 in PBS. Non-specific antibody binding is reduced by incubating with 5% skimmed milk powder dissolved in TBS-T. Phosphorylated ERK is detected with a murine monoclonal anti-diphosphorylated ERK1/2 antibody (from Sigma, #M8159). After washing steps using 0.1% Tween 20 in PBS the bound first antibody is detected by the second antibody (peroxidase coupled polyclonal rabbit anti mouse IgG from DAKO #P0161). After further washing steps the substrate (TMB Peroxidase Substrate Solution made by Bender MedSystems #BMS406) is added. The colour reaction is stopped after a few minutes with 1 M phosphoric acid. The staining is measured at 450 nm with a Spectra Max Plus reader made by Molecular Devices. $EC_{50}$ values are calculated using a software program (GraphPadPrizm).

The $EC_{50}$ value of the phospho-ERK reduction of the example compounds determined using the above assay is generally less than 500 nM.

The substances of the present invention are B-RAF-kinase inhibitors. As can be demonstrated by DNA staining followed by FACS or Cellomics Array Scan analysis, the inhibition of proliferation achieved by means of the compounds according to the invention is brought about above all by preventing entry into the DNA synthesis phase. The treated cells arrest in the G1 phase of the cell cycle.

Accordingly, the compounds according to the invention are also tested on other tumour cells. For example these compounds are effective on colon carcinoma lines, e.g. Colo205, HT29, and may be used in this and other indications. This demonstrates the usefulness of the compounds according to the invention for the treatment of different types of tumours.

On the basis of their biological properties the compounds of general formula (I) according to the invention, their tautomers, racemates, enantiomers, diastereomers, mixtures thereof and the salts of all the above-mentioned forms are suitable for treating diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia); bone diseases and cardiovascular diseases (e.g. restenosis and hypertrophy). They are also suitable for protecting proliferating cells (e.g. hair, intestinal, blood and progenitor cells) from DNA damage caused by radiation, UV treatment and/or cytostatic treatment.

For example, the following cancers may be treated with compounds according to the invention, without being restricted thereto:
brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon carcinoma, colorectal carcinoma, anal carcinoma, carcinoma of the large bowel, tumours of the small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas (NSCLC) such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell to anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma, vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (I) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxy-progesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor (PDGF)", "fibroblast growth factor (FGF)", "vascular endothelial growth factor (VEGF)", "epidermal growth factor (EGF)", "insuline-like growth factors (IGF)", "human epidermal growth factor (HER, e.g. HER2, HER3, HER4)" and "hepatocyte growth factor (HGF)"), inhibitors are for example "growth factor" antibodies, "growth factor receptor" antibodies and tyrosine kinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); tubuline inhibitors; PARP inhibitors, topoisomerase inhibitors (e.g. epipodophyllotoxins such as for example etoposide and etopophos, teniposide, amsacrin, topotecan, irinotecan, mitoxantron), serine/threonine kinase inhibitors (e.g. PDK 1 inhibitors, B-Raf inhibitors, mTOR inhibitors, mTORC1 inhibitors, PI3K inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein protein interaction inhibitors (e.g. IAP, Mcl-1, MDM2/MDMX), MEK inhibitors, ERK inhibitors, IGF-1R inhibitors, ErbB receptor inhibitors, rapamycin analogs (e.g. everolimus, temsirolimus, ridaforolimus, sirolimus) and various chemotherapeutic agents such as amifostin, anagrelid, clodronat, filgrastin, interferon, interferon alpha, leucovorin, rituximab, procarbazine, levamisole, mesna, mitotane, pamidronate and porfimer.

Other possible combination partners are 2-chlorodesoxyadenosine, 2-fluorodesoxy-cytidine, 2-methoxyoestradiol, 2C4, 3-alethine, 131-I-TM-601, 3CPA, 7-ethyl-10-hydroxycamptothecin, 16-aza-epothilone B, A 105972, A 204197, abiraterone, aldesleukin, alitretinoin, allovectin-7, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, AMG-479 (ganitumab), ARRY 162, ARRY 438162, ARRY-300, ARRY-142886/AZD-6244 (selumetinib), ARRY-704/AZD-8330, AR-12, AR-42, AS-703988, AXL-1717, AZD-8055, AZD-5363, AZD-6244, ARQ-736, ARQ 680, AS-703026 (primasertib), avastin, AZD-2014, azacytidine, azaepothilone B, azonafide, BAY-43-9006, BAY 80-6946, BBR-3464, BBR-3576, bevacizumab, BEZ-235, biricodar dicitrate, BCX-1777, BKM-120, bleocin, BLP-25, BMS-184476, BMS-247550, BMS-188797, BMS-275291, BMS-663513, BMS-754807, BNP-1350, BNP-7787, BIBW 2992 (afatinib, tomtovok), BIBF 1120 (vargatef), BI 836845, BI 2536, BI 6727, BI 836845, BI 847325, BI 853520, BIIB-022, bleomycinic acid, bleomycin A, bleomycin B, brivanib, bryostatin-1, bortezomib, brostallicin, busulphan, BYL-719, CA-4 prodrug, CA-4, CapCell, calcitriol, canertinib, canfosfamide, capecitabine, carboxyphthalatoplatin, CCI-779, CC-115, CC-223, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, CKI-27, clofarabin, colchicin, combretastatin A4, COT inhibitors, CHS-828, CH-5132799, CLL-Thera, CMT-3 cryptophycin 52, CTP-37, CTLA-4 monoclonal antibodies, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, DS-7423, E7010, E-6201, edatrexat, edotreotide, efaproxiral, eflornithine, EGFR inhibitors, EKB-569, EKB-509, enzastaurin, elsamitrucin, epothilone B, epratuzumab, ER-86526, erlotinib, ET-18-OCH3, ethynylcytidine, ethynyloestradiol, exatecan, exatecan mesylate, exemestane, exisulind, fenretinide, figitumumab, floxuridine, folic acid, FOLFOX, FOLFOX4, FOLFIRI, formestane, fotemustine, galarubicin, gallium maltolate, gefinitib, gemtuzumab, gimatecan, glufosfamide, GCS-100, GDC-0623, GDC-0941 (pictrelisib), GDC-0980, GDC-0032, GDC-0068, GDC-0349, GDC-0879, G17DT immunogen, GMK, GPX-100, gp100-peptide vaccines, GSK-5126766, GSK-690693, GSK-1120212 (trametinib), GSK-2118436 (dabrafenib), GSK-2126458, GSK-2132231A, GSK-2334470, GSK-2110183, GSK-2141795, GW2016, granisetron, herceptine, hexamethylmelamine, histamine, homoharringtonine, hyaluronic acid, hydroxyurea, hydroxyprogesterone caproate, ibandronate, ibritumomab, idatrexate, idenestrol, IDN-5109, IGF-1R inhibitors, IMC-1C11, IMC-A12 (cixutumumab), immunol, indisulam, interferon alpha-2a, interferon alpha-2b, pegylated interferon alpha-2b, interleukin-2, INK-1117, INK-128, INSM-18, ionafarnib, ipilimumab, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, KW-2450, lobaplatin, leflunomide, lenograstim, leuprolide, leuporelin, lexidronam, LGD-1550, linezolid, lutetium texaphyrin, lometrexol, losoxantrone, LU 223651, lurtotecan, LY-S6AKT1, LY-2780301, mafosfamide, marimastat, mechloroethamine, MEK inhibitors, MEK-162, methyltestosteron, methylprednisolone, MEDI-573, MEN-10755, MDX-H210, MDX-447, MDX-1379, MGV, midostaurin, minodronic acid, mitomycin, mivobulin, MK-2206, MK-0646 (dalotuzumab), MLN518, motexafin gadolinium, MS-209, MS-275, MX6, neridronate, neratinib, Nexavar, neovastat, nilotinib, nimesulide, nitroglycerin, nolatrexed, norelin, N-acetylcysteine, 06-benzylguanine, oblimersen, omeprazole, oncophage, oncoVEX$^{GM-CSF}$, ormiplatin, ortataxel, OX44 antibodies, OSI-027, OSI-906 (linsitinib), 4-1BB antibodies, oxantrazole, oestrogen, panitumumab, patupilone, pegfilgrastim, PCK-3145, pegfilgrastim, PBI-1402, PBI-05204, PDO325901, PD-1 antibodies, PEG-paclitaxel, albumin-stabilized paclitaxel, PEP-005, PF-05197281, PF-05212384, PF-04691502, PHT-427, P-04, PKC412, P54, PI-88, pelitinib, pemetrexed, pentrix, perifosine, perillylalcohol, pertuzumab, PI3K inhibitors, PI3K/mTOR inhibitors, PG-TXL, PG2, PLX-4032/RO-5185426 (vemurafenib), PLX-3603/RO-5212054, PT-100, PWT-33597, PX-866, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, R115777, RAF-265, ramosetron, ranpirnase, RDEA-119/BAY 869766, RDEA-436, rebeccamycin analogues, receptor tyrosine kinase (RTK) inhibitors, revimid, RG-7167, RG-7304, RG-7421, RG-7321, RG 7440, rhizoxin, rhuMAb, rinfabate, risedronate, rituximab, robatumumab, rofecoxib, RO-31-7453, RO-5126766, RO-5068760, RPR 109881A, rubidazone, rubitecan, R-flurbiprofen, RX-0201, S-9788, sabarubicin, SAHA, sargramostim, satraplatin, SB 408075, Se-015/Ve-015, SU5416, SU6668, SDX-101, semustin, seocalcitol, SM-11355, SN-38, SN-4071, SR-27897, SR-31747, SR-13668, SRL-172, sorafenib, spiroplatin, squalamine, suberanilohydroxamic acid, sutent, T 900607, T 138067, TAK-733, TAS-103, tacedinaline, talaporf in, Tarceva, tariquitar, to tasisulam, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymalfasin, thymectacin, tiazofurin, tipifarnib, tirapazamine, tocladesine, tomudex, toremofin, trabectedin, TransMID-107, transretinic acid, traszutumab, tremelimumab, tretinoin, triacetyluridine, triapine, triciribine, trimetrexate, TLK-286TXD 258, tykerb/tyverb, urocidin, valrubicin, vatalanib, vincristine, vinflunine, virulizin, WX-UK1, WX-554, vectibix, xeloda, XELOX, XL-147, XL-228, XL-281, XL-518/R-7420/GDC-0973, XL-765, YM-511, YM-598, ZD-4190, ZD-6474, ZD-4054, ZD-0473, ZD-6126, ZD-9331, ZDI839, ZSTK-474, zoledronat and zosuquidar.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) | Tablets | per tablet |
|---|---|---|
| | active substance according to formula (I) | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance according to formula (I) | 80 mg |
| | lactose | 55 mg |
| | corn starch | 190 mg |
| | microcrystalline cellulose | 35 mg |
| | polyvinylpyrrolidone | 15 mg |
| | sodiumcarboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) | Ampoule solution | |
|---|---|---|
| | active substance according to formula (I) | 50 mg |
| | sodium chloride | 50 mg |
| | water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of the formula (I)

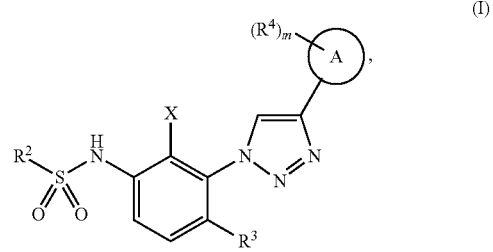

wherein
R$^2$ is a group optionally substituted by one or more, identical or different R$^{b1}$ and/or R$^{c1}$, selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl, C$_{6-10}$aryl, 5-10 membered heteroaryl and 3-10 membered heterocyclyl or R$^2$ is —NR$^{c1}$R$^{c1}$;
each R$^{b1}$ is independently selected from among —OR$^{c1}$, —NR$^{c1}$R$^{c1}$, halogen, —CN, —C(O)R$^{c1}$, —C(O)OR$^{c1}$, —C(O)NR$^{c1}$R$^{c1}$, —S(O)$_2$R$^{c1}$, —S(O)$_2$NR$^{c1}$R$^{c1}$, —NHC(O)R$^{c1}$ and —N(C$_{1-4}$alkyl)C(O)R$^{c1}$ as well as the bivalent substituent =O, wherein the latter may only be a substituent in non-aromatic ring systems;
each R$^{c1}$ independently of one another denotes hydrogen or a group selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl, C$_{6-10}$aryl, 5-10 membered heteroaryl and 3-10 membered heterocyclyl;
R$^3$ is selected from among hydrogen, halogen, C$_{1-4}$alkyl, C$_{1-4}$alkyloxy, C$_{2-4}$alkenyl, C$_{2-4}$alkynyl, C$_{1-4}$haloalkyl, —CN, —NH(C$_{1-4}$alkyl) and —N(C$_{1-4}$alkyl)$_2$;
ring A is a 5-10 membered heteroaryl;
m denotes the number 0, 1 or 2;
each R$^4$ independently of one another denotes a group optionally substituted by one or more, identical or different R$^{a2}$ and/or R$^{b2}$, selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl, C$_{6-10}$aryl, 5-10 membered heteroaryl and 3-11 membered heterocyclyl, or is independently selected from among —OR$^{a3}$, —NR$^{a3}$R$^{a3}$, —N(OR$^{a3}$)R$^{a3}$, halogen, —CN, —C(O)R$^{a3}$, —C(O)OR$^{a3}$, —C(O)NR$^{a3}$R$^{a3}$, —C(NH)NR$^{a3}$R$^{a3}$, —S(O)$_2$R$^{a3}$, —S(O)$_2$NR$^{a3}$R$^{a3}$, —NHC(O)R$^{a3}$ and —N(C$_{1-4}$alkyl)C(O)R$^{a3}$
each R$^{a2}$ independently of one another denotes a group optionally substituted by one or more, identical or different R$^{b2}$ and/or R$^{c2}$, selected from among C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl and 3-10 membered heterocyclyl;
each R$^{b2}$ is independently selected from among —OR$^{c2}$, —NR$^{c2}$R$^{c2}$, halogen, —C(O)R$^{c2}$, —C(O)OR$^{c2}$, —C(O)NR$^{c2}$R$^{c2}$, —CN, —NHC(O)R$^{c2}$ and —NHC(O)OR$^{c2}$;
each R$^{c2}$ independently of one another denotes hydrogen or a group selected from among C$_{1-6}$alkyl, C$_{2-6}$alkenyl, C$_{2-6}$alkynyl, C$_{3-6}$cycloalkyl, C$_{4-6}$cycloalkenyl and 3-10 membered heterocyclyl, wherein this heterocyclyl is optionally substituted by one or more, identical or different substituents selected from among halogen, $C_{1-6}$alkyl and —C(O)—$C_{1-6}$alkyl;

each $R^{a3}$ independently of one another denotes hydrogen or a group optionally substituted by one or more, identical or different $R^{b3}$ and/or $R^{c3}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;

each $R^{b3}$ is independently selected from among —$OR^{c3}$, —$NR^{c3}R^{c3}$, halogen, —$C(O)R^{c3}$, —$C(O)OR^{c3}$, —$C(O)NR^{c3}R^{c3}$, —CN, —$NHC(O)R^{c3}$ and —$NHC(O)OR^{c3}$;

each $R^{c3}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl, $C_{1-6}$alkyl-O—$C_{1-6}$alkyl, $(C_{1-4}$alkyl)HN—$C_{1-6}$alkyl, $(C_{1-4}$alkyl)$_2$N—$C_{1-6}$alkyl, $C_{1-6}$haloalkyl, 4-16 membered heterocyclylalkyl and 3-10 membered heterocyclyl, wherein the heterocyclyl ring in aforementioned groups is optionally substituted by one or more, identical or different $C_{1-6}$alkyl;

X denotes chlorine or fluorine;

wherein the compounds (I) may optionally also be present in the form of the tautomers, racemates, enantiomers, diastereomers and the mixtures thereof or as the respective salts of all the above-mentioned forms.

2. The compound according to claim 1, wherein
$R^2$ is selected from among $C_{1-6}$alkyl, $C_{1-4}$alkoxy-$C_{1-4}$alkyl, 5-6 membered heteroaryl, $C_{3-6}$cycloalkyl, $C_{4-7}$cycloalkylalkyl and phenyl substituted with one or more, identical or different halogen.

3. The compound according to claim 2, wherein
$R^2$ denotes $C_{1-6}$alkyl or phenyl substituted with one or more, identical or different halogen.

4. The compound according to claim 3, wherein
$R^2$ denotes $C_{1-6}$alkyl.

5. The compound according to claim 4, wherein
$R^2$ is selected from among ethyl, n-propyl, iso-propyl, n-butyl and iso-butyl.

6. The compound according to claim 5, wherein
$R^2$ is selected from among ethyl, n-propyl, iso-propyl and iso-butyl.

7. The compound according to claim 6, wherein
$R^2$ is n-propyl.

8. The compound according to claim 2, wherein
$R^2$ is 5-6 membered heteroaryl.

9. The compound according to claim 8, wherein
$R^2$ is furyl or pyridinyl.

10. The compound according to claim 9, wherein
$R^2$ is furyl.

11. The compound according to claim 10, wherein
$R^2$ is

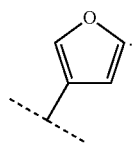

12. The compound according to claim 2, wherein
$R^2$ is difluorphenyl.

13. The compound according to claim 1, wherein
$R^3$ is halogen.

14. The compound according to claim 13, wherein
$R^3$ is fluorine.

15. The compound according to claim 1, wherein
ring A is a nitrogen-containing 5-10 membered heteroaryl.

16. The compound according to claim 15, wherein
ring A is a nitrogen-containing 5-6 membered heteroaryl.

17. The compound according to claim 16, wherein
ring A is selected from among pyridyl, pyrimidyl and pyrazolyl.

18. The compound according to claim 17, wherein
ring A is pyridyl.

19. The compound according to claim 1, wherein
m denotes 1;
$R^4$ is 3-11 membered heterocyclyl optionally substituted by one or more, identical or different $R^{a2}$ and/or $R^{b2}$
each $R^{a2}$ independently of one another denotes a group optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;
each $R^{b2}$ is independently selected from among —$OR^{c2}$, —$NR^{c2}R^{c2}$, halogen, —$C(O)R^{c2}$, —$C(O)OR^{c2}$, —$C(O)NR^{c2}R^{c2}$, —CN, —$NHC(O)R^{c2}$ and —$NHC(O)OR^{c2}$, and
each $R^{c2}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl and 3-10 membered heterocyclyl, wherein this heterocyclyl is optionally substituted by one or more, identical or different substituents selected from among halogen, $C_{1-6}$alkyl and —C(O)—$C_{1-6}$alkyl.

20. The compound according to claim 19, wherein
m denotes 1;
$R^4$ is 4-7 membered, nitrogen-containing heterocyclyl optionally substituted by one or more, identical or different $R^{a2}$ and/or $R^{b2}$
each $R^{a2}$ independently of one another denotes a group optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;
each $R^{b2}$ is independently selected from among —$OR^{c2}$, —$NR^{c2}R^{c2}$, halogen, —$C(O)R^{c2}$, —$C(O)OR^{c2}$, —$C(O)NR^{c2}R^{c2}$, —CN, —$NHC(O)R^{c2}$ and —$NHC(O)OR^{c2}$, and
each $R^{c2}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl and 3-10 membered heterocyclyl, wherein this heterocyclyl is optionally substituted by one or more, identical or different substituents selected from among halogen, $C_{1-6}$alkyl and —C(O)—$C_{1-6}$alkyl.

21. The compound according to claim 20, wherein
m denotes 1;
$R^4$ is selected from among piperazinyl, piperidinyl and morpholinyl, all optionally substituted by one or more, identical or different $R^{a2}$ and/or $R^{b2}$
each $R^{a2}$ independently of one another denotes a group optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;
each $R^{b2}$ is independently selected from among —$OR^{c2}$, —$NR^{c2}R^{c2}$, halogen, —$C(O)R^{c2}$, —$C(O)OR^{c2}$, —$C(O)NR^{c2}R^{c2}$, —CN, —$NHC(O)R^{c2}$ and —$NHC(O)OR^{c2}$, and each $R^{c2}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl and 3-10 membered heterocyclyl, wherein this heterocyclyl is optionally substituted by one or more, identical or different substituents selected from among halogen, $C_{1-6}$alkyl and —C(O)—$C_{1-6}$alkyl.

22. The compound according to claim 21, wherein
each $R^{a2}$ independently of one another denotes a group optionally substituted by one or more, identical or different $R^{b2}$ and/or $R^{c2}$, selected from among $C_{1-6}$alkyl, $C_{2-6}$alkenyl, $C_{2-6}$alkynyl, $C_{1-6}$haloalkyl, $C_{3-6}$cycloalkyl and 3-10 membered heterocyclyl;
each $R^{b2}$ is independently selected from among —$OR^{c2}$, —$NR^{c2}R^{c2}$, halogen, —C(O)$NR^{c2}R^{c2}$ and —CN, and
each $R^{c2}$ independently of one another denotes hydrogen or a group selected from among $C_{1-6}$alkyl, $C_{3-6}$cycloalkyl and 3-10 membered heterocyclyl, wherein this heterocyclyl is optionally substituted by one or more, identical or different substituents selected from among halogen, $C_{1-6}$alkyl and —C(O)—$C_{1-6}$alkyl.

23. The compound according to claim 1, wherein
m denotes 1;
$R^4$ is selected from among —$OR^{a3}$ and —$NR^{a3}R^{a3}$;
each $R^{a3}$ independently of one another denotes hydrogen or a group optionally substituted by one or more, identical or different $R^{b3}$ and/or $R^{c3}$, selected from among $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl and 3-10 membered heterocyclyl;
each $R^{b3}$ is independently selected from among —$OR^{c3}$, —$NR^{c3}R^{c3}$, halogen, —C(O)$R^{c3}$, —C(O)$OR^{c3}$, —C(O)$NR^{c3}R^{c3}$, —CN, —NHC(O)$R^{c3}$ and —NHC(O)$OR^{c3}$;
each $R^{c3}$ independently of one another denotes hydrogen or a group selected from among $C_{1-6}$alkyl, $C_{2-6}$alkenyl, $C_{2-6}$alkynyl, $C_{3-6}$cycloalkyl, $C_{4-6}$cycloalkenyl, $C_{1-6}$alkyl-O—$C_{1-6}$alkyl, $(C_{1-4}$alkyl)HN—$C_{1-6}$alkyl, $(C_{1-4}$alkyl)$_2$N—$C_{1-6}$alkyl, $C_{1-6}$haloalkyl, 4-16 membered heterocyclylalkyl and 3-10 membered heterocyclyl, wherein the heterocyclyl ring in aforementioned groups is optionally substituted by one or more, identical or different $C_{1-6}$alkyl.

24. The compound according to claim 1, wherein
m denotes 1 and
$R^4$ is imidazolyl, optionally substituted by one, two or three, identical or different $C_{1-4}$alkyl.

25. The compound according to claim 1, wherein
m denotes 0.

26. The compound according to claim 1, wherein
m denotes 1;
$R^4$ and ring A together is

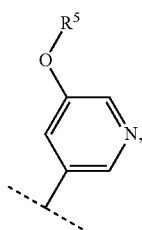

wherein
$R^5$ is $C_{1-6}$alkyl.

27. The compound according to claim 26, wherein
m denotes 1 and
$R^4$ and ring A together is

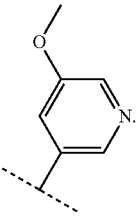

28. The compound according to claim 1, wherein
m denotes 1 and
$R^4$ and ring A together is

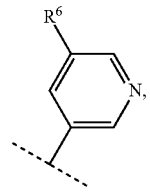

wherein
$R^6$ is selected from among fluorine, chlorine and bromine.

29. The compound according to claim 1, wherein
m denotes 1 and
$R^4$ and ring A together is

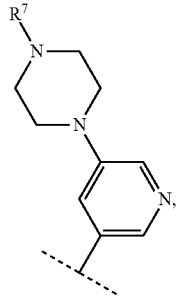

wherein
$R^7$ is selected from among $C_{1-6}$alkyl, $C_{2-6}$alkynyl, $C_{3-6}$cycloalkyl, $C_{4-12}$cycloalkylalkyl, 3-6 membered heterocyclyl, —C(O)$C_{1-6}$alkyl and $C_{1-6}$alkyloxy-$C_{1-6}$alkyl.

30. The compound according to claim 29, wherein
m denotes 1 and
$R^4$ and ring A together is

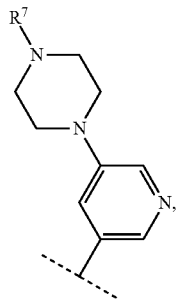

wherein
R⁷ is selected from $C_{1-6}$alkyl, $C_{3-6}$cycloalkyl, $C_{4-12}$cycloalkylalkyl, —C(O)$C_{1-6}$alkyl and $C_{1-6}$alkyloxy-$C_{1-6}$alkyl.
31. The compound according to claim 1, wherein X denotes chlorine.
32. The compound according to claim 1, wherein X denotes fluorine.
33. A compound, or pharmaceutically acceptable salts thereof, selected from among:
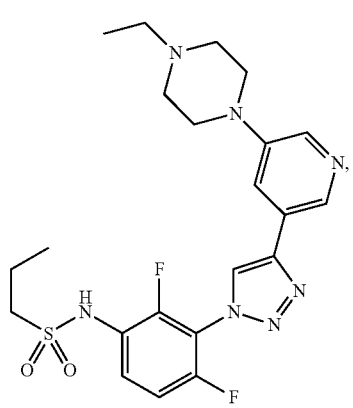
I-1
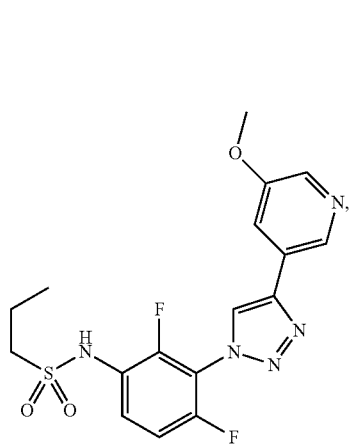
I-2
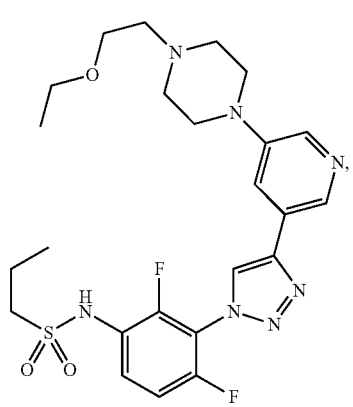
I-3
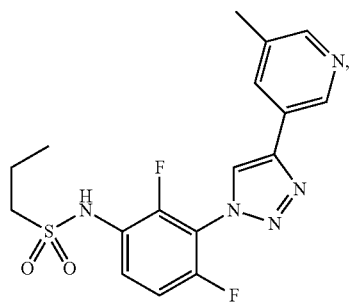
I-4
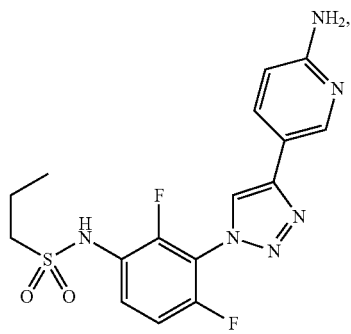
I-5
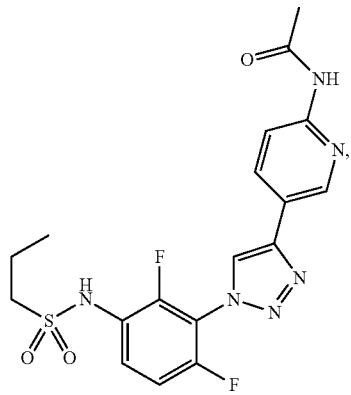
I-6
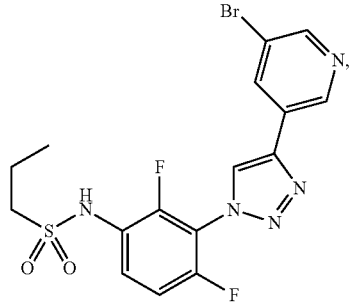
I-7

I-8
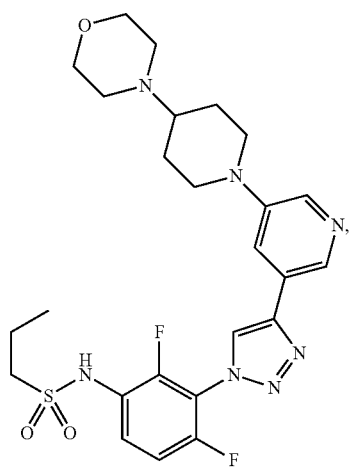
I-9
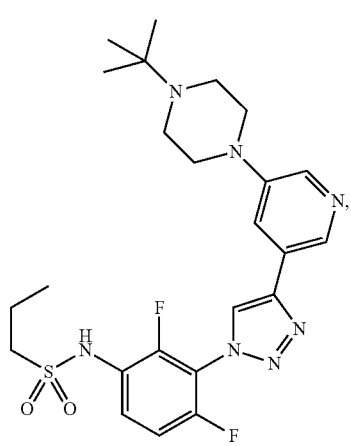
I-10
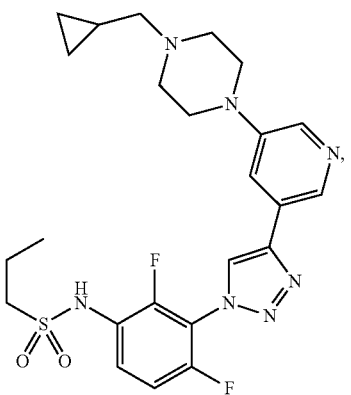
I-11
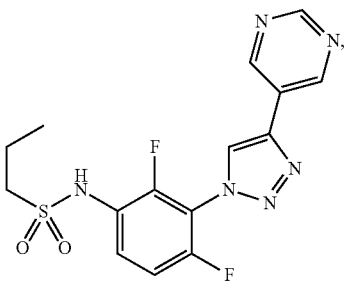
I-12
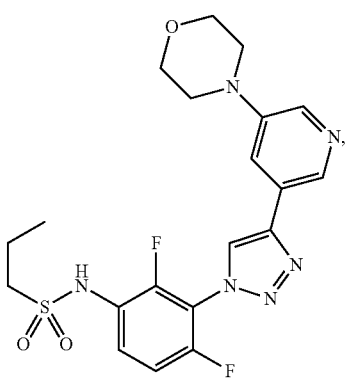
I-13
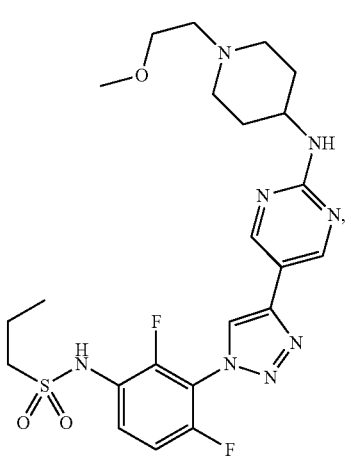
I-14
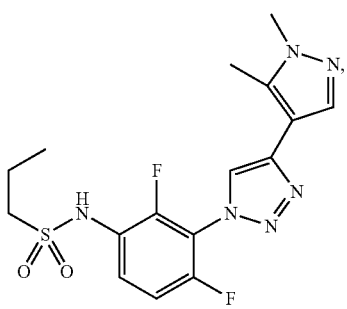
I-15
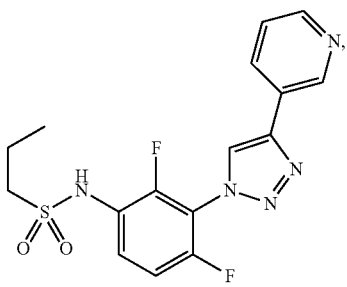

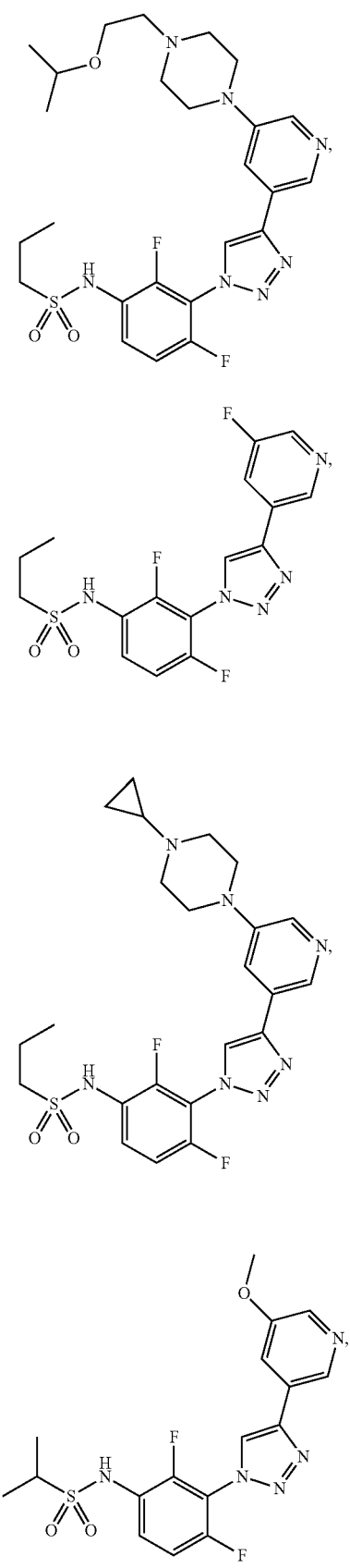
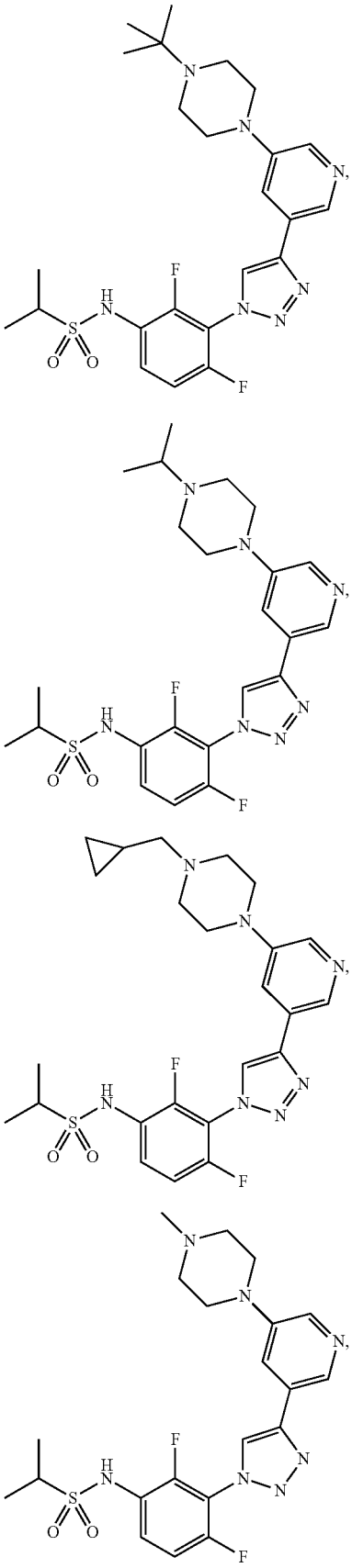

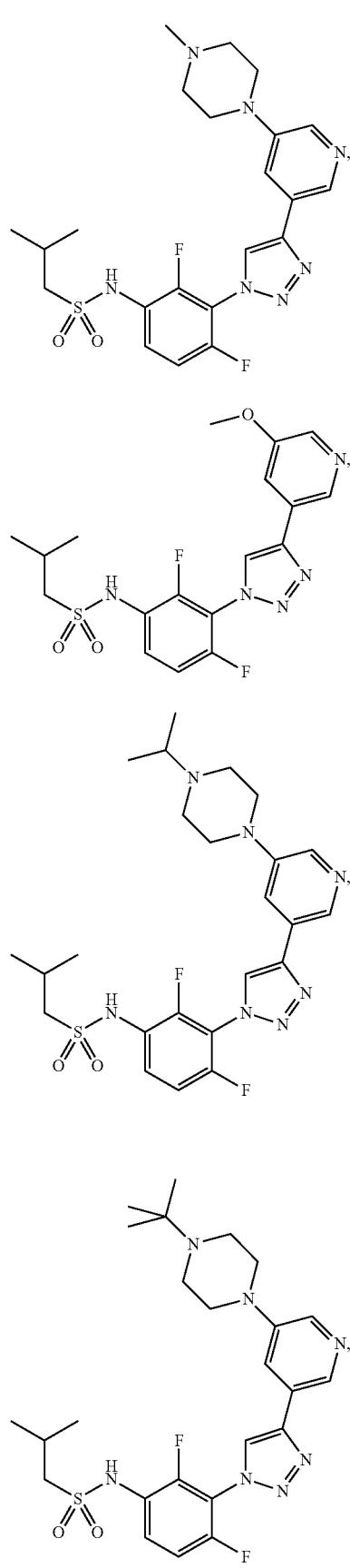
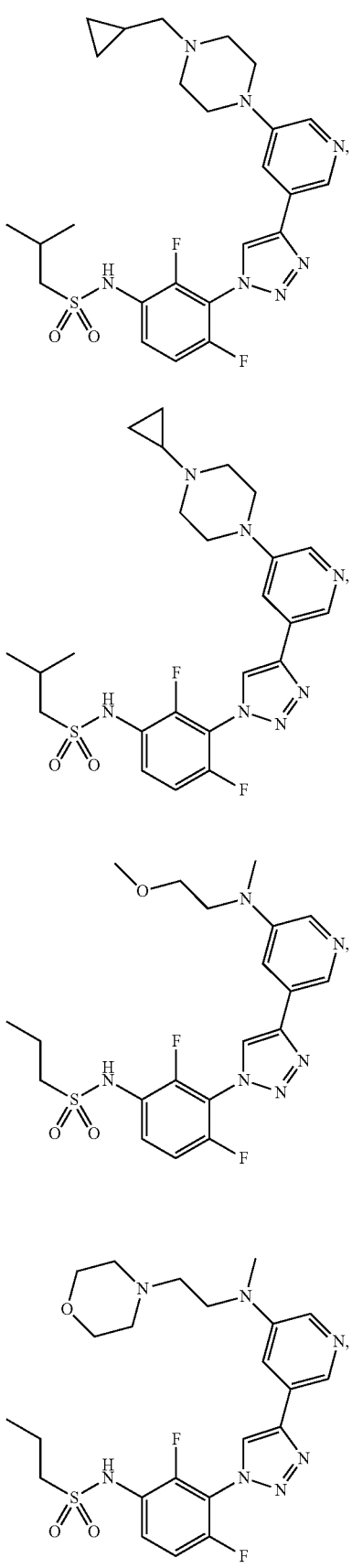

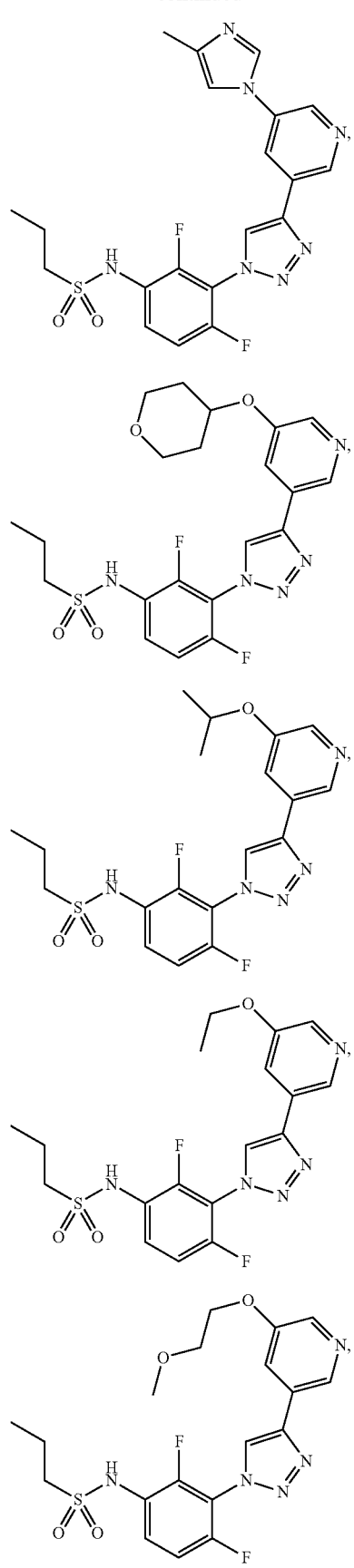
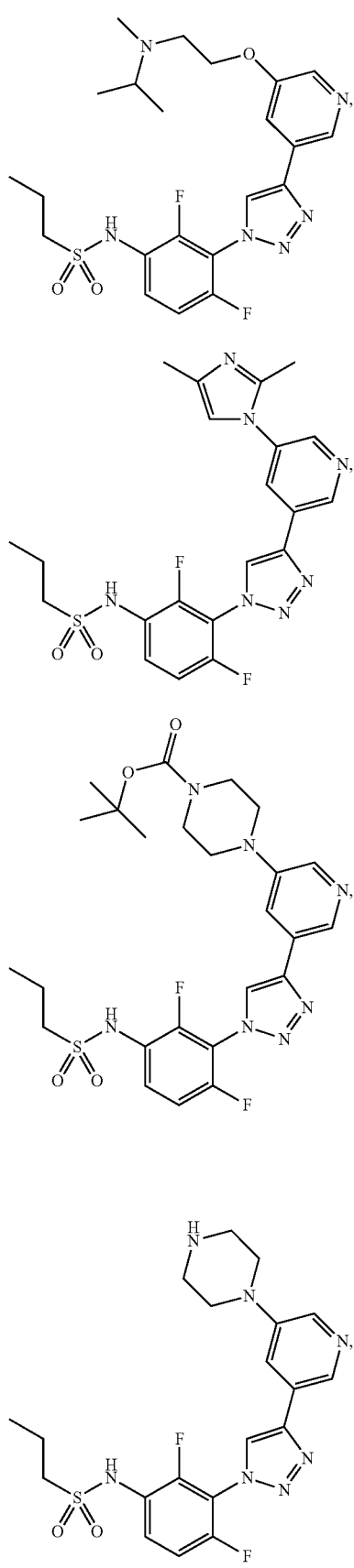

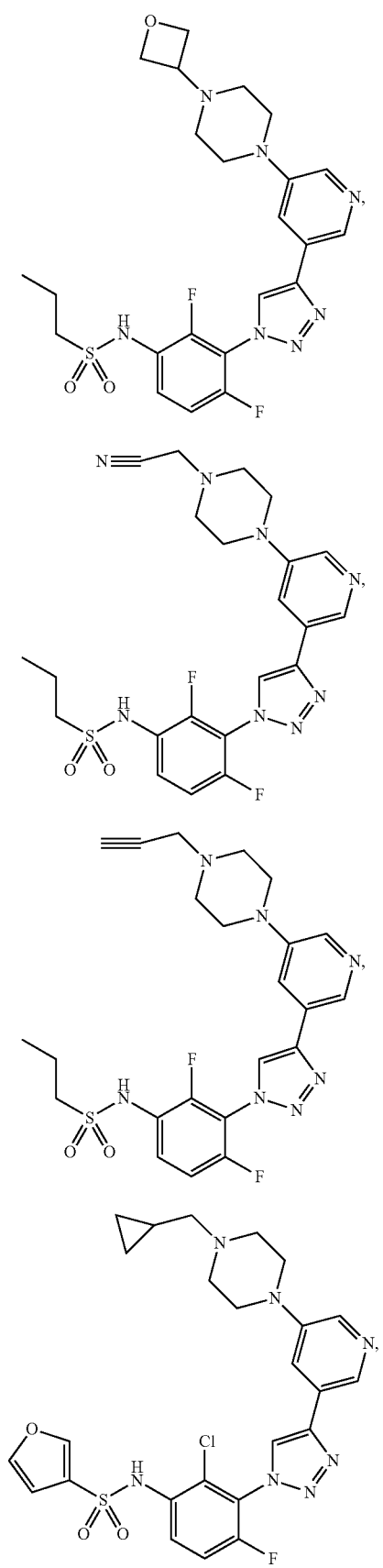
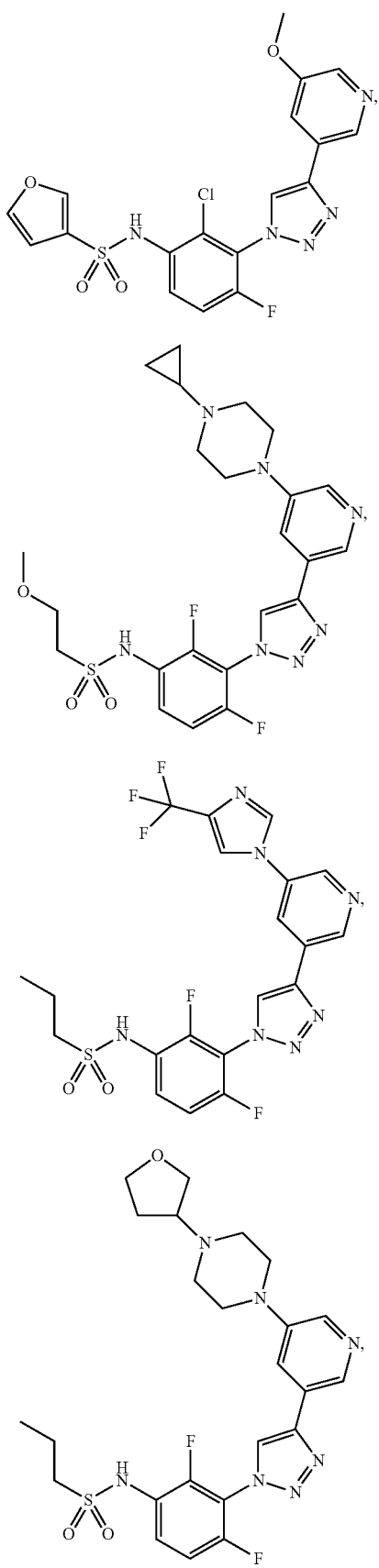

I-59
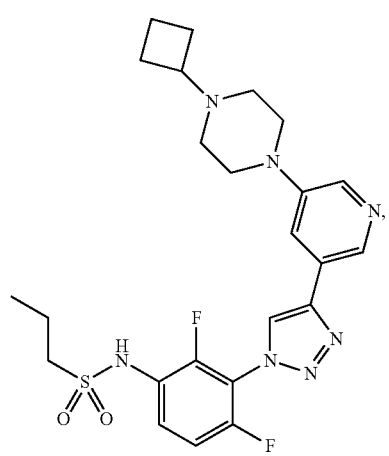
I-62
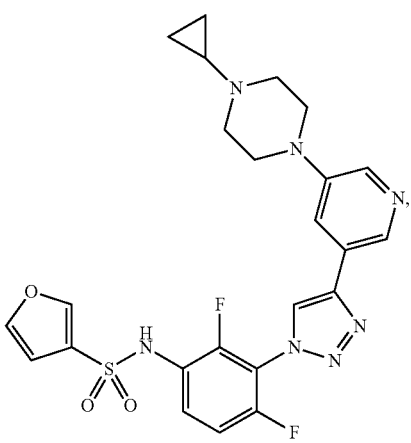
I-60
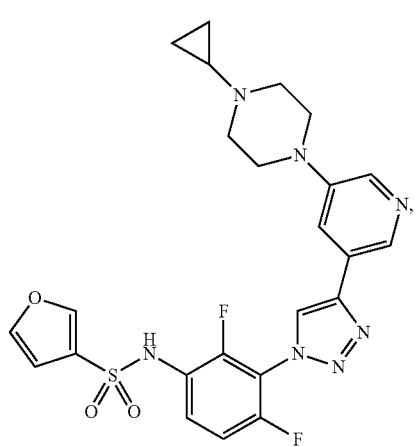
I-63
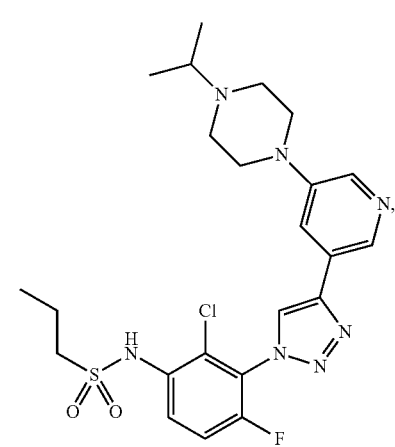
I-61
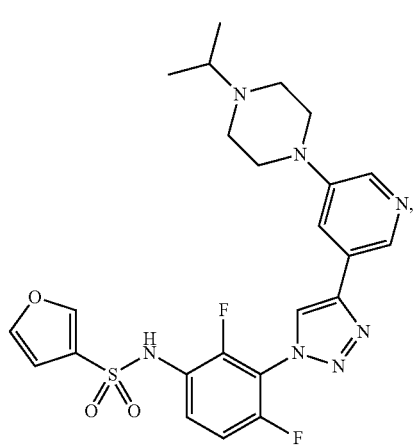
I-64
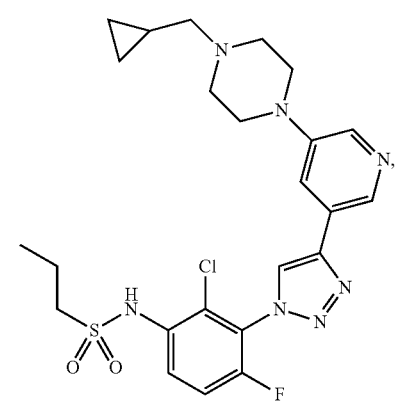

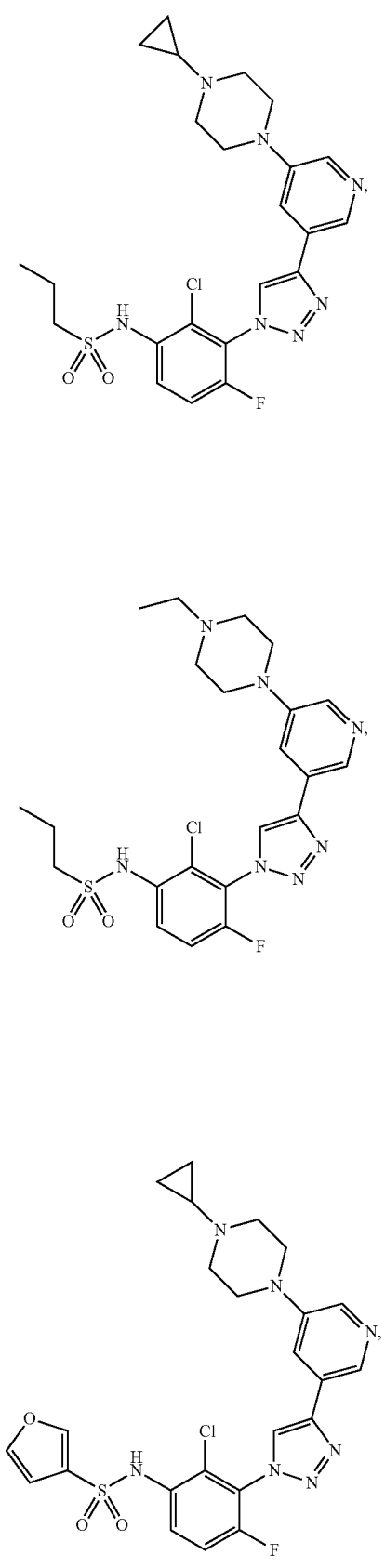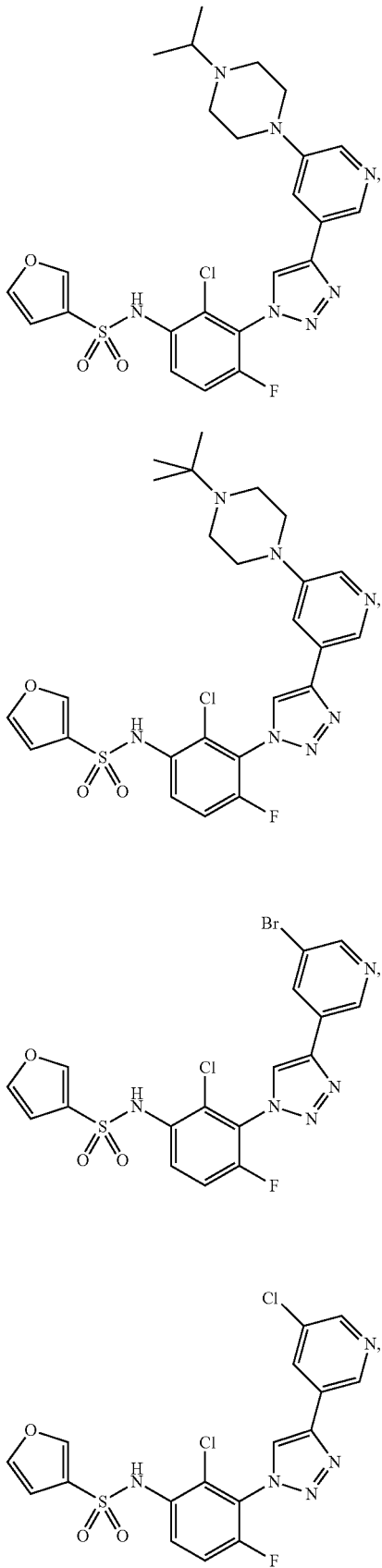

I-72
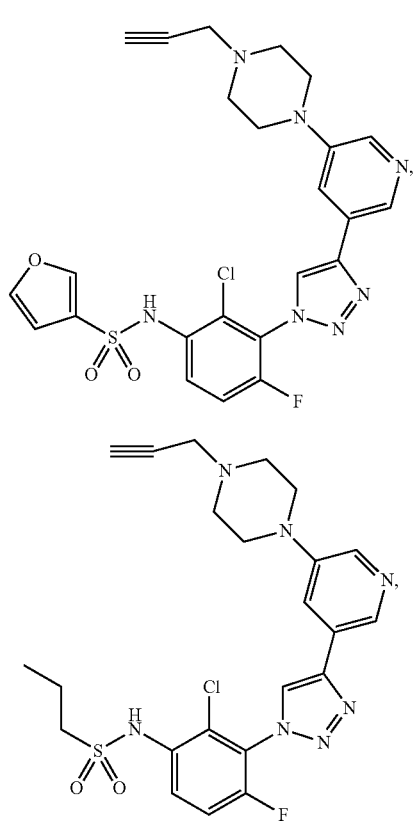
I-73
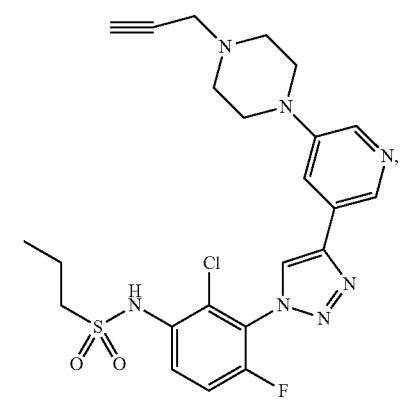
I-74
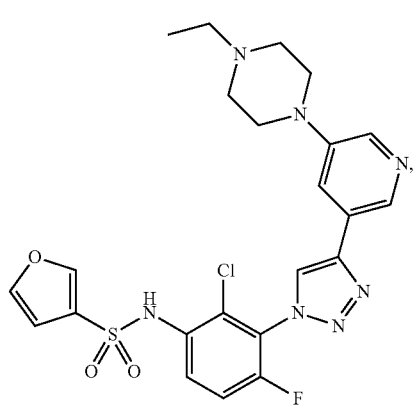
I-75
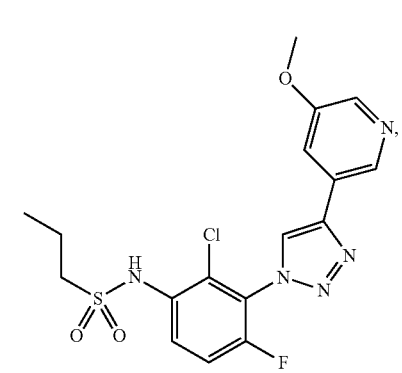
I-76
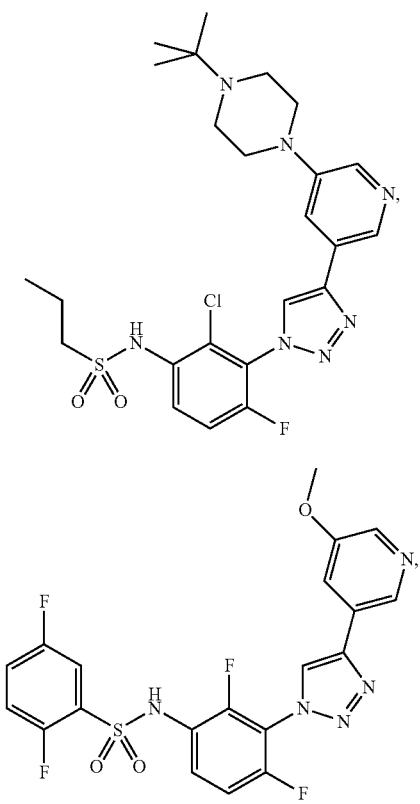
I-38
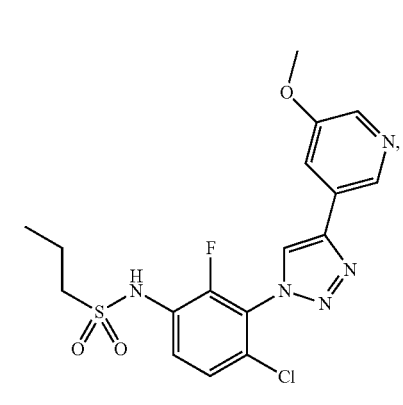
I-39
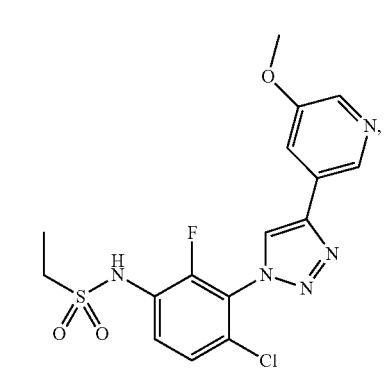
I-40
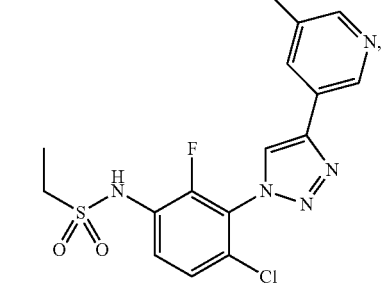

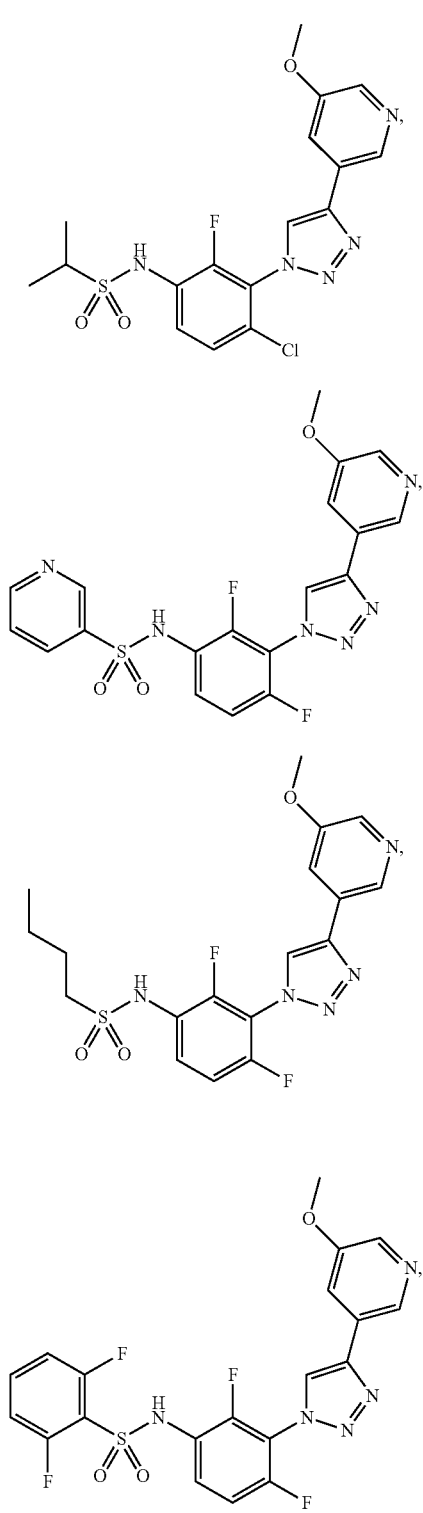
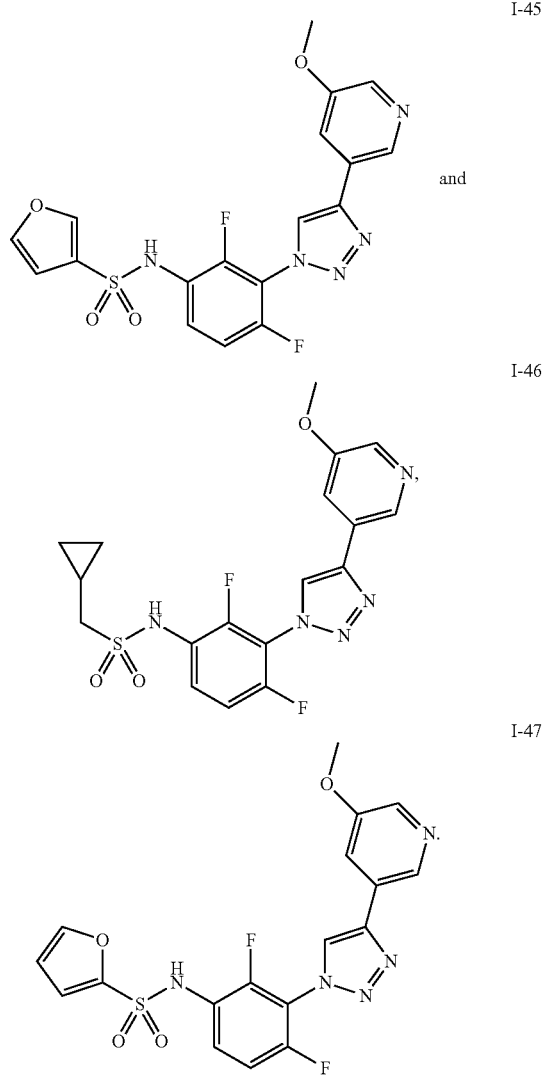

34. A method of treating a cancer selected from colon carcinomas, melanoma, cancer of the gall bladder and thyroid carcinomas comprising administering to a patient a therapeutically effective amount of a compound according to claim 1 or the pharmaceutically acceptable salts thereof.

35. The method according to claim 34 wherein the patient is a human being.

36. A pharmaceutical composition comprising a therapeutically effective amount of a compound of formula (I) according to claim 1 or the pharmaceutically acceptable salts thereof optionally in combination with conventional excipients and/or carriers.

37. The pharmaceutical composition according to claim 36 and at least one other cytostatic or cytotoxic active substance, different from formula (I).

* * * * *